(12) United States Patent
Donaldson et al.

(10) Patent No.: US 8,603,788 B2
(45) Date of Patent: Dec. 10, 2013

(54) MODIFIED YEAST STRAINS EXHIBITING ENHANCED FERMENTATION OF LIGNOCELLULOSIC HYDROLYSATES

(75) Inventors: Jennifer Donaldson, Ontario (CA); Jan-Maarten A. Geertman, Voorschoten (NL); Glenn D. Munkvold, Ontario (CA); Gary Pigeau, Ontario (CA); Philippe J. Dufresne, Quebec (CA); Loreta Gudynaite-Savitch, Ontario (CA)

(73) Assignee: Iogen Energy Corporation, Ottawa (CA)

( * ) Notice: Subject to any disclaimer, the term of this patent is extended or adjusted under 35 U.S.C. 154(b) by 86 days.

(21) Appl. No.: 12/981,890

(22) Filed: Dec. 30, 2010

(65) Prior Publication Data

US 2011/0159560 A1 Jun. 30, 2011

Related U.S. Application Data

(60) Provisional application No. 61/307,536, filed on Feb. 24, 2010, provisional application No. 61/291,011, filed on Dec. 30, 2009.

(51) Int. Cl.
*C12P 7/10* (2006.01)
*C12N 9/00* (2006.01)
*C12N 9/42* (2006.01)
*C12N 1/20* (2006.01)
*C12N 15/00* (2006.01)
*C07H 21/04* (2006.01)

(52) U.S. Cl.
USPC ........ 435/165; 435/183; 435/209; 435/252.3; 435/320.1; 536/23.2

(58) Field of Classification Search
None
See application file for complete search history.

(56) References Cited

U.S. PATENT DOCUMENTS

| | | | |
|---|---|---|---|
| 2,203,360 | A | 6/1940 | Partansky |
| 4,342,831 | A | 8/1982 | Faber et al. |
| 5,789,210 | A | 8/1998 | Ho et al. |
| 5,866,382 | A | 2/1999 | Hallborn et al. |
| 6,410,302 | B1 | 6/2002 | Traff et al. |
| 6,475,768 | B1 | 11/2002 | Otero et al. |
| 6,582,944 | B1 | 6/2003 | Hallborn et al. |
| 6,737,258 | B2 | 5/2004 | Hames et al. |
| 7,455,997 | B2 | 11/2008 | Hughes |
| 7,527,927 | B1 * | 5/2009 | Ho et al. ............... 435/6.18 |
| 7,527,951 | B2 | 5/2009 | Londesborough et al. |
| 7,622,284 | B2 | 11/2009 | Op Den Camp et al. |
| 2006/0216804 | A1 | 9/2006 | Karhumaa |
| 2007/0082386 | A1 | 4/2007 | Gorwa-Grauslund |
| 2008/0171370 | A1 | 7/2008 | Holmes et al. |
| 2009/0004726 | A1 | 1/2009 | Liu |
| 2009/0061490 | A1 | 3/2009 | Edwards et al. |
| 2009/0061502 | A1 | 3/2009 | Nilsson et al. |

FOREIGN PATENT DOCUMENTS

| | | |
|---|---|---|
| EP | 0450430 A2 | 10/1991 |
| WO | 03/062430 A1 | 7/2003 |
| WO | 03/078642 | 9/2003 |
| WO | 2005/091733 | 10/2005 |
| WO | 2005/111214 | 11/2005 |
| WO | 2005108552 A1 | 11/2005 |
| WO | 2005/118814 | 12/2005 |
| WO | 2006096130 A1 | 9/2006 |
| WO | 2008041840 A1 | 4/2008 |
| WO | 2008124162 A2 | 10/2008 |

OTHER PUBLICATIONS

Ho et al. Appl Environ Microbiol. May 1998;64(5):1852-9.*
Zweytick et al. Eur J Biochem. Feb. 2000;267(4):1075-82.*
Maya et al. Biotechnol Lett. Jun. 2008;30(6):979-87.*
Belinchón et al. FEMS Yeast Res. Sep. 2007;7(6):808-18. Epub Apr. 12, 2007.*
Madhavan et al. Appl Microbiol Biotechnol. Apr. 2009;82(6):1067-78. Epub Dec. 3, 2008.*
Ho, N.W.Y., et al., "Genetically Engineered *Saccharomyces* Yeast Capable of Effective Cofermentation of Glucose and Xylose", Appl. Env. Microbiol., May 1998, vol. 64, No. 5, pp. 1852-1859.
Ozcan, S. and Johnston, M., "Function and Regulation of Yeast Hexose Transporters", Microbiol. Mol. Biol. Rev., 1999, vol. 63, No. 3, pp. 554-569.
Abbott et al. (2007) Generic and specific transcriptional responses to different weak organic acids in anaerobic chemostat cultures of *Saccharomyces cerevisiae*. FEMS Yeast Res. 7:819-33.
Almeida et al. (2007) Mini-review: Increased tolerance and conversion of inhibitors in lignocellulosic hydrolysates by *Saccharomyces cerevisiae*. J. Chem. Technol. Biotechnol. 82:340-49.
Almeida et al. (2008) *Pichia stipitis* xylose reductase helps detoxifying lignocellulosic hydrolysate by reducing 5-hydroxymethyl-furfural (HMF). Biotechnol. Biofuels 1:12 (9 pp.).
Almeida et al. (2008) NADH- vs NADPH-coupled reduction of 5-hydroxymethyl furfural (HMF) and its implications on product distribution in *Saccharomyces cerevisiae*. Appl. Microbiol. Biotechnol. 78:939-45.
Bro et al. (2004) Genome-wide transcriptional response of a *Saccharomyces cerevisiae* strain with an altered redox metabolism. Biotechnol. Bioeng. 85(3):269-76.
Endo et al. (2008) Genome-wide screening of the genes required for tolerance to vanillin, which is a potential inhibitor of bioethanol fermentation, in *Saccharomyces cerevisiae*. Biotechnol. Biofuels 1:3 (6 pp., plus Additional files (6 pp.)).
Gorsich et al. (2006) Tolerance to furfural-induced stress is associated with pentose phosphate pathway genes ZWF1, GND1, RPE1, and TKL1 in *Saccharomyces cerevisiae*. Appl. Microbiol. Biotechnol. 71:339-49.

(Continued)

*Primary Examiner* — Christian Fronda
(74) *Attorney, Agent, or Firm* — Fitzpatrick, Cella, Harper & Scinto

(57) ABSTRACT

The present invention relates to novel xylose-fermenting yeast strains (for example, yeast of the genus *Saccharomyces*, e.g., *S. cerevisiae*) with an enhanced ability to ferment the xylose (and/or another pentose sugar) present in a lignocellulosic hydrolysate to a fermentation product(s) (for example, an alcohol (e.g., ethanol) or a sugar alcohol (e.g., xylitol)).

17 Claims, 22 Drawing Sheets

(56) References Cited

OTHER PUBLICATIONS

Huang et al. (2009) Enhanced ethanol production by fermentation of rice straw hydrolysate without detoxification using a newly adapted strain of *Pichia stipitis*. Bioresource Technol. 100:3914-20.

Jin et al. (2004) *Saccharomyces cerevisiae* Engineered for Xylose Metabolism Exhibits a Respiratory Response. Appl. Environ. Microbiol. 70(11):6816-25.

Kawahata et al. (2006) Yeast genes involved in response to lactic acid and acetic acid: acidic consition caused by the organic acids in *Saccharomyces cerevisiae* cultures induce expression of intrcellular metal metabolism genes regulated by Aft1p. FEMS Yeast Res. 6:924-36.

Klinke et al. (2004) Inhibition of ethanol-producing yeast and bacteria by degradation products produced during pretreatment of biomass. Appl. Microbiol. Biotechnol. 66:10-26.

Kuepfer et al. (2005) Metabolic functions of duplicate genes in *Saccharomyces cerevisiae*. Genome Res. 15:1421-30.

Lin et al. (2009) Comparative Proteomic Analysis of Tolerance and Adaptation of Ethanologenic *Saccharomyces cerevisiae* to Furfural, a Lignocellulosic Inhibitory Compound. Appl. Environ. Microbiol. 75(11):3765-76.

Liu et al. (2004) Adaptive response of yeasts to furfural and 5-hydroxymethylfurfural and new chemical evidence for HMF conversion to 2,5-bis-hydroxymethylfuran. J. Ind. Microbiol. Biotechnol. 31:345-52.

Liu et al. (2005) Enhanced Biotransformation of Furfural and Hydroxymethylfurfural by newly Developed Ethanologenic Yeast Strains. Appl. Biochem. Biotechnol. 121-124:451-60.

Liu et al. (2008) Multiple gene-mediated NAD(P)H-dependent aldehyde reduction is a mechanisms of in situ detoxification of furfural and 5-hydroxymethyl furfural by *Saccharomyces cerevisiae*. Appl. Microbiol. Biotechnol. 81:743-53.

Liu and M00n (2009) A novel NADPH-dependent aldehyde reductase gene from *Saccharomyces cerevisiae* NRRL Y-12632 involved in the detoxification of aldehyde inhibitors derived from lignocellulosic biomass conversion. Gene 446:1-10.

Martin et al. (2007) Adaptation of a recombinant xylose-utilizing *Saccharomyces cerevisiae* strain to a sugarcane bagasse hydrolysate with high content of fermentation inhibitors. Bioresource Technol. 98:1767-73.

Matsufuji et al. (2008) Acetaldehyde tolerance in *Saccharomyces cerevisiae* involves the pentose phosphate pathway and oleic acid biosynthesis. Yeast 25:825-33.

Modig et al. (2002) Inhibition effects of furfural on alcohol dehydrogenase, aldehyde dehydrogenase and pyruvate dehydrogenase. Biochem. J. 363:769-76.

Nilsson et al. (2005) Cofactor dependence in furan reduction by *Saccharomyces cerevisiae* in fermentation of acid-hydrolyzed lignocellulose. Appl. Environ. Microbiol. 71(12):7866-71.

Nikko et al. (2008) Arrestin-like proteins mediate ubiquitination and endocytosis of the yeast metal transporter Smf1. EMBO reports 9:1216-21.

Padilla et al. (1998) The highly conserved, coregulated SNO and SNZ Gene Families in *Saccharomyces cerevisiae* Respond to Nutrient Limitation. J. Bacteriol. 180(21):5718-26.

Pasha et al. (2007) Strain improvement of thermotolerant *Saccharomyces cerevisiae* VS3 strain for better utilization of lignocellulosic substrates. J. Appl. Microbiol. 103:1480-89.

Petersson et al. (2006) A 5-hydroxymethyl furfural reducing enzyme encoded by the *Saccharomyces cerevisiae* ADH6 gene conveys HMF tolerance. Yeast 23:455-64.

Powers and Barlowe (2002) Erv14p Directs a transmembrane secretory protein into COPII-coated transport vesicles. Mol. Biol. Cell 13:880-91.

Salusjarvi et al. (2008) Regulation of xylose metabolism in recombinant *Saccharomyces cerevisiae*. Microb. Cell Fact. 7:18 (16 pp).

Shimazu et al. (2005) A family of basic amino acid transporters of the vacuolar membrane from *Saccharomyces cerevisiae*. J. Biol. Chem. 280(6):4851-57.

Sonderegger et al. (2004) Metabolic engineering of a phosphoketolase pathway for pentose catabolism in *Saccharomyces cerevisiae*. Appl. Environ. Microbiol. 70(5):2892-97.

Tran and Chambers (1986) Ethanol fermentation of red oak acid prehydrolysate by the yeast *Pichia stipitis* CBS 5776. Enzyme Microb. Technol. 8:439-44.

Valachovic et al. (2001) Anaerobiosis induces comples changes in sterol esterification pattern in the yeast *Saccharomyces cerevisiae*. FEMS Microbiol. Lett. 197:41-45.

Jeffries et al. (2001) Genetic Engineering of Xylose Fermentation in Yeasts. (11 pp.; webpage found at http://www2.biotech.wisc.edu/jeffries/bioprocessing/xoferm/xoferm.html; printed Feb. 28, 2011; possible publication date as determined by Wayback Machine (see http://waybackmachine.org) is Nov. 6, 2001).

Perez-Ortin et al. (2002) Molecular Characterization of a Chromosomal Rearrangement Involved in the Adaptive Evolution of Yeast Strains. Genome Res. 12:1533-39.

U.S. Department of Energy (Jun. 2006) Breaking the Biological Barriers to Cellulose Ethanol: A Joint Research Agenda, DOE/SC-0095, (A Research Roadmap Resulting from the Biomass to Biofuels Workshop, Dec. 7-9, 2005, Rockville, Maryland; 206 pp., plus 10 introductory pages; printed Feb. 28, 2011).

Katahira, et al., "Ethanol fermentation from lignocellulosic hydrolysate by a recombinant xylose- and cellooligosaccharide-assimilating yeast strain", Appl. Microbiol. Biotechnol., vol. 72, No. 6 (2006) 1136-43.

Maitra, "A glucokinase from *Saccharomyces cerevisiae*", The Journal of Biological Chemistry, vol. 245, No. 9 (1970) 2423-31.

Wahlbom et al., "Molecular Analysis of a Saccharomyces cerevisiae Mutant with Improved Ability to Utilize Xylose Shows Enhanced Expression of Proteins Involved in Transport, Initial Xylose Metabolism and the Pentose Phosphate Pathway", Applied and Environmental Microbiology, vol. 69, No. 2 (2003) 740-46.

* cited by examiner

MODIFIED YEAST STRAINS EXHIBITING ENHANCED FERMENTATION OF LIGNOCELLULOSIC HYDROLYSATES

RELATED APPLICATIONS

This application claims the benefit of priority from U.S. Provisional Patent Application No. 61/291,011, filed Dec. 30, 2009, and No. 61/307,536, filed Feb. 24, 2010; the content of each application is hereby incorporated by reference herein in its entirety.

INCORPORATION OF SEQUENCE LISTING

The Sequence Listing filed on Dec. 30, 2010, created/modified on Dec. 30, 2010, named SEQLIST 01039019800ST25.txt, having a size in bytes of 4 kB, is hereby incorporated by reference herein in its entirety.

FIELD OF THE INVENTION

The present invention relates to novel yeast strains with enhanced ability to utilize the lignocellulosic hydrolysates for growth and/or fermentation.

BACKGROUND

Plant cell walls consist mainly of the large biopolymers cellulose, hemicellulose, lignin, and pectin. Cellulose and hemicellulose constitute an important renewable and inexpensive carbon source for the production of fermentable sugars. Cellulose consists of D-glucose units linked together in linear chains via beta-1,4 glycosidic bonds. Hemicellulose consists primarily of a linear xylan backbone comprising D-xylose units linked together via beta-1,4 glycosidic bonds and numerous side chains linked to the xylose units via glycosidic or ester bonds (e.g., L-arabinose, acetic acid, ferulic acid, etc.).

The term lignocellulose is commonly used to describe plant-derived biomass comprising cellulose, hemicellulose and lignin. Much attention and effort has been applied in recent years to the production of fuels and chemicals, primarily ethanol, from lignocellulose-containing feedstocks, such as agricultural wastes and forestry wastes, due to their low cost and wide availability. These agricultural and forestry wastes are typically burned or landfilled; thus, using these lignocellulosic feedstocks for ethanol production offers an attractive alternative to disposal. Yet another advantage of these feedstocks is that the lignin byproduct, which remains after the cellulose conversion process, can be used as a fuel to power the process instead of fossil fuels. Several studies have concluded that, when the entire production and consumption cycle is taken into account, the use of ethanol produced from cellulose generates close to zero greenhouse gases.

In comparison, fuel ethanol from feedstocks such as cornstarch, sugar cane, and sugar beets suffers from the limitation that these feedstocks are already in use as a food source for humans and animals. A further disadvantage of the use of these feedstocks is that fossil fuels are used in the conversion processes. Thus, these processes have only a limited impact on reducing greenhouse gases.

Lignocellulosic biomass has also been considered for producing other fermentation products besides ethanol. Examples of such products include lactic acid, sorbitol, acetic acid, citric acid, ascorbic acid, propanediol, butanediol, xylitol, acetone, and butanol.

The first chemical processing step for converting lignocellulosic feedstock to ethanol or other fermentation products involves hydrolysis of the cellulose and hemicellulose polymers, such as glucose and xylose, which can be converted to ethanol or other fermentation products in a subsequent fermentation step. Hydrolysis of the cellulose and hemicellulose can be achieved with a single-step chemical treatment or with a two-step process with milder chemical pretreatment followed by enzymatic hydrolysis of the pretreated lignocellulose with cellulase enzymes.

In a single-step chemical treatment, the lignocellulosic feedstock is contacted with a strong acid or alkali under conditions sufficient to hydrolyze both the cellulose and hemicellulose components of the feedstock to sugar monomers.

In a two-step chemi-enzymatic hydrolysis process, the lignocellulosic feedstock is first subjected to a pretreatment under conditions that are similar to, but milder than, those in the concentrated acid or alkali hydrolysis process. The purpose of the pretreatment is to increase the cellulose surface area and convert the fibrous feedstock to a muddy texture, with limited conversion of the cellulose to glucose. If the pretreatment is conducted with acid, the hemicellulose component of the feedstock is hydrolyzed to xylose, arabinose, galactose, and mannose. The resulting hydrolysate, which is enriched in pentose sugars derived from the hemicellulose, may be separated from the solids and used in a subsequent fermentation process to convert the pentose sugars to ethanol or other products. If the pretreatment is conducted with alkali, very little hydrolysis of the polysaccharides occurs; however, the alkali treatment opens up the surface of the lignocellulose by reacting with acidic groups present on the hemicellulose.

After the pretreatment step, the cellulose is subjected to enzymatic hydrolysis with one or more cellulase enzymes such as exo-cellobiohydrolases (CBH), endoglucanases (EG) and beta-glucosidases (beta-G). The CBH and EG enzymes catalyze the hydrolysis of the $\beta$-1,4-D-glucan linkages in the cellulose. The CBH enzymes, e.g., CBHI and CBHII, act on the ends of the glucose polymers in cellulose microfibrils and liberate cellobiose, while the EG enzymes act at random locations within the cellulose polymer. Together, the cellulase enzymes hydrolyze cellulose to cellobiose, which, in turn, is hydrolyzed to glucose by beta-G. In addition to the CBH, EG, and beta-G enzymes, other enzymes or proteins that enhance the enzymatic degradation of the pretreated lignocellulosic substrate may be present during the hydrolysis reaction, e.g., xylanases, beta-xylosidases, beta-mannanase, acetyl xylan esterases, ferulic acid esterases, swollenins, and expansins. The presence of xylanases may be advantageous, for example, in cases where significant amounts of xylan are present in the pretreated feedstock.

If the pentose sugars are separated from the solids between the pretreatment and enzymatic hydrolysis steps, glucose will be the main sugar monomer in the hydrolysate produced by the enzymatic treatment. If the pentose sugars released by the chemical pretreatment step are carried through to the enzymatic hydrolysis step, the hydrolysate will contain glucose and xylose in about a 2:1 weight ratio, with L-arabinose being about 3-5 wt % of the total sugar monomers. Conversion of the hexose and pentose sugars in the resulting lignocellulosic hydrolysate (sometimes referred to as a lignocellulose hydrolysate) to ethanol or another product(s) is carried out in a subsequent microbial fermentation.

If glucose is the predominant sugar present in the hydrolysate, the fermentation is typically carried out with a *Saccharomyces* spp. yeast, which converts this sugar and other hexose sugars present into ethanol. However, if the hydrolysate comprises a significant proportion of pentose sugars, such as xylose and arabinose derived from hemicellulose, the fermentation is carried out with a microbe that naturally possesses, or has been engineered to possess, the ability to ferment xylose and/or arabinose to ethanol or another product(s).

Examples of microbes that can naturally grow on and/or ferment pentose sugars, such as xylose or arabinose, to ethanol or sugar alcohols include, but are not limited to, certain species of yeasts from the genera *Candida, Pichia,* and *Kluyveromyces*. However, such yeasts typically ferment glucose at a much slower rate than *Saccharomyces*. This is a particularly significant limitation in a process for fermenting lignocellulosic hydrolysate containing large proportions of glucose and xylose.

Examples of microbes that have been genetically modified to utilize xylose for growth or fermentation include, but are not limited to, recombinant *Saccharomyces* strains into which has been inserted either (a) the xylose reductase (XR)-encoding and xylitol dehydrogenase (XDH)-encoding genes (XYL1 and XYL2, respectively) from *Pichia stipitis* (U.S. Pat. Nos. 5,789,210, 5,866,382, 6,582,944, and 7,527,927, and European Patent No. 450530) or (b) a fungal or bacterial xylose isomerase (XI) gene (U.S. Pat. Nos. 6,475,768 and 7,622,284). Such strains are able to utilize both xylose and glucose for growth and/or fermentation. Examples of yeasts that have been genetically modified to utilize L-arabinose for growth and/or fermentation include, but are not limited to, recombinant *Saccharomyces* strains into which genes from either fungal (U.S. Pat. No. 7,527,951) or bacterial (International Patent Pub. No. WO 2008/041840) arabinose metabolic pathways have been inserted. In some instances, recombinant *Saccharomyces* strains have been developed to utilize both xylose and arabinose for growth and/or fermentation (International Patent Pub. No. WO 2006/096130). Further genetic modifications to such strains have been made, by genetic engineering and/or adaptive evolution techniques, to enhance the xylose conversion rate or ethanol yield from xylose. These modifications include overexpression of sugar transporters (U.S. Patent Pub. No. 2007/0082386), deletion of endogenous nonspecific aldose reductase GRE3 (U.S. Pat. No. 6,410,302), and enhancement in the pentose phosphate pathway (International Patent Pub. No. WO 2005/108552; U.S. Patent Pub. Nos. 2006/0216804 and 2007/0082386). However, whereas the xylose conversion rates and/or yields of ethanol from xylose were increased with pure sugar fermentations, similar results were either not observed or not reported for fermentations of pentose sugars in lignocellulosic hydrolysates.

Lignocellulosic hydrolysates, regardless of whether produced by a single-step chemical treatment process or by a two-step chemical pretreatment and enzymatic hydrolysis process, typically comprise not only sugar monomers such as glucose, xylose and arabinose, but also lignin monomers, acetate (released from the hemicellulose side-chains), and chemical reaction products of the sugars, such as furfural (from xylose) and hydroxymethylfurfural (from glucose). Acetate, furfural, and hydroxymethylfurfural are well-known inhibitors of microbial growth and/or fermentation processes converting sugars to ethanol. The presence of acetic acid in lignocellulosic hydrolysates is especially problematic as it inhibits yeast cell growth and thus can significantly reduce the yield of fermentation products (Abbott et al. (2007) *FEMS Yeast Res*. 7:819-33). Other yeast inhibitors that arise when converting lignocellulosic feedstocks to fermentable sugars are furfural and 5-hydroxymethylfurfural (HMF). Furfural and HMF result from the loss of water molecules from xylose and glucose, respectively, by exposure to high temperatures and acid. The inhibitory effects of these compounds decrease the efficiency of the fermentation operations by lengthening the time required for carrying out the fermentation, increasing the amount of yeast required, decreasing the final yields, or a combination of these.

It is possible to remove these inhibitors from the lignocellulosic hydrolysate prior to their conversion to ethanol (or other chemicals) in a yeast fermentation by physical separation methods. However, these processes are often costly and are likely to result in an increase in overall costs for the production of the ethanol or other desired fermentation product(s) from the lignocellulosic biomass.

For example, one method that has been proposed to reduce the concentration of inhibitors arising from hydrolysis of lignocellulosic feedstocks is overliming, which involves the addition of $Ca(OH)_2$ to precipitate inhibitors from lignocellulosic hydrolysates, thereby improving the subsequent fermentation using yeast. Such processes are disclosed by U.S. Pat. Nos. 2,203,360; 4,342,831; 6,737,258; 7,455,997; and Wooley et al. (In: *Lignocellulosic Biomass to Ethanol Process Design and Economics Utilizing Co-Current Dilute Acid Prehydrolysis and Enzyme Hydrolysis Current and Future Scenarios* (1999) Technical Report, National Renewable Energy Laboratory, pp. 16-17). However, any handling of the lime cake is difficult and costly. In addition, the introduction of calcium into the stream increases the likelihood that calcium scale will deposit on evaporators, distillation columns, and other process equipment. The clean-up and avoidance of scale increases the cost of sugar processing.

Another method that has been proposed to remove inhibitors of fermentation is ion exchange. For example, ion exchange has been investigated by Nilvebrant et al. ((2001) *App. Biochem. Biotech.* 91-93:35-49) in which a spruce hydrolysate was treated to remove fermentation inhibitors, such as phenolic compounds, furan aldehydes, and aliphatic acids. U.S. Pat. No. 7,455,997 and Wooley et al. (supra) report the use of ion exchange to remove acetic acid from an acid-hydrolyzed mixture obtained from wood chips, followed by lime treatment. Similarly, Watson et al. ((1984) *Enzyme Microb. Technol.* 6:451-56) disclose the use of ion exchange to remove inhibitors, such as acetic acid and 2-furaldehyde (furfural), from a sugar cane bagasse acid hydrolysate prior to fermentation. Furthermore, Tran and Chambers ((1986) *Enzyme Microb. Technol.* 8:439-44) disclose various treatments to remove inhibitors prior to fermentation from an acid prehydrolysate from red oak, including mixed bed ion resin treatment.

In practice, several factors limit the effectiveness of ion exchange treatment to remove inhibitors. First, the multi-component nature of the streams results in an inefficient removal of some species at any single set of conditions. Second, the high ionic load demands very frequent and expensive regeneration of the resin. Finally, not all of the inhibitors are ionic, and ion exchange is ineffective in removing nonionic compounds from sugar.

U.S. Patent Pub. No. 2008/0171370 reports that gallic acid can be used to detoxify hydrolysates resulting from pretreating a lignocellulosic material by binding acetic acid. As disclosed therein, the gallic acid is a natural polymer comonomer, i.e., the core of the gallotannin structure, and therefore is a natural means to polymerize phenols and acetic acid in a Fischer esterification with a sulfuric acid catalyst.

International Patent Pub. No. WO 2008/124162 discloses the selective removal of acetate from a sugar mixture containing xylose and glucose by an *E. coli* strain that is able to convert acetate to a biochemical such as ethanol, butanol, succinate, lactate, fumarate, pyruvate, butyric acid, and acetone. The *E. coli* has been deleted in four genes that would otherwise code for proteins involved in xylose and glucose utilization—thereby preventing the consumption of either xylose or glucose by the *E. coli*—but that have no known effect on acetate metabolism. After acetate conversion to a biochemical, xylose and glucose fermentation are conducted on the sugar mixture using separate microorganisms, one with the ability only to ferment xylose, and the other with the ability only to ferment glucose. However, the process is not directed to removing unwanted sugars from a sugar hydrolysate, but rather to maximizing the conversion of all sugars present in the mixture to ethanol or other biochemicals.

An alternative approach to detoxification of the lignocellulosic hydrolysate is to develop yeast strains that are tolerant of the inhibitory compounds present in such hydrolysates. For example, adaptation to lignocellulose hydrolysates has been reported for *Pichia* and *Saccharomyces* strains (Huang et al. (2009) *Bioresource Technol.* 100:3914-20; Martin et al. (2007) *Bioresource Technol.* 98:1767-73). Although this approach generated strains with some tolerance to the hydrolysate, the genotype(s) of the adapted strains was not characterized.

Other attempts to characterize and/or improve tolerance to lignocellulose hydrolysates have been directed towards tolerance to the three major inhibitors in lignocellulosic hydrolysates—acetic acid, furfural, and hydroxymethylfurfural (HMF). For example, strains of *Pichia* and *Saccharomyces* have been adapted to media containing furfural and/or hydroxymethylfurfural (Liu et al. (2004) *J. Ind. Microbiol. Biotechnol.* 31:345-52; Liu et al. (2005) *Appl. Biochem. Biotechnol.* 121-124:451-60). Other studies have attempted to identify genes that contribute to inhibitor tolerance by screening collections of yeast single-deletion strains to identify those deletions that increase the sensitivity of the yeast to furfural (Gorsich et al. (2006) *Appl. Microbiol. Biotechnol.* 71:339-49), acetaldehyde (Matsufuhi et al. (2008) *Yeast* 25:825-22), and lactic and acetic acids (Kawahata et al. (2006) *FEMS Yeast Research* 6:924-36). Expression profiling of a limited set of genes was conducted to determine changes in gene expression in a yeast strain adapted to furfural and HMF vs. a parental strain cultured in the presence of HMF (Liu et al. (2009) *Mol. Genet. Genomics* 282:233-44). However, neither the sensitivity of the resulting strains to, nor the expression profile of the strains cultured in the presence of, lignocellulose hydrolysates was reported.

SUMMARY OF THE INVENTION

It is an object of the present invention to provide yeast strains with enhanced ability to utilize the xylose present in a lignocellulosic hydrolysate for growth and/or fermentation to ethanol or other fermentation product(s).

The present invention provides a modified yeast strain capable of utilizing xylose and/or other pentose sugars present in a lignocellulosic hydrolysate for growth and/or fermentation of such pentose sugars to a fermentation product (e.g., an alcohol (e.g., ethanol) or a sugar alcohol (e.g., xylitol)). The modified yeast strain exhibits an increase in growth rate of at least 1.3-fold (e.g., 1.5-fold, 2-fold, or greater) in the specific rate of xylose fermentation relative to a corresponding parental yeast strain from which the modified yeast strain is derived. The isolated, modified yeast strain may be *Saccharomyces*, or may be some other genus of yeast.

In an aspect of the invention, the modified strain comprises, relative to a parental strain from which it is derived, (a) an increase in copy number or expression (e.g., copy number and/or expression) of one or more genes selected from the group consisting of ARE1, VBA3, RNQ1, FUS1, PDI1, BUD23, IMG1, DDI2, SNO3, SNZ3, YCL042W, YCL073C, YCR045C, and tE(UUC)B (and in some additional embodiments, BIK1 and GLK1), and/or (b) a decrease in copy number or expression (e.g., copy number and/or expression) of one or more genes selected from the group consisting of ALD2, SSA2, MST27, PRM8, ERV14, ECM21, ILS1, PRP6, YBL100W-C, YBR201C-A, and tE(UUC)G2 (and in some additional embodiments, ALD3).

In another aspect of the invention, the modified strain comprises, relative to a parental strain from which it is derived, (a) an increase in copy number and/or expression of one or more genes of the galactose metabolic pathway selected from the group consisting of GAL1, GAL7, GAL10, GAL80, and PGM1, and/or (b) a decrease in the copy number and/or expression of one or more genes of the galactose metabolic pathway selected from the group consisting of GAL3, GAL4, GAL11, and PGM2.

In yet another aspect of the invention, the modified strain comprises, relative to a parental strain from which it is derived, (a) an increase in copy number and/or expression of one or more genes involved in hexose transport selected from the group consisting of HXT1, HXT2, HXT3, GAL2, HXK2, and GRR1, and/or (b) a decrease in copy number and/or expression of one or more genes involved in hexose transport selected from the group consisting of HXT4, HXT5, HXT6, HXT7, HXT9, HXT11, HXT12, SNF3, RTG2, and REG1.

In still another aspect of the invention, the modified strain comprises, relative to a parental strain from which it is derived, an increase in copy number and/or expression of one or more genes of the ergosterol biosynthetic pathway selected from the group consisting of ERG1, ERG8, ERG10, ERG10, ERG20, ERG25, ERG26, ERG27, HMG1, and CYB5 (and, in some additional embodiments, ERG2, ERG3, ERG4, ERG5, ERG24, and ERG28).

For the purposes of the invention described herein, the modified yeast strain is identical to the parental yeast strain except for (a) an increase in copy number and/or expression of one or more genes selected from the group consisting of ARE1, VBA3, RNQ1, FUS1, PDI1, BUD23, IMG1, DDI2, SNO3, SNZ3, YCL042W, YCL073C, YCR045C, tE(UUC)B, GAL1, GAL7, GAL10, GAL80, PGM1, HXT1, HXT2, HXT3, GAL2, HXK2, GRR1, ERG1, ERG8, ERG10, ERG11, ERG20, ERG25, ERG26, ERG27, HMG1, and CYB5 (and, in some additional embodiments, BIK1, GLK1, ERG2, ERG3, ERG4, ERG5, ERG24, and ERG28), and/or (b) a decrease in copy number and/or expression of one or more genes selected from the group consisting of ALD2, SSA2, MST27, PRM8, ERV14, ECM21, ILS1, PRP6, YBL100W-C, YBR201C-A, tE(UUC)G2, GAL3, GAL4, GAL11, PGM2, HXT4, HXT5, HXT6, HXT7, HXT9, HXT11, HXT12, SNF3, RTG2, and REG1 (and in some additional embodiments, ALD3).

The modified yeast strain may be derived from a parental yeast strain that is naturally capable of glucose fermentation, e.g., a species of *Saccharomyces*. In some embodiments, the modified yeast strain is capable of fermenting both the glucose and xylose present in lignocellulose hydrolysates. The modified yeast strain may also be derived from a parental yeast strain that is naturally capable of xylose fermentation, e.g., a species of *Candida*, *Pichia*, or *Kluyveromyces*, or one that has been modified for enhanced xylose utilization through recombinant or nonrecombinant means.

The modified yeast strain may be derived from a parental strain of *Saccharomyces* that has been made capable of utilizing xylose for growth or fermentation by incorporation of (a) genes encoding xylose reductase (XR) and xylitol dehydrogenase (XDH) and/or (b) gene(s) encoding one or more xylose isomerase (XI). In addition, the modified yeast strain may also overexpress an endogenous or heterologous gene encoding xylulokinase. Alternatively, the modified yeast strain may be derived from a parental strain of *Saccharomyces* that has been made capable of utilizing xylose for growth or fermentation by one or more nonrecombinant methods, such as adaptive evolution or random mutagenesis and selection. The practice of the invention is not limited by the means used to produce the modified yeast strain and/or the parental yeast strain.

The modified yeast strain may comprise other modifications that enable enhanced fermentation of xylose or other sugars present in lignocellulose hydrolysates, including but not limited to, altered expression of one or more genes encoding enzymes of the pentose phosphate pathway (PPP), decreased expression of one or more genes encoding nonspecific aldose reductase(s), or expression of one or more gene encoding enzymes enabling fermentation of L-arabinose or other hexose or pentose sugars present in lignocellulose hydrolysates (e.g., mannose, galactose, and fucose). In some embodiments, these same other modifications are also present in the parental yeast strain. Thus, these other modifications may be introduced to the parental yeast strain before, during, or after the modifications provided by the present invention.

One modified yeast strain of the present invention, *S. cerevisiae* Y108-1, has been deposited with the American Type Culture Collection (ATCC®), 10801 University Boulevard, Manassas, Va. 20110-2209. The deposit was made on Jan. 6, 2010, and was assigned ATCC Deposit No. PTA-10567.

The present invention also relates to a process for producing a fermentation product (e.g., an alcohol (e.g., ethanol) or a sugar alcohol (e.g., xylitol)) from a lignocellulosic hydrolysate comprising from about 30 wt % to about 90 wt % xylose (as a function of the weight of total carbohydrate) utilizing the modified yeast strain as described herein. In addition, the present invention contemplates the lignocellulosic hydrolysate containing some percentage(s) of at least one inhibitor of yeast growth or fermentation (e.g., acetic acid, furfural, HMF) as a function of the total dissolved solids in the hydrolysate. In the fermentation process of the present invention, a modified yeast strain as described above is cultured (e.g., cultured anaerobically) in a fermentation medium comprising the lignocellulosic hydrolysate under conditions that facilitate the conversion of the xylose in the hydrolysate to the fermentation product.

linked to the ADH1 promoter (Padh), the *P. stipitis* XYL2 gene encoding xylitol dehydrogenase (XDH) linked to the pyruvate kinase promoter (Ppyk) and the *S. cerevisiae* gene encoding xylulose kinase (XKS1) linked to the pyruvate kinase promoter (Ppyk). Other elements include antibiotic selection markers (KanR and AmpR), *S. cerevisiae* 5S ribosomal DNA targeting sequences (5S rDNA) and an autonomously replicating sequence (ARS).

Figure 16:
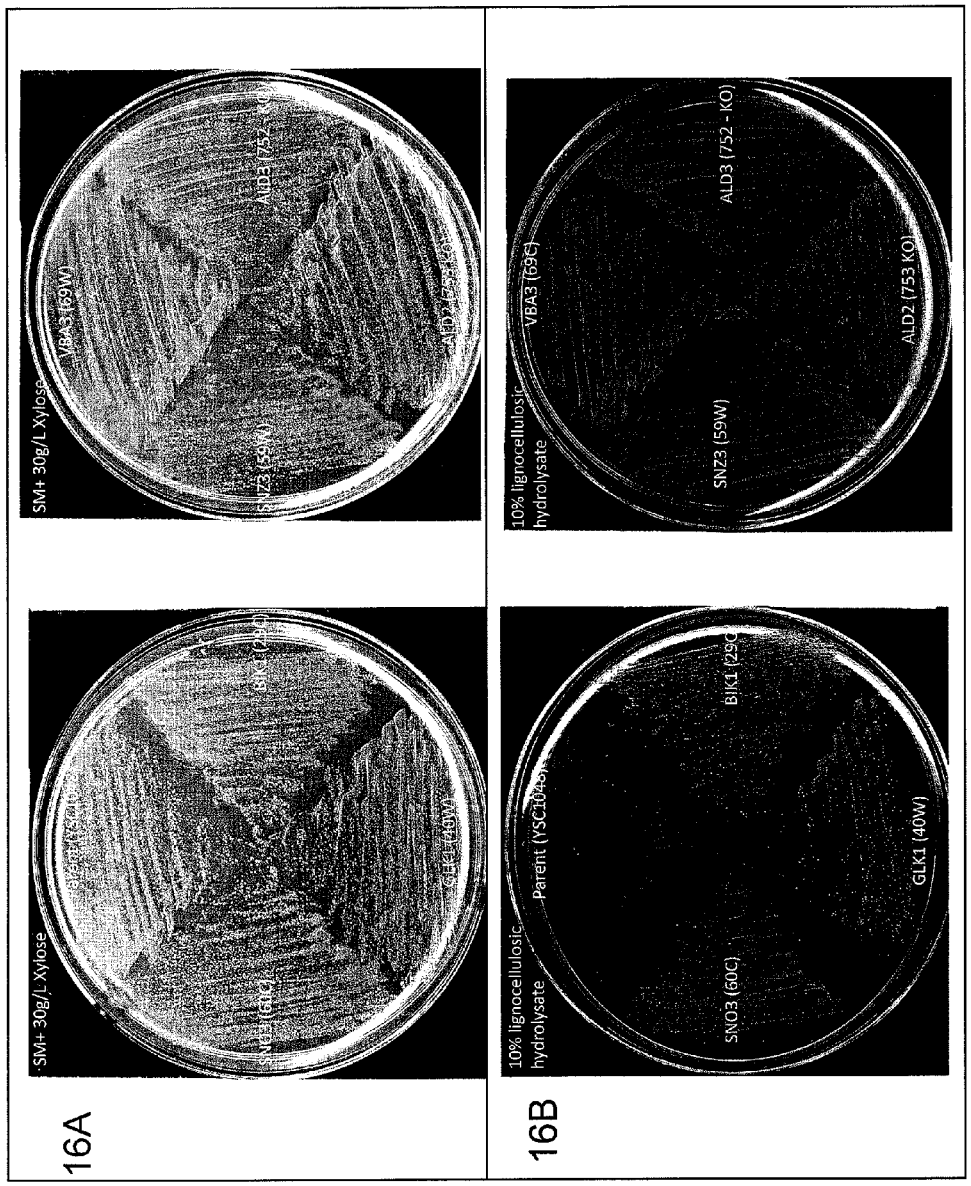

FIG. 16 presents the comparative growth of a control parental (strain YSC1048) and modified yeast strains overexpressing (+) or deleted in (Δ) the genes shown on (FIG. 16A) synthetic media (SM)+30 g/L xylose plates and (FIG. 16B) media containing dilute, glucose-depleted lignocellulose hydrolysate (10% lignocellulosic hydrolysate). Plates were incubated at 30° C. for five days.

Figure 17:
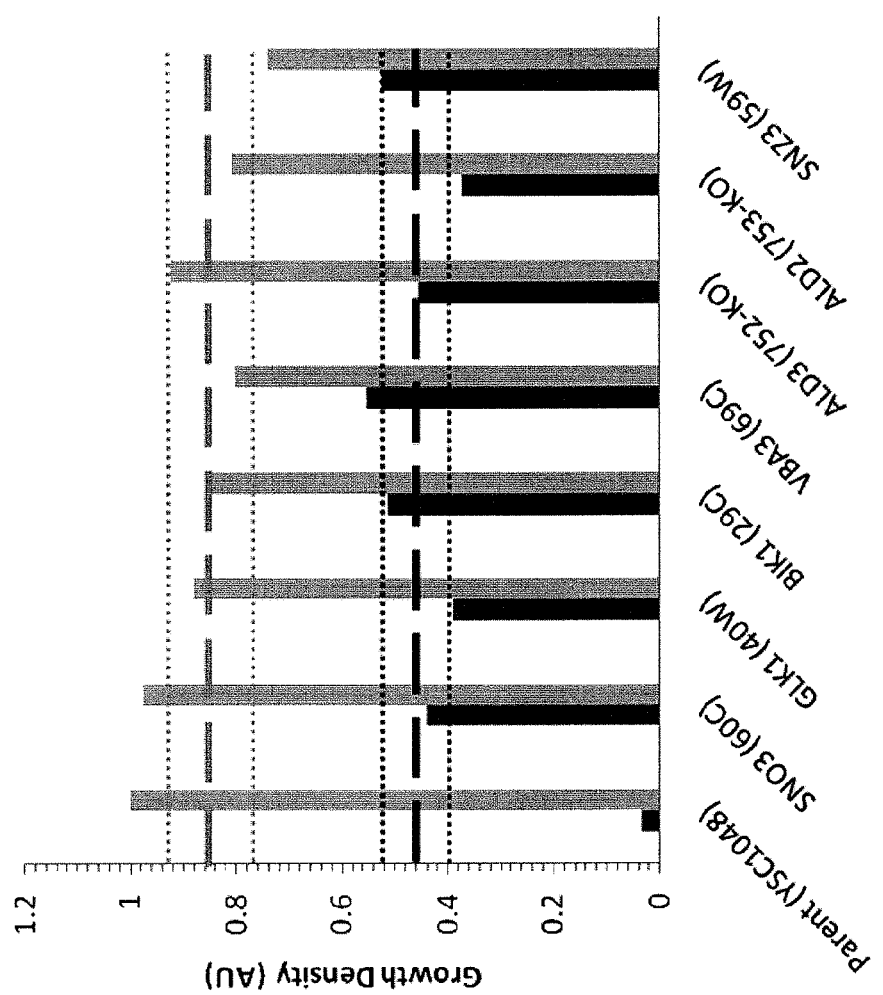

FIG. 17 presents the relative growth density on synthetic media+30 g/L xylose (light grey) or glucose-depleted dilute lignocellulosic hydrolysate plates (dark grey) of parental and modified yeast strains containing the plasmid pLNH-ST. Plates were imaged and relative density was measured with ImageJ software. Dashed lines indicate the average growth density of the modified yeast strains only. Dotted lines illustrate standard deviation of the mean.

Figure 18:
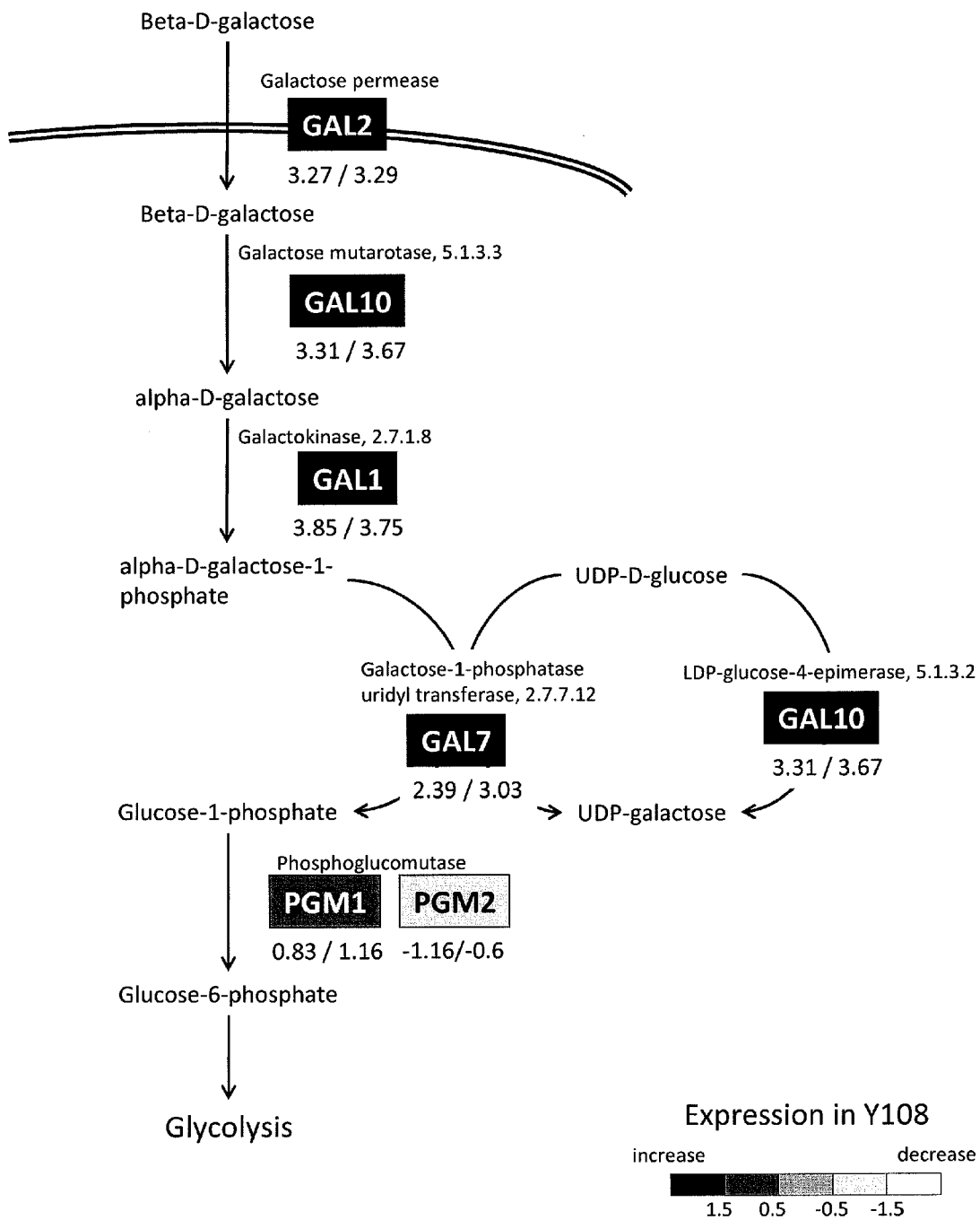

FIG. 18 presents the relative transcript level of genes involved in the galactose metabolic pathway in the modified (Y108-1) vs. the parental (LNH-ST) yeast strain.

Figure 19A:
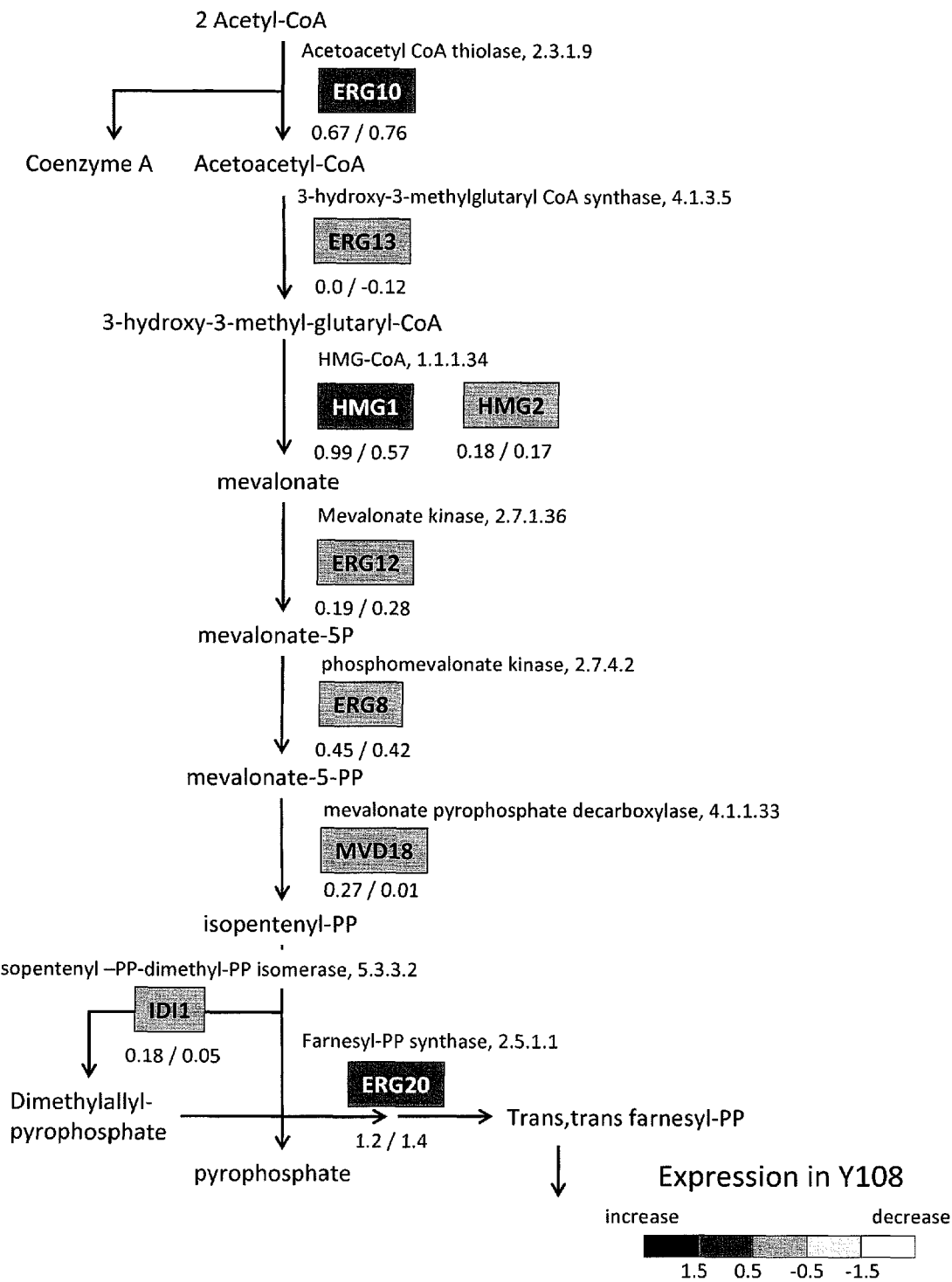
Figure 19B:
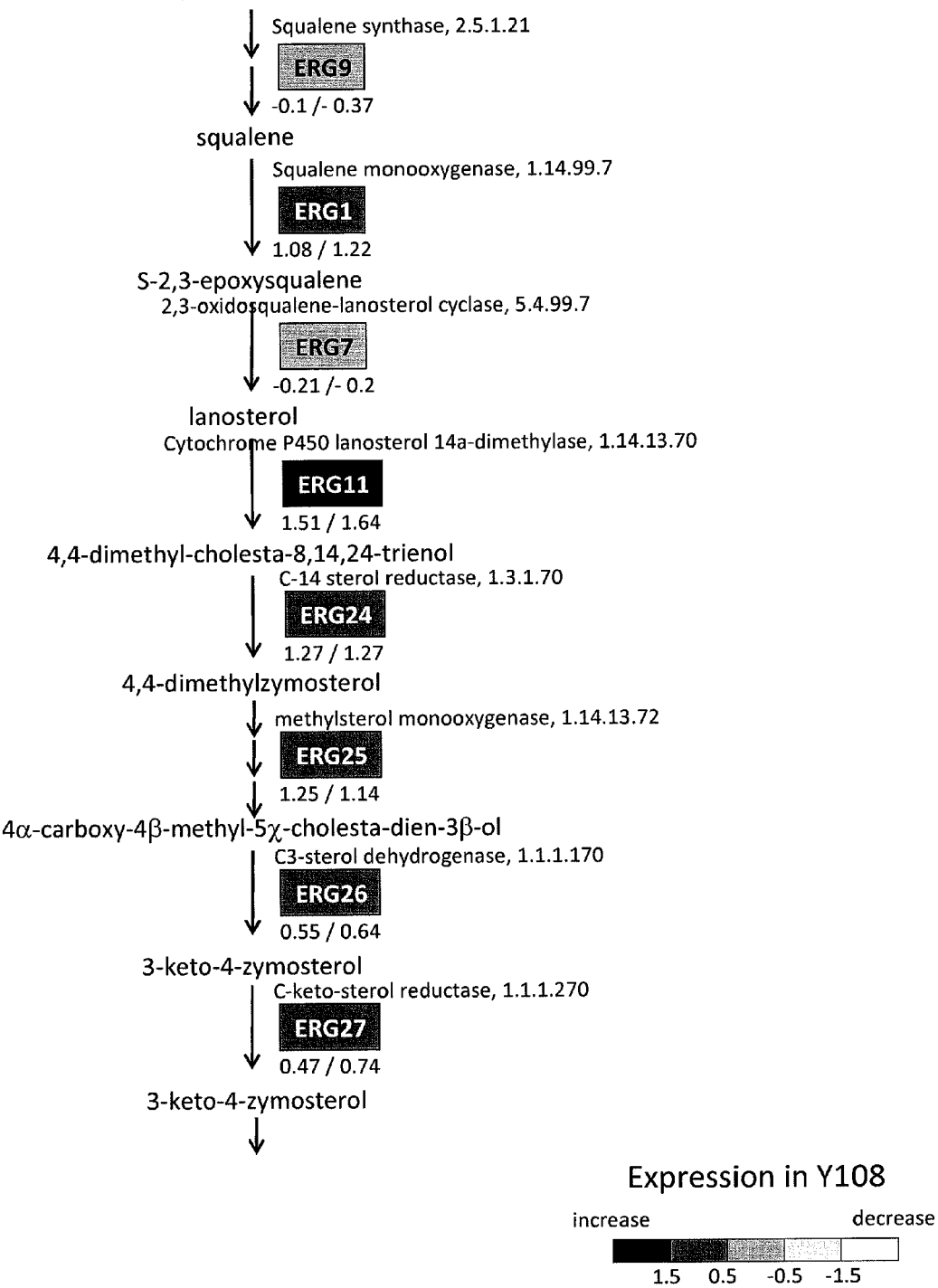
Figure 19C:
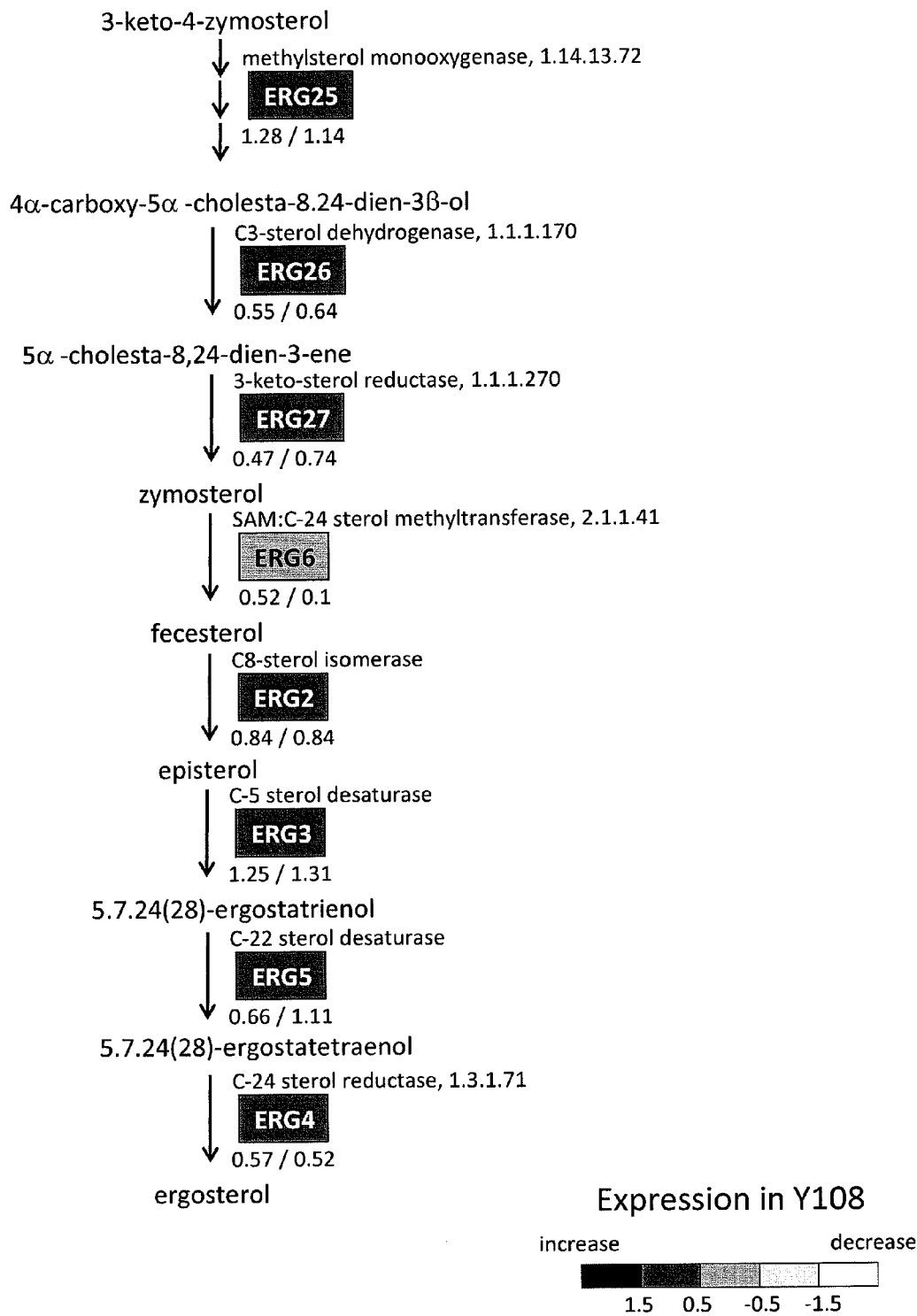

FIGS. 19A, 19B, and 19C present the relative transcript level of genes involved in the ergosterol biosynthetic pathway in the modified (Y108-1) vs. the parental (LNH-ST) yeast strain.

DETAILED DESCRIPTION OF THE INVENTION

The following description is of an embodiment by way of example only and without limitation to the combination of features necessary for carrying the invention into effect. The headings provided are not meant to be limiting of the various embodiments of the invention. Terms such as "comprises," "comprising," "comprise," "includes," "including," and "include" are not meant to be limiting. In addition, the use of the singular includes the plural, and "or" means "and/or" unless otherwise stated. Unless otherwise defined herein, all technical and scientific terms used herein have the same meaning as commonly understood by one of ordinary skill in the art.

Modulation of Genetic Profiles in Modified Yeast Strains

As used herein, a modified yeast strain is a strain that exhibits a change (i.e., an increase or decrease) in copy number or expression of the identified gene(s) relative to the copy number or expression of the same gene(s) in a parental strain from which it is derived.

A parental yeast strain is a strain that is capable of xylose fermentation, either naturally or as the result of mutagenesis, but which exhibits wild-type or native copy number or expression of the identified genes that are increased or decreased in copy number or expression in the modified yeast strain.

The modified yeast strain may be derived from a parental yeast strain of *Saccharomyces* that has been made capable of xylose fermentation by recombinant incorporation of (a) genes encoding xylose reductase (XR) and xylitol dehydrogenase (XDH) and/or (b) gene(s) encoding one or more xylose isomerase (XI). In addition, the modified yeast strain may also overexpress an endogenous or heterologous gene encoding xylulokinase (XK). One such *Saccharomyces* strain that expresses the XR and XDH encoding genes from *Pichia stipitis* and overexpresses the endogenous XK encoding gene is *Saccharomyces* strain LNH-ST (described in U.S. Pat. No. 7,527,927).

Alternatively, the modified yeast strain may be derived from a parental strain of *Saccharomyces* that has been made capable of xylose fermentation by one or more nonrecombinant techniques, such as adaptive evolution or random mutagenesis and selection. However, it should be appreciated that the practice of the invention is not limited by the means used to produce the parental and modified yeast strains.

The modified yeast strain may also be derived from a parental strain of *Candida, Pichia*, or *Kluyveromyces* that is naturally capable of xylose fermentation, or one that has been modified for enhanced xylose fermentation through recombinant or nonrecombinant means.

For the purposes described herein, the term "increased copy number" means at least one extra copy of at least the coding region of a given gene is present in the modified yeast as compared to the number of copies of the same gene in the parental yeast. For example, the modified yeast strain may contain 1, 2, 3, 4, 5, 10, or more extra copies of at least the coding region of a given gene relative to the number of copies of that same gene in the parental yeast strain. The extra copies of a given gene may be integrated into the genome of the modified yeast strain or may be present on one or more autonomously replicating vectors or plasmids present in the modified yeast strain.

For the purposes described herein, the term "increased expression" means at least about a 1.3-fold increase in the level of transcript for a given gene in the modified yeast as compared to the level of transcript for the same gene in the parental yeast, when grown under identical or nearly identical conditions of medium composition, temperature, pH, cell density, and age of culture. For example, the transcript level of a given gene in the modified yeast can be increased by at least 1.3-, 1.5-, 2.0-, 2.5-, 3.0-, 4.0-, 5.0-, or 10-fold, or more, relative to the transcript level of the same gene in the parental yeast when grown or cultured under essentially the same culture conditions.

For the purposes described herein, the term "decreased copy number" means at least one less copy of at least the coding region of a given gene is present in the genome of the modified yeast as compared to the copy number of the same gene present in the parental yeast.

For the purposes described herein, the term "decreased expression" means at least about a 2-fold decrease in the level of transcript for a given gene in the modified yeast as compared to the level of transcript for the same gene in the parental yeast when grown under identical or nearly identical conditions of medium composition, temperature, pH, cell density, and age of culture. For example, the level of transcript of a given gene in the modified yeast strain may be decreased by 2-, 2.5-, 3-, 5-, 10-, 20-, 50-fold or more relative to the level of transcript of that same gene in the parental yeast strain when grown or cultured under essentially the same culture conditions.

In at least some embodiments of the present invention, the increase or decrease in copy number or expression of the identified gene(s) in a modified yeast strain can be produced by any of various random mutagenesis and selection techniques. For example, the parental yeast strain may be subjected to irradiation or chemical mutagenesis to create a library of mutated strains, which are then screened for the desired altered phenotype; in the present case, that phenotype would include the ability to utilize more efficiently the xylose component of a lignocellulosic hydrolysate for growth and/or fermentation. Random mutagenesis and selection techniques also include "adaptive evolution techniques" or "evolutionary engineering techniques." As used herein, the term adaptive evolution technique refers to any method or procedure employed to influence the phenotype and genetic profile of a yeast strain or organism through the use of exposure to environmental challenges, and subsequent selection of the modified and/or improved yeast strain with the desired altered phenotype and corresponding altered genetic profile. For example, a parental yeast strain may be cultured in media containing initially low, then increasing, concentrations of lignocellulosic hydrolysate to generate a population of yeast cells with the ability to utilize the xylose component in the hydrolysate for growth or fermentation, from which individual modified yeast strains may be isolated, as described in Example 1.

In at least some embodiments of the present invention, the increase or decrease in copy number or expression of the identified genes in the modified yeast strain can be produced by any of various genetic engineering techniques. As used herein, the term genetic engineering technique refers to any of several well-known techniques for the direct manipulation of an organism's genes. For example, gene knockout (insertion of an inoperative DNA sequence, often replacing the endogenous operative sequence, into an organism's chromosome), gene knock-in (insertion of a protein-coding DNA sequence into an organism's chromosome), and gene knockdown (insertion of DNA sequences that encode antisense RNA or small interfering RNA, i.e., RNA interference (RNAi)) techniques are well known in the art.

Methods for reducing gene expression are well known and can be performed using any of a variety of methods known in the art. For example, the gene can be modified to disrupt a transcription or translation initiation sequence or to introduce a frameshift mutation in the transcript encoding the polypeptide. Other methods of reducing the gene expression include post-transcriptional RNA silencing methodologies such as antisense RNA and RNA interference (RNAi). Antisense techniques involve introducing a nucleotide sequence complementary to the transcript of a target gene such that the complementary antisense nucleotide sequence hybridizes to the target gene transcript, thus reducing or eliminating the number of transcripts available to be translated into protein. Examples of expressing an antisense RNA are shown in Ngiam et al. (2000) *Appl. Environ. Microbiol.* 66(2):775-82; and Zrenner et al. (1993) *Planta.* 190(2):247-52, each of which is hereby incorporated by reference herein in its entirety. RNAi methodologies include double stranded RNA (dsRNA), short hairpin RNAs (shRNAs), and small interfering RNAs (siRNAs) as known to one of skill in the art, for example, the techniques of Fire et al. (1998) *Nature* 391:806-11; Paddison et al. (2002) *Genes Dev.* 16:948-58; and Miyagishi et al. (2002) *Nat. Biotechnol.* 20:497-500. The content of each of the above-cited references is incorporated by reference herein in its entirety.

Methods for decreasing the expression of a gene also include partial or complete deletion of the gene, and disruption or replacement of the promoter of the gene such that transcription of the gene is greatly reduced or even inhibited. For example, the promoter of the gene can be replaced with a weak promoter, as exemplified by U.S. Pat. No. 6,933,133, which is incorporated by reference herein in its entirety. Thus, where the weak promoter is operably linked with the coding sequence of an endogenous polypeptide, transcription of that gene will be greatly reduced or even inhibited.

In some embodiments, the modified yeast strain has been genetically modified to at least partially delete one or more of the identified gene(s). As used herein, a gene deletion or deletion mutation is a mutation in which part of a sequence of the DNA making up the gene is missing. Thus, a deletion is a loss or replacement of genetic material resulting in a complete or partial disruption of the sequence of the DNA making up the gene. Any number of nucleotides can be deleted, from a single base to an entire piece of a chromosome. In some embodiments, complete or near-complete deletion of the gene sequence is contemplated. For example, deletion in a gene may be a deletion of at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of the gene.

In the methods of the present invention, the modified yeast strains of the invention exhibit increased growth and/or at least a 1.3-fold (e.g., 1.5-fold, 2-fold, or greater) increase in the specific rate of xylose fermentation, relative to a corresponding parental yeast strain from which the modified yeast strain is derived, in lignocellulosic hydrolysates.

Sets of Genes Modulated in Modified Yeast Strains

Modified yeast strains of the present invention can exhibit enhanced fermentation and/or growth on pentose sugars, such as xylose, in lignocellulosic hydrolysate. The modified yeast strain may be a strain of *Saccharomyces* or another yeast genus. In at least one embodiment, the modified strain is derived from a parental *S. cerevisiae* strain with genetic modifications inserting the *P. stipitis* XYL1 (XR) and XYL2 (XDH) genes (e.g., LNH-ST). In another embodiment, the modified yeast strain may be *S. cerevisiae* strain Y108-1 (ATCC Deposit No. PTA-10567).

The modifications of the present invention (as produced by the adaptive evolution of the parent yeast strain) increased the rate of growth on, or fermentation of, xylose in lignocellulosic hydrolysate above the rate seen in the parental strain.

In addition, the modified yeast strains of the present invention may also reduce the levels of the inhibitory compounds furfural and HMF present in lignocellulosic hydrolysates.

The modified yeast strain (e.g., Y108-1) can comprise increases or decreases in the copy number or expression of one or more genes, and the enhanced fermentation rates for pentose sugars (e.g., xylose) can be the result of these modulations, for example, in the levels of transcription, translation, and activity associated with the genes or their encoded proteins.

In the yeast strains studied here, sixteen genes exhibited increases in copy number in the modified yeast strain relative to the parental yeast strain: ARE1, VBA3, BIK1, RNQ1, FUS1, PDI1, BUD23, IMG1, DDI2, SNO3, SNZ3, YCL042W, YCL073C, YCR045C, tE(UUC)B, and GLK1. Another twenty-seven exhibited increased expression in the modified yeast strain relative to the parental yeast strain when cultured using lignocellulose hydrolysate as a carbon source: HXK2, GRR1, GAL1, GAL7, GAL10, GAL80, PGM1, HXT1, HXT2, HXT3, GAL2, ERG1, ERG2, ERG3, ERG4, ERG5, ERG8, ERG10, ERG11, ERG20, ERG24, ERG25, ERG26, ERG27, ERG28, HMG1, and CYB5. The increase in copy number and expression of these 43 genes can be linked to the enhanced growth or an increase rate of fermentation of the xylose in lignocellulose hydrolysates exhibited by the modified yeast strain, either directly or indirectly (see Table 1 and Examples 2, 3.2, 4.2, and 4.3).

Liu et al. ((2009) *Mol. Genet. Genomics* 282:233-44) disclose differences in gene expression between lignocellulose hydrolysate-tolerant and -sensitive strains after growth in the presence of HMF and furfural. Among the genes exhibiting higher levels of mRNA in the tolerant strain are GLK1 and ALD2; the former is noted in the present disclosure (above) as elevated in the modified strain (Y108-1), which is capable of enhanced fermentation of xylose. Interestingly, ALD2 is noted in the present disclosure (above) as decreased in copy number in the modified strain; however, Liu et al. were not studying differences in gene expression related to xylose fermentation. Similarly, Gorsich et al. ((2006) *Appl. Microbiol. Biotechnol.* 71:339-49) disclosed that a deletion of the ERG3 gene reduced the growth of yeast in the presence of furfural, Matsufuji et al. ((2008) *Yeast* 25:825-33) disclosed that a deletion in the ALD3 gene conferred increased sensitivity to acetaldehyde, and Kawahata et al. ((2006) *FEMS Yeast Res.* 6:924-36) disclosed that single deletions of the ERG2, ERG3, ERG4, ERG5, ERG6, ERG24, and ERG28 genes led to increased sensitivity of the yeast strains to organic acids. Interestingly, although Kawahata et al. disclosed that a deletion in the ERV14 gene also increased sensitivity to organic acids, a decrease in ERV14 expression in the modified yeast of the present invention resulted in improved fermentation of lignocellulose hydrolysate.

The present invention contemplates the sets of genes that contribute to producing an enhanced rate of fermentation of a pentose sugar, e.g., xylose, in lignocellulosic hydrolysate to include one or more of the 43 genes identified as having increased copy numbers or expression (wherein BIK1, GLK1, ERG2, ERG3, ERG4, ERG5, ERG24, and ERG28 are included in sets containing at least one other of the identified genes). The sets can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 or all 43 of the identified genes.

In the yeast strains studied here, twelve genes exhibited decreases in copy number in the modified strain relative to the parental strain: ALD2, SSA2, MST27, PRM8, ERV14, ECM21, ILS1, PRP6, YBL100W-C, YBR201C-A, ALD3, and tE(UUC)G2. Another fourteen genes exhibited decreased expression in the modified yeast strain relative to the parental yeast strain when cultured using lignocellulose hydrolysate as a carbon source: GAL3, GAL4, GAL11, PGM2, HXT4, HXT5, HXT6, HXT7, HXT9, HXT11, HXT12, SNF3, RTG2, and REG1. The decrease in copy number and expression of these 26 genes can be linked to the enhanced growth, or an increased rate of fermentation of the xylose, in lignocellulose hydrolysates exhibited by the modified yeast strain, either directly or indirectly (see Table 1 and Examples 2, 3.2, 4.2 and 4.3).

The present invention contemplates the sets of genes that contribute to producing an enhanced rate of fermentation of a pentose sugar, e.g., xylose, in lignocellulosic hydrolysate to include one or more of the twenty-six genes identified as having decreased copy numbers or expression. The sets can include 1, 2, 3, 4, 5, 6, 7, 8, 9, 10, 11, 12, 13, 14, 15, 16, 17, 18, 19, 20, 21, 22, 23, 24, 25 or all 26 of the identified genes exhibiting decreased copy number or expression.

The present invention further contemplates the sets of genes that contribute to producing an enhanced rate of fermentation of a pentose sugar, e.g., xylose, in lignocellulosic hydrolysate to include any combination of one or more of the 47 genes identified as having increased copy numbers or expression and one or more of the 26 genes identified as having decreased copy numbers or expression. These combined sets can include modulations of from 2 to 73 of the identified genes.

Further information regarding the individual genes whose copy number and/or expression is increased or decreased in the present invention is known and readily available to one of ordinary skill in the art. For example, wild-type or native sequences of the individual genes exhibiting changes in copy number or expression in the modified yeast strains of the present invention can be obtained from publicly available sources including, but not limited to, the *Saccharomyces* Genome Database (SGD™; located on the web at www.yeastgenome.org); the *Pichia stipitis* webpage at the NCBI Entrez Genome Project website (located at www.ncbi.nlm.nih.gov/sites/entrez?db=genomeprj&cmd=Retrieve&dopt=Overview& list_uids=12845); and the *Kluyveromyces lactis* webpage at the EMBL-EBI Eukaryotes Genomes website (located at www.ebi.ac.uk/2 can/genomes/eukaryotes/Kluyveromyces_lactis.html).

The modulation of copy numbers of genes can be measured by one of ordinary skill in the art through well-known means, for example, comparative genomic hybridization (CGH), Southern blot hybridization, or quantitative real-time PCR (qRT-PCR) from genomic DNA. A CGH method is provided in Example 3.2.

The modulation of expression of genes also can be measured by one of ordinary skill in the art through analysis of selected mRNA or transcript levels by well-known means, for example, quantitative real-time PCR (qRT-PCR) as described in Example 4.3, Northern blot hybridization, or global gene expression profiling using cDNA or oligo array hybridization, as described in Example 4.2.

Figure 15:
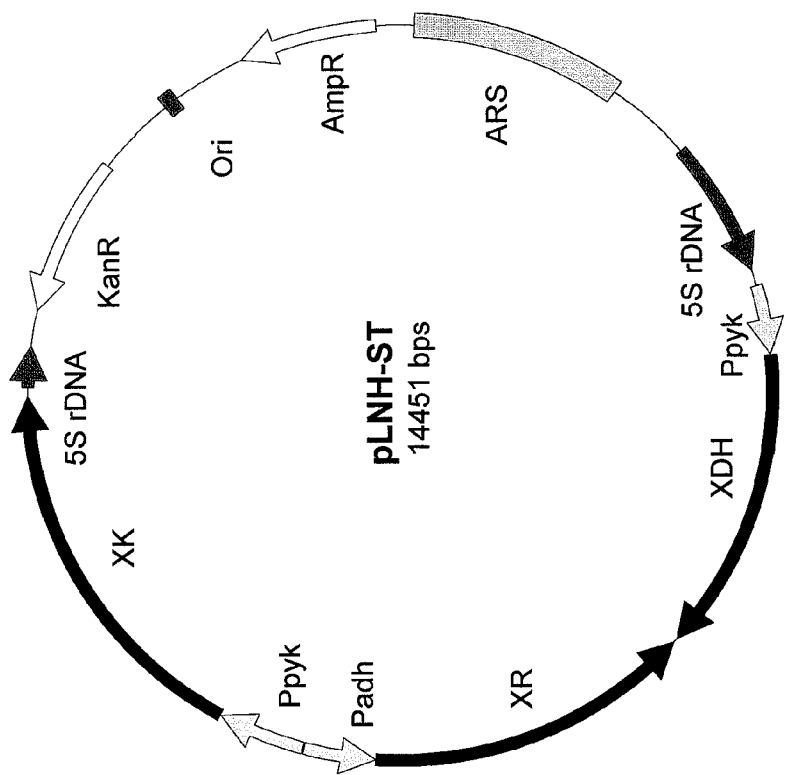
FIG. 15 presents a map of the plasmid pLNH-ST comprising the *P. stipitis* XYL1 gene encoding xylose-reductase (XR)

In at least one modified yeast strain, the parental *Saccharomyces* strain has been genetically engineered or modified by insertion of one or more copies of the *Pichia stipitis* XYL1 (encoding xylose reductase or "XR") and XYL2 (encoding xylitol dehydrogenase or "XDH") into the genome of a *Saccharomyces* strain. The modified yeast strain of the present invention exhibits an apparent further increase in the number of copies and expression of the XR- and XDH-encoding genes. The ADH1 and CDC19 promoter sequences associated with the XR and XDH genes (as shown in the map of plasmid pLNH-ST in FIG. 15) also exhibited an increase in copy number (copy numbers of XR and XDH genes were not directly analyzed as they are not part of the native *S. cerevisiae* genome and therefore probes for these genes were not present on the commercial oligonucleotide arrays used to determine gene copy number). This is consistent with the detection of increased transcript levels and enzymatic activity for XR and XDH in the modified yeast strain relative to the parental yeast strain (Examples 4.3 and 5, FIGS. 8 and 9)

One method of increasing the rate of pentose sugar fermentation (e.g., xylose fermentation to ethanol) is decreasing the inhibitory effects of certain aromatic aldehydes, such as furfural. At least one study (Almeida et al. (2008) *Biotechnol. Biofuels* 1:12; see also Almeida et al. (2008) *Appl. Microbiol. Biotechnol.* 78:939-45) disclosed that the NADH cofactor produced by the activity of XDH is required for detoxification of furfural and HMF. Thus, increased activity of XDH, as is supported by the increased copy number for its promoter, can lead to elevated levels of NADH and subsequent increased detoxification of furfural (Modig et al. (2002) *Biochem. J.* 363:769-76). Detoxification of that inhibitor in lignocellulosic hydrolysate would produce an increase in xylose fermentation.

TABLE 1

Genes Exhibiting Increased or Decreased Copy Number and/or Expression in Modified Yeast Strains Relative to Parental Strain. Systematic Name, Standard Name, and Description are taken from the *Saccharomyces* Genome Database (see URL: yeastgenome.org).

| Systematic Name | Standard Name | Description |
| --- | --- | --- |
| YGR194C | XKS1 | Xylulokinase, converts D-xylulose and ATP to xylulose 5-phosphate and ADP; rate limiting step in fermentation of xylulose; required for xylose fermentation by recombinant *S. cerevisiae* strains |
| tE(UUC)B | | tRNA-Glu; thiolation of uridine at wobble position (34) requires Ncs6p |
| YCL029C | BIK1 | Microtubule-associated protein, component of the interface between microtubules and kinetochore, involved in sister chromatid separation; essential in polyploid cells but not in haploid or diploid cells; ortholog of mammalian CLIP-170 |
| YCL028W | RNQ1 | [PIN(+)] prion, an infectious protein conformation that is generally an ordered protein aggregate |
| YCL027W | FUS1 | Membrane protein localized to the shmoo tip, required for cell fusion; expression regulated by mating pheromone; proposed to coordinate signaling, fusion, and polarization events required for fusion; potential Cdc28p substrate |
| YCL043C | PDI1 | Protein disulfide isomerase, multifunctional protein resident in the endoplasmic reticulum lumen, essential for the formation of disulfide bonds in secretory and cell-surface proteins, unscrambles nonnative disulfide bonds |
| YCL042W | | Putative protein of unknown function; epitope-tagged protein localizes to the cytoplasm |
| YCL040W | GLK1 | Glucokinase, catalyzes the phosphorylation of glucose at C6 in the first irreversible step of glucose metabolism; one of three glucose phosphorylating enzymes; expression regulated by nonfermentable carbon sources |
| YCR045C | — | Putative protein of unknown function; nonessential gene identified in a screen for mutants with decreased levels of rDNA transcription |
| YCR046C | IMG1 | Mitochondrial ribosomal protein of the large subunit, required for respiration and for maintenance of the mitochondrial genome |
| YCR047C | BUD23 | Methyltransferase, methylates residue G1575 of 18S rRNA; required for rRNA processing and nuclear export of 40S ribosomal subunits independently of methylation activity; diploid mutant displays random budding pattern |
| YCR048W | ARE1 | Acyl-CoA:sterol acyltransferase, isozyme of Are2p; endoplasmic reticulum enzyme that contributes the major sterol esterification activity in the absence of oxygen |
| YCL1073C | | Protein of unconfirmed function; displays a topology characteristic of the Major Facilitators Superfamily of membrane proteins; coding sequence 98% identical to that of YKR106W |
| YCL069W | VBA3 | Permease of basic amino acids in the vacuolar membrane |
| YFL061W | DDI2 | Protein of unknown function; expression is induced over 100-fold by DNA damage; induction decreased in rad6 and rad18 mutants |
| YFL060C | SNO3 | Protein of unknown function, nearly identical to Sno2p; expression is induced before the diauxic shift and also in the absence of thiamin |
| YFL059W | SNZ3 | Member of a stationary phase-induced gene family; transcription of SNZ2 is induced prior to diauxic shift, and also in the absence of thiamin in a Thi2p-dependent manner; forms a coregulated gene pair with SNO3 |
| YBL101C | ECM21 | Protein involved in regulating the endocytosis of plasma membrane proteins; identified as a substrate for ubiquitination by Rsp5p and deubiquitination by Ubp2p; promoter contains several Gcn4p binding elements |
| YBL076C | ILS1 | Cytoplasmic isoleucine-tRNA synthetase, target of the G1-specific inhibitor reveromycin A |
| YBL100W-C | | Putative protein of unknown function |
| YBR055C | PRP6 | Splicing factor, component of the U4/U6-U5 snRNP complex |
| YGL054C | ERV14 | Protein localized to COPII-coated vesicles, involved in vesicle formation and incorporation of specific secretory cargo; required for the delivery of bud-site selection protein Axl2p to cell surface; related to Drosophila cornichon |
| tE(UUC)G2 | tE(UUC)G2 | tRNA-Glu; thiolation of uridine at wobble position (34) requires Ncs6p |

TABLE 1-continued

Genes Exhibiting Increased or Decreased Copy Number and/or Expression in Modified Yeast Strains Relative to Parental Strain. Systematic Name, Standard Name, and Description are taken from the *Saccharomyces* Genome Database (see URL: yeastgenome.org).

| Systematic Name | Standard Name | Description |
|---|---|---|
| YGL053W | PRM8 | Pheromone-regulated protein with 2 predicted transmembrane segments and an FF sequence, a motif involved in COPII binding; forms a complex with Prp9p in the ER; member of DUP240 gene family |
| YGL051W | MST27 | Putative integral membrane protein, involved in vesicle formation; forms complex with Mst28p; member of DUP240 gene family; binds COPI and COPII vesicles |
| YLL024C | SSA2 | ATP binding protein involved in protein folding and vacuolar import of proteins; member of heat shock protein 70 (HSP70) family; associated with the chaperonin-containing T-complex; present in the cytoplasm, vacuolar membrane and cell wall |
| YMR170C | ALD2 | Cytoplasmic aldehyde dehydrogenase, involved in ethanol oxidation and beta-alanine biosynthesis; uses NAD+ as the preferred coenzyme; expression is stress induced and glucose repressed; very similar to Ald3p |
| YMR169C | ALD3 | Cytoplasmic aldehyde dehydrogenase, involved in beta-alanine synthesis; uses NAD+ as the preferred coenzyme; very similar to Ald2p; expression is induced by stress and repressed by glucose |
| YBR201C-A | | Putative protein of unknown function |
| YGR175C | ERG1 | Squalene epoxidase, catalyzes the epoxidation of squalene to 2,3-oxidosqualene; plays an essential role in the ergosterol-biosynthesis pathway and is the specific target of the antifungal drug terbinafine |
| YMR202W | ERG2 | C-8 sterol isomerase, catalyzes the isomerization of the delta-8 double bond to the delta-7 position at an intermediate step in ergosterol biosynthesis |
| YLR056W | ERG3 | C-5 sterol desaturase, catalyzes the introduction of a C-5(6) double bond into episterol, a precursor in ergosterol biosynthesis; mutants are viable, but cannot grow on nonfermentable carbon sources |
| YGL012W | ERG4 | C-24(28) sterol reductase, catalyzes the final step in ergosterol biosynthesis; mutants are viable, but lack ergosterol |
| YMR015C | ERG5 | C-22 sterol desaturase, a cytochrome P450 enzyme that catalyzes the formation of the C-22(23) double bond in the sterol side chain in ergosterol biosynthesis; may be a target of azole antifungal drugs |
| YMR220W | ERG8 | Phosphomevalonate kinase, an essential cytosolic enzyme that acts in the biosynthesis of isoprenoids and sterols, including ergosterol, from mevalonate |
| YPL028W | ERG10 | Acetyl-CoA C-acetyltransferase (acetoacetyl-CoA thiolase), cytosolic enzyme that transfers an acetyl group from one acetyl-CoA molecule to another, forming acetoacetyl-CoA; involved in the first step in mevalonate biosynthesis |
| YHR007C | ERG11 | Lanosterol 14-alpha-demethylase, catalyzes the C-14 demethylation of lanosterol to form 4,4"-dimethyl cholesta-8,14,24-triene-3-beta-ol in the ergosterol biosynthesis pathway; member of the cytochrome P450 family |
| YJL167W | ERG20 | Farnesyl pyrophosphate synthetase, has both dimethylallyltranstransferase and geranyltranstransferase activities; catalyzes the formation of C15 farnesyl pyrophosphate units for isoprenoid and sterol biosynthesis |
| YNL280C | ERG24 | C-14 sterol reductase, acts in ergosterol biosynthesis; mutants accumulate the abnormal sterol ignosterol (ergosta-8,14 dienol), and are viable under anaerobic growth conditions but inviable on rich medium under aerobic conditions |
| YGR060W | ERG25 | C-4 methyl sterol oxidase, catalyzes the first of three steps required to remove two C-4 methyl groups from an intermediate in ergosterol biosynthesis; mutants accumulate the sterol intermediate 4,4-dimethylzymosterol |
| YGL001C | ERG26 | C-3 sterol dehydrogenase, catalyzes the second of three steps required to remove two C-4 methyl groups from an intermediate in ergosterol biosynthesis |
| YLR100W | ERG27 | 3-keto sterol reductase, catalyzes the last of three steps required to remove two C-4 methyl groups from an intermediate in ergosterol biosynthesis; mutants are sterol auxotrophs |
| YER044C | ERG28 | Endoplasmic reticulum membrane protein, may facilitate protein-protein interactions between the Erg26p |

TABLE 1-continued

Genes Exhibiting Increased or Decreased Copy Number and/or Expression in Modified Yeast Strains Relative to Parental Strain. Systematic Name, Standard Name, and Description are taken from the *Saccharomyces* Genome Database (see URL: yeastgenome.org).

| Systematic Name | Standard Name | Description |
|---|---|---|
| | | dehydrogenase and the Erg27p 3-ketoreductase and/or tether these enzymes to the ER, also interacts with Erg6p |
| YML075C | HMG1 | One of two isozymes of HMG-CoA reductase that catalyzes the conversion of HMG-CoA to mevalonate, which is a rate-limiting step in sterol biosynthesis; localizes to the nuclear envelope; overproduction induces the formation of karmellae |
| YBR020W | GAL1 | Galactokinase, phosphorylates alpha-D-galactose to alpha-D-galactose-1-phosphate in the first step of galactose catabolism; expression regulated by Gal4p |
| YLR081W | GAL2 | Galactose permease, required for utilization of galactose; also able to transport glucose |
| YDR009W | GAL3 | Transcriptional regulator involved in activation of the GAL genes in response to galactose; forms a complex with Gal80p to relieve Gal80p inhibition of Gal4p; binds galactose and ATP but does not have galactokinase activity |
| YPL248C | GAL4 | DNA-binding transcription factor required for the activation of the GAL genes in response to galactose; repressed by Gal80p and activated by Gal3p |
| YBR018C | GAL7 | Galactose-1-phosphate uridyl transferase, synthesizes glucose-1-phosphate and UDP-galactose from UDP-D-glucose and alpha-D-galactose-1-phosphate in the second step of galactose catabolism |
| YBR019C | GAL10 | UDP-glucose-4-epimerase, catalyzes the interconversion of UDP-galactose and UDP-D-glucose in galactose metabolism; also catalyzes the conversion of alpha-D-glucose or alpha-D-galactose to their beta-anomers |
| YML051W | GAL80 | Transcriptional regulator involved in the repression of GAL genes in the absence of galactose; inhibits transcriptional activation by Gal4p; inhibition relieved by Gal3p or Gal1p binding |
| YKL127W | PGM1 | Phosphoglucomutase, minor isoform; catalyzes the conversion from glucose-1-phosphate to glucose-6-phosphate, which is a key step in hexose metabolism |
| YMR105C | PGM2 | Phosphoglucomutase, catalyzes the conversion from glucose-1-phosphate to glucose-6-phosphate, which is a key step in hexose metabolism; functions as the acceptor for a Glc-phosphotransferase |
| YOL051W | GAL11 | Subunit of the RNA polymerase II mediator complex; associates with core polymerase subunits to form the RNA polymerase II holoenzyme; affects transcription by acting as target of activators and repressors |
| YHR094C | HXT1 | Low-affinity glucose transporter of the major facilitator superfamily, expression is induced by Hxk2p in the presence of glucose and repressed by Rgt1p when glucose is limiting |
| YMR011W | HXT2 | High-affinity glucose transporter of the major facilitator superfamily, expression is induced by low levels of glucose and repressed by high levels of glucose |
| YDR345C | HXT3 | Low affinity glucose transporter of the major facilitator superfamily, expression is induced in low or high glucose conditions |
| YHR092C | HXT4 | High-affinity glucose transporter of the major facilitator superfamily, expression is induced by low levels of glucose and repressed by high levels of glucose |
| YHR096C | HXT5 | Hexose transporter with moderate affinity for glucose, induced in the presence of nonfermentable carbon sources, induced by a decrease in growth rate, contains an extended N-terminal domain relative to other HXTs |
| YDR343C | HXT6 | High-affinity glucose transporter of the major facilitator superfamily, nearly identical to Hxt7p, expressed at high basal levels relative to other HXTs, repression of expression by high glucose requires SNF3 |
| YDR342C | HXT7 | High-affinity glucose transporter of the major facilitator superfamily, nearly identical to Hxt6p, expressed at high basal levels relative to other HXTs, expression repressed by high glucose levels |
| YJL219W | HXT9 | Putative hexose transporter that is nearly identical to Hxt11p, has similarity to major facilitator superfamily (MFS) transporters, expression of HXT9 is regulated by transcription factors Pdr1p and Pdr3p |
| YOL156W | HXT11 | Putative hexose transporter that is nearly identical to Hxt9p, has similarity to major facilitator superfamily (MFS) transporters and is involved in pleiotropic drug resistance |

TABLE 1-continued

Genes Exhibiting Increased or Decreased Copy Number and/or
Expression in Modified Yeast Strains Relative to Parental Strain. Systematic
Name, Standard Name, and Description are taken from the *Saccharomyces*
Genome Database (see URL: yeastgenome.org).

| Systematic Name | Standard Name | Description |
|---|---|---|
| YIL170W | HXT12 | Possible pseudogene in strain S288C; YIL170W/HXT12 and the adjacent ORF, YIL171W, together encode a nonfunctional member of the hexose transporter family |
| YGL253W | HXK2 | Hexokinase isoenzyme 2 that catalyzes phosphorylation of glucose in the cytosol; predominant hexokinase during growth on glucose; functions in the nucleus to repress expression of HXK1 and GLK1 and to induce expression of its own gene |
| YDL194W | SNF3 | Plasma membrane low glucose sensor that regulates glucose transport; contains 12 predicted transmembrane segments and a long C-terminal tail required for induction of hexose transporters; also senses fructose and mannose; similar to Rgt2p |
| YGL252C | RTG2 | Sensor of mitochondrial dysfunction; regulates the subcellular location of Rtg1p and Rtg3p, transcriptional activators of the retrograde (RTG) and TOR pathways; Rtg2p is inhibited by the phosphorylated form of Mks1p |
| YDR028C | REG1 | Regulatory subunit of type 1 protein phosphatase Glc7p, involved in negative regulation of glucose-repressible genes |
| YJR090C | GRR1 | F-box protein component of the SCF ubiquitin-ligase complex; involved in carbon catabolite repression, glucose-dependent divalent cation transport, high-affinity glucose transport, morphogenesis, and sulfite detoxification |
| YNL111CP | CYB5 | Cytochrome b5, involved in the sterol and lipid biosynthesis pathways; acts as an electron donor to support sterol C5-6 desaturation |

Expression of Genes and Corresponding Proteins

Several genes are identified in the present invention as exhibiting a gain in copy number or increased expression in the modified yeast (Y108-1) relative to the parental yeast (LNH-ST). Yeast strains can be improved in relation to growth or fermentation of xylose in lignocellulosic hydrolysate and other advantageous modifications by overexpression of one or more of these genes. Techniques for producing such overexpression are well known in the art and include, without limitation, transcriptional, post-transcriptional, and translational upregulation. The advantageous effects of increasing the expression or activity of the proteins corresponding to the genes identified as exhibiting increased copy number or expression are also contemplated in the present invention.

Several other genes are identified in the present invention as exhibiting a loss in copy number or decreased expression in the modified yeast (Y108-1) relative to the parental yeast (LNH-ST). Yeast strains can be improved in relation to growth or fermentation of xylose in lignocellulosic hydrolysate and other advantageous modifications by underexpression (e.g., inhibition of expression) of one or more of these genes. Techniques for producing such underexpression are well known in the art and include, without limitation, transcriptional, post-transcriptional, and translational downregulation. For example, expression of these genes can be downregulated by antisense oligonucleotides, RNA interference, ribozymes, triplex-forming oligonucleotides, etc. The advantageous effects of decreasing the expression or activity of the proteins corresponding to the genes identified as exhibiting reduced copy number or expression are also contemplated in the present invention.

Production of a Lignocellulosic Hydrolysate

The lignocellulosic hydrolysate for use in the present invention results from the hydrolysis of a lignocellulosic feedstock. Representative lignocellulosic feedstocks are (1) agricultural wastes, such as corn stover, corn cobs, wheat straw, barley straw, oat straw, rice straw, canola straw, and soybean stover; (2) grasses, such as switch grass, miscanthus, cord grass, and reed canary grass; (3) forestry wastes, such as aspen wood and sawdust; and (4) sugar processing residues, such as bagasse and beet pulp. The feedstocks preferably contain high concentrations of cellulose and hemicellulose that are the source of the sugar in the aqueous stream.

Lignocellulosic feedstocks comprise cellulose in an amount greater than about 20%, more preferably greater than about 30%, more preferably greater than about 40% (wt/wt). For example, the lignocellulosic material may comprise from about 20% to about 50% (wt/wt) cellulose, or any amount therebetween. Hemicellulose may be present at 15% to 30% (wt/wt), or any amount therebetween. Furthermore, the lignocellulosic feedstock comprises lignin in an amount greater than about 10%, more typically in an amount greater than about 15% (wt/wt). The lignocellulosic feedstock may also comprise small amounts of sucrose, fructose, and starch.

Pretreatment of the Feedstock

According to one illustrative example of pretreatment of the feedstock, the lignocellulosic hydrolysate fed to the fermentation is a stream resulting from pretreating the feedstock with acid, i.e., a hemicellulosic hydrolysate. The acid pretreatment is intended to deliver a sufficient combination of mechanical and chemical action to disrupt the fiber structure of the lignocellulosic feedstock and increase the surface area of the feedstock to make it accessible to cellulase enzymes. Preferably, the acid pretreatment is performed so that nearly complete hydrolysis of the hemicellulose and only a small amount of conversion of cellulose to glucose occurs. The majority of the cellulose is hydrolyzed to glucose in a subsequent step that uses cellulase enzymes, although a small amount of the cellulose can be hydrolyzed in the acid pretreatment step as well. Typically, a dilute acid, at a concentration from about 0.02% (wt/wt) to about 5% (wt/wt), or any amount therebetween (measured as the percentage weight of pure acid in the total weight of dry feedstock plus aqueous solution) is used for the pretreatment.

A preferred pretreatment, without intending to be limiting, is steam explosion described in U.S. Pat. No. 4,416,648 (Foody; which is incorporated herein by reference).

Examples of acids that can be used in the process include those selected from the group consisting of sulfuric acid, sulfurous acid, sulfur dioxide, and combinations thereof. Preferably, the acid is sulfuric acid.

The acid pretreatment is preferably carried out at a maximum temperature of about 160° C. to about 280° C. The time that the feedstock is held at this temperature may be about 6 seconds to about 600 seconds. In one example, the pH of the pretreatment is about 0.4 to about 3.0, or any pH value or range therebetween. For example, the pH of the pretreatment may be 0.4, 1.0, 1.5, 2.0, 2.5 or 3.0. Preferably, the pretreatment is carried out to minimize the degradation of xylose and the production of furfural. Preferably, the pretreatment is also designed to minimize the degradation of pentose and hexose sugars generally.

In at least one example, the chemical used for pretreatment of the lignocellulosic feedstock is alkali. The alkali used in the pretreatment reacts with acidic groups present on the hemicellulose to open up the surface of the substrate. With alkali pretreatment, acetate is produced from acetyl groups present on the hemicellulose component of the feedstock, although the amount of acetate present will vary depending on the severity of the treatment. However, in contrast to acid pretreatment, alkali pretreatment methods may or may not hydrolyze xylan to produce xylose.

Examples of alkali that may be used in the pretreatment include ammonia, ammonium hydroxide, potassium hydroxide, and sodium hydroxide. The pretreatment may also be conducted with alkali that is insoluble in water, such as lime and magnesium hydroxide, although soluble alkali is preferred.

An example of a suitable alkali pretreatment is Ammonia Freeze Explosion, Ammonia Fiber Explosion, or Ammonia Fiber Expansion ("AFEX" process). According to this process, the lignocellulosic feedstock is contacted with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure (see U.S. Pat. Nos. 5,171,592, 5,037,663, 4,600,590, 6,106,888, 4,356,196, 5,939,544, 6,176,176, 5,037,663 and 5,171,592, which are each incorporated herein by reference). The flashed ammonia may then be recovered according to known processes.

Another suitable alkali pretreatment for use in the present invention employs dilute solutions of ammonia or ammonium hydroxide as set forth in U.S. Publication Nos. 2009/0053770 and 2007/0031918, which are each incorporated herein by reference.

Yet a further nonlimiting example of a pretreatment process for use in the present invention includes chemical treatment of the feedstock with organic solvents. Organic liquids in pretreatment systems are described by Converse et al. (U.S. Pat. No. 4,556,430; incorporated herein by reference), and such methods have the advantage that the low boiling point liquids easily can be recovered and reused. Other pretreatments, such as the Organosolv™ process, also use organic liquids (see U.S. Pat. No. 7,465,791, which is also incorporated herein by reference). Subjecting the feedstock to pressurized water may also be a suitable pretreatment method (see Weil et al. (1997) *Appl. Biochem. Biotechnol.* 68(1-2):21-40, which is incorporated herein by reference).

Processing after Pretreatment

The pretreatment produces a pretreated feedstock composition (e.g., a pretreated feedstock slurry) that contains a soluble component including the sugars resulting from hydrolysis of the hemicellulose, optionally acetic acid and other inhibitors, and solids including unhydrolyzed feedstock and lignin.

According to a further example, the soluble components of the pretreated feedstock composition are separated from the solids. The soluble fraction, which includes the sugars released during pretreatment and other soluble components, including inhibitors, may then be sent to fermentation. It will be understood, however, that if the hemicellulose is not effectively hydrolyzed during the pretreatment, it may be desirable to include a further hydrolysis step or steps with enzymes or by further alkali or acid treatment to produce fermentable sugars.

The foregoing separation may be carried out by washing the pretreated feedstock composition with an aqueous solution to produce a wash stream, and a solids stream comprising the unhydrolyzed, pretreated feedstock. Alternatively, the soluble component is separated from the solids by subjecting the pretreated feedstock composition to a solids-liquid separation, using known methods such as centrifugation, microfiltration, plate and frame filtration, cross-flow filtration, pressure filtration, vacuum filtration, and the like. Optionally, a washing step may be incorporated into the solids-liquids separation.

The separated solids, which contain cellulose, may then be sent to enzymatic hydrolysis with cellulase enzymes in order to convert the cellulose to glucose.

According to another example, the pretreated feedstock composition is fed to the fermentation without separation of the solids contained therein. After the fermentation, the unhydrolyzed solids may be subjected to enzymatic hydrolysis with cellulase enzymes to convert the cellulose to glucose.

In at least one other example, the pretreated feedstock composition, together with any sugars resulting from hemicellulose hydrolysis, is subjected to cellulose hydrolysis with cellulase enzymes. After enzymatic hydrolysis, a major component of the resulting lignocellulosic hydrolysate will be glucose, although pentose sugars derived from the hemicellulose component will be present as well.

Prior to hydrolysis with cellulase enzymes, the pH of the pretreated feedstock slurry is adjusted to a value that is amenable to the cellulase enzymes, which is typically between about 4 and about 6, although the pH can be higher if alkalophilic cellulases are used.

The enzymatic hydrolysis can be carried out with any type of cellulase enzymes capable of hydrolyzing the cellulose to glucose, regardless of their source. Among the most widely studied, characterized, and commercially produced cellulases are those obtained from fungi, such as *Trichoderma* spp., *Aspergillus* spp., *Hypocrea* spp., *Humicola* spp., *Neurospora* spp., *Orpinomyces* spp., *Gibberella* spp., *Emericella* spp., *Chaetomium* spp., *Chrysosporium* spp., *Fusarium* spp., *Penicillium* spp., *Magnaporthe* spp., *Phanerochaete* spp., *Trametes* spp., *Lentinula edodes, Gleophyllum trabeiu, Ophiostoma piliferum, Corpinus cinereus, Geomyces pannorum, Cryptococcus laurentii, Aureobasidium pullulans, Amorphotheca resinae, Leucosporidium scotti, Cunninghamella elegans, Thermomyces lanuginosus, Myceliopthora thermophila,* and *Sporotrichum thermophile,* and those obtained from bacteria of the genera *Bacillus, Thermomyces, Clostridium, Streptomyces* or *Thermobifida.* The cellulases typically comprise one or more CBHs, EGs, and β-glucosidase enzymes, and may additionally contain hemicellulases, esterases, and swollenins.

Following cellulose hydrolysis of the pretreated feedstock slurry, any insoluble solids, including but not limited to lignin, present in the resulting lignocellulosic hydrolysate may be removed using conventional solid-liquid separation techniques prior to any further processing. These solids may be burned to provide energy for the entire process.

It is also considered within the scope of the invention to produce the lignocellulosic hydrolysate by hydrolyzing the lignocellulosic feedstock in a single step with acid or alkali. This employs harsher conditions to effect hydrolysis of both the hemicellulose and cellulose components of the feedstock (see, for example, U.S. Pat. No. 5,562,777, which describes acid hydrolysis of cellulose and hemicellulose, the content of which is hereby incorporated by reference herein). Furthermore, a two-stage acid or alkali hydrolysis is also included within the scope of the invention.

Furthermore, it will be understood that, prior to fermentation, the lignocellulosic hydrolysate may be subjected to additional processing steps. In at least one example, at least a portion of the mineral acid and/or organics acids, including acetic acid, present in the hemicellulose hydrolysate are removed from the lignocellulosic hydrolysate, for example, by anion exchange (see, for example, International Patent Pub. No. WO 2008/019468, to Wahnon et al., which is incorporated herein by reference). Other processing steps that may be conducted prior to the fermentation include concentration by evaporation and/or reverse osmosis.

Components Present in the Lignocellulosic Hydrolysate

As discussed previously, hydrolysis of the hemicellulose and cellulose components of a lignocellulosic feedstock yields a lignocellulosic hydrolysate comprising xylose and glucose. Other sugars typically present include galactose, mannose, arabinose, fucose, rhamnose, or a combination thereof. Regardless of the means of hydrolyzing the lignocellulosic feedstock (e.g., full acid hydrolysis or chemical pretreatment with or without subsequent enzymatic hydrolysis), the xylose and glucose generally make up a large component of the sugars present in the lignocellulosic hydrolysate.

If the lignocellulosic hydrolysate is a hemicellulose hydrolysate resulting from acid pretreatment, xylose will be the predominant sugar and lesser amounts of glucose will be present, because a modest amount of cellulose hydrolysis typically occurs during pretreatment. According to this embodiment of the invention, the xylose can make up between about 50 and 90 wt % of the total carbohydrate content of the lignocellulosic hydrolysate. According to another embodiment of the invention, the xylose makes up greater than about 30 wt % of the total carbohydrate content, between about 50 and about 90 wt %, or between about 65 and about 90 wt % of the total carbohydrate content. For example, the xylose may make up greater than 30, 35, 40, 45, 50, 55, 60, 65, 70, 75, 80, 85, 90 or 95 wt % of the total carbohydrate content. It will be appreciated by those of skill in the art that the relative amount of xylose present in the lignocellulosic hydrolysate will depend on the feedstock and the pretreatment that is employed.

If the lignocellulosic hydrolysate results from hydrolysis of the cellulose and hemicellulose components of the feedstock, e.g., full acid or alkali hydrolysis, it will contain all of the sugars listed above, but will contain higher levels of glucose derived from the more complete hydrolysis of the cellulose.

In addition to the aforementioned sugars, lignocellulosic hydrolysates derived from lignocellulosic feedstocks contain a number of compounds that may or may not be inhibitory to the yeast. For example, furan derivatives such as 2-furaldehyde (furfural) and 5-hydroxymethyl-2-furaldehyde (HMF) are inhibitory compounds that originate from the breakdown of the carbohydrate fraction, namely xylose and glucose, respectively. These compounds can be degraded further by pretreatment or hydrolysis into organic acids including acetic acid, as well as formic and levulinic acids, which are also inhibitory. Additional organic acids found in the lignocellulosic hydrolysate that may be inhibitory to yeast include galacturonic acid, lactic acid, glucuronic acid, 4-O-methyl-D-glucuronic acid, or a combination thereof. Inhibiting phenolic compounds are also produced by the degradation of lignin; these include vanillin, syringaldehyde, and hydroxybenzylaldehyde. In particular, vanillin and syringaldehyde are produced via the degradation of syringyl propane units and guaiacylpropane units of lignin (Jonsson et al. (1998) *Appl. Microbiol. Biotechnol.* 49:691).

As discussed previously, acetic acid is a component of lignocellulosic hydrolysates that is highly inhibitory to yeast. The acetate arises from acetyl groups attached to xylan and lignin that are liberated as acetic acid and/or acetate by exposure to acid or other chemicals that hydrolyze the feedstock (Abbott et al. (2007) *FEMS Yeast Res.* 7:819-33; Hu et al. (2009) *Bioresource Technology* 100:4843-47; Taherzadeh et al. (1997) *Chem. Eng. Sci.* 52(15):2653-59). Acetic acid has a $pK_a$ of about 4.75 ($K_a$ of $1.78 \times 10^{-5}$), so that at pH 4.0 about 14.8 mole % of the acid is present as acetate. Thus, the species present in the lignocellulosic hydrolysate will depend on the pH of the solution. Although it should be appreciated that the practice of the invention is not limited by the pH of the lignocellulosic hydrolysate, the fermentation is typically conducted at a pH at which acetate is the dominant species in solution. Acetic acid may be present in the lignocellulosic hydrolysate at a concentration of between about 0.1 and about 50 g/L, about 0.1 and about 20 g/L, about 0.5 and about 20 g/L, or about 1.0 and about 15 g/L. The inhibitory compounds set forth above are representative of the compounds present in a lignocellulosic hydrolysate produced from a lignocellulosic feedstock. A more extensive list of compounds that are present after pretreatment is provided in Klinke et al. ((2004) *Appl. Microbiol. Biotechnol.* 66:10-26), the content of which is incorporated herein by reference. It will be appreciated that the substances present depend on both the raw material and the pretreatment that is employed.

Process for Fermentation of Lignocellulosic Hydrolysate by Modified Yeasts

For the purposes of the fermentation process defined herein, fermentation means the conversion of the sugars or other carbon sources present in a lignocellulose hydrolysate by a microorganism, such as a yeast cell, to a fermentation product, and/or the utilization of such sugars and/or other carbon sources for cell growth. A fermentation product is defined as an organic molecule produced by, e.g., the modified yeast from the sugars and/or other carbon-containing substances present in the lignocellulose hydrolysate, as described hereinabove. For example, the fermentation product may be an alcohol, such as ethanol or butanol, or a sugar alcohol, such as xylitol.

Preferably, the fermentation process is performed at or near the temperature and pH optima of the fermentation microorganism. A typical temperature range for the fermentation of xylose to ethanol using *Saccharomyces* spp. is between about 25° C. to about 37° C. or any temperature therebetween, for example, from 25, 26, 27, 28, 29, 30, 31, 32, 33, 34, 35, 36, 37° C. or any temperature therebetween, although the temperature may be higher if the yeast is naturally or genetically modified to be thermostable. For example, the temperature may be from about 25° C. to about 55° C., or any value therebetween. The pH of a typical fermentation employing *Saccharomyces* spp. is between about 3 and about 6, or any pH therebetween, for example, a pH of 3.0, 3.5, 4.0, 4.5, 5.0, 5.5, 6.0, or any pH therebetween.

The initial concentration of the fermentation microorganism will depend on other factors, such as the activity of the fermentation microorganism, the desired fermentation time, the volume of the reactor, and other parameters. It will be appreciated that these parameters may be adjusted as desired by one of skill in the art to achieve optimal fermentation conditions.

A person of ordinary skill in the art will appreciate that the fermentation of lignocellulose hydrolysate using the modified yeast described herein can be performed under aerobic, microaerobic, or anaerobic culture conditions. The appropriate ranges for duration of time for various steps in the fermentation process will also be familiar to one of skilled in the art.

The fermentation medium containing the lignocellulosic hydrolysate may also be supplemented with additional nutrients. For example, yeast extract, specific amino acids, phosphate, nitrogen sources, salts, trace elements, and vitamins may be added to the hydrolysate slurry to support growth and optimize productivity of the microorganism.

The fermentation may be conducted in batch, continuous, or fed-batch modes, with or without agitation. The fermentation may also be conducted under chemostat conditions. Preferably, the fermentation reactors are agitated lightly with mixing. In a typical commercial-scale process, the fermentation may be conducted using a series of reactors.

The fermentation may be conducted so that the modified yeast cells are separated from the fermentation and sent back to the fermentation reaction. This may involve continuously withdrawing fermentation broth from the fermentation reactor and separating the yeast from this solution by known separation techniques to produce a yeast slurry. Examples of suitable separation techniques include, but are not limited to, centrifugation, microfiltration, plate and frame filtration, crossflow filtration, pressure filtration, settling, vacuum filtration, and the like.

The yeast slurry then may be treated with an oxidant to destroy microbial contaminants. The oxidant may be selected from ozone, chlorine, chlorine dioxide, hydrogen peroxide, and potassium permanganate. For example, the oxidant may be chlorine dioxide; this oxidant destroys microbial cells via the oxidation of aromatic and sulfur-containing amino acids of the intracellular enzymes. Chlorine dioxide is particularly suitable as an oxidant as bacteria are more susceptible to its effects than yeast because most bacterial enzymes are located just inside the cell membrane whereas most yeast enzymes reside deeper inside the cell structure. Methods for using oxidants to destroy microbial contaminants in yeast cultures are described in, e.g., Chang et al. (1997) *Appl. Environ. Microbiol.* 63:1-6; International Patent Pub. Nos. WO 2007/097874; WO 2009/026706; WO 2007/149450; and U.S. Patent Pub. No. 2009/0061490.

The entire contents of all references, patents, and patent applications cited throughout this application are hereby incorporated by reference herein.

EXAMPLES

Example 1

Evolutionary Engineering of a Parental Yeast Strain to Produce a Modified Yeast Strain with Enhanced Fermentation of Xylose in Lignocellulosic Hydrolysate Example 1.1

Feed Preparation

Hydrolysate from a dilute acid-pretreated lignocellulosic biomass, conducted as set forth in U.S. Pat. No. 4,461,648 (incorporated herein by reference), was concentrated by evaporation. Hydrolysate was mixed with pure sugar and nutrient components according to media recipe #1 (Media #1) in Table 2 (displaying components of Media #s 1, 2, 4, 5, and 6). Salts, trace elements, and yeast extract were added, on a per liter basis, to the chemostat feed. The trace solution was prepared according to Verduyn et al. (1992) *Yeast* 8(7):501-17, which is incorporated herein by reference.

TABLE 2

Media Recipes

| Compound | Media #1 | Media #2 | Media #4 | Media #5 | Media #6 |
|---|---|---|---|---|---|
| Yeast Extract (g/L) | 5 | 10 | 10 | — | — |
| Peptone (g/L) | — | 20 | 20 | — | — |
| $(NH_4)_2SO_4$ (g/L) | 9 | — | — | 5 | — |
| $KH_2PO_4$ (g/L) | 2 | — | — | 3 | — |
| $MgSO_4 \cdot 7H_2O$ (g/L) | 2 | — | — | 0.5 | — |
| $CaCl_2 \cdot 2H_2O$ (g/L) | 0.4 | — | — | — | — |
| Trace elements (mL/L) | 2 | — | — | 1 | — |
| Glucose (pure) (g/L) | 0-10 | 60 | 12 | 60 | — |
| Glucose (lignocellulosic hydrolysate) (g/L) | — | — | — | — | 60 |
| Xylose (pure) (g/L) | 0-40 | 20 | — | — | — |
| Xylose (lignocellulosic hydrolysate) (g/L) | 0-22 | — | 36 | — | 30 |
| Acetic acid (g/L) | 0-3.2 | — | 5 | 4.5 | 4.5 |
| pH | 5 | 4.8 | 4.8 | 5.5 | 5.5 |

Preparation of media for propagation of cells used to evaluate fermentability performance is described in Table 2 (Media #2).

Preparation of pure sugar media for fermentability assays was prepared according to Media #4 in Table 2. Lignocellulosic hydrolysate for fermentability assays was prepared by dilute acid pretreatment followed by enzymatic hydrolysis (Media #6).

Example 1.2

Inoculum Propagation for Chemostat

A parental *S. cerevisiae* strain LNH-ST was prepared as described in U.S. Pat. No. 7,527,927 and contained several copies of the plasmid pLNH-ST (FIG. 15), containing the XR-, XDH- and XK-encoding genes integrated into its genome.

The parental strain LNH-ST ($10^8$ cells) was used to inoculate a 2 L baffled flask containing 1000 mL of media containing Media #2 from Table 2. Cells were cultivated for 48 h in a shaker incubator at 30° C. and 160 rpm. The entire contents of the flask were transferred aseptically to a controlled 7.5 L New Brunswick Bioflow III bioreactor containing 3 L of Media #1 with 10 g/L glucose and 0 g/L xylose. The culture was incubated for 3 h at the aforementioned conditions and then fed at a rate of 3 g glucose/h for 18 h. This initial propagation step provided a sufficiently large cell culture for the evolutionary engineering experiment.

Example 1.3

Chemostat Operation

Using increasing amounts of xylose originating from lignocellulosic hydrolysate, the chemostat was fed sugars corresponding to a dilution rate of 0.01-0.02 $h^{-1}$. The bioreactor, with a working volume of 4 L, was maintained at 30° C., and the pH was maintained at pH 4.5 using 15% v/v $NH_4OH$. The reactor was stirred at 150 rpm and sparger-aerated between 0-0.8 standard liters per minute (slpm). The chemostat conditions were maintained for approximately 2700 h, at which point the lignocellulosic hydrolysate content had increased from 0 g/L to 22 g/L xylose.

As a person of ordinary skill in the art will be aware, the term "dilution rate" refers to the ratio of the feed rate to the volume of culture in the vessel. That is, in a continuous stirred-tank reactor (CSTR) configuration, the volume of the culture remains constant and, as such, the feed rate remains constant as well.

A colony was isolated from the chemostat after approximately 2700 h using a 1.5% agar plate containing 10 g/L yeast extract, 20 g/L peptone, and 17 g/L xylose from lignocellulosic hydrolysate. The isolated colony with the adaptation to the lignocellulosic hydrolysate was named Y108-1.

Example 2

Measurement of Differential Fermentation Performance of Evolved Yeast Strain Compared to Parental Strain Fermentability performance: After 48 h of flask propagation in Media #2 (Table 2) at 30° C. and 150 rpm, the parental strain LNH-ST and the evolutionarily modified Y108-1 strain were centrifuged at 3000×g for 5 min and used to inoculate 400 mL of either pure sugar media (Media #5) or lignocellulosic hydrolysate (Media #6) to ~8.0 g/L final biomass anaerobic 500 mL bioreactors. Prior to inoculation, the media was sparged with pure $CO_2$ for 2 min to ensure anaerobicity. Cells were allowed to ferment at 30° C., 150 rpm until sugar exhaustion. $CO_2$ production was monitored for the course of the fermentation and samples were taken for dry cell weight and HPLC analysis.

The samples were analyzed for cell mass using dry cell weight (Rice et al. (1980) *Am. Soc. Brew. Chem. J.* 38:142-45). For the fermentability analysis, samples were taken from the bioreactors using a 10 mL syringe. From each sample, 2 mL volumes were centrifuged and the supernatant decanted and filtered through a 0.2 μm syringe filter. Each supernatant sample was diluted with 5 mM sulfuric acid. All dilutions were analyzed for glucose, xylose, xylitol, glycerol, and ethanol content on the Agilent 1100 Series Refractive Index Detector HPLC, while acetic and lactic acid were analyzed concurrently using an Agilent 1200 Series Variable Wavelength Detector HPLC. The column used for separation was the Varian Metacarb 87H Organic Acid column, maintained at 50° C. with a 5 mM sulfuric acid mobile phase at a flow rate of 0.6 mL/min. The unit was equipped with the 1100 Series Auto-sampler and Pumping System and controlled with the Chemstation software.

Using equivalent cell concentrations, the xylose consumption rate in lignocellulosic hydrolysate (FIG. 1A) shows that the modified strain (Y108-1) was able to convert over 60% of initial xylose to ethanol in 10 h, compared to the parental strain (LNH-ST), which required 20 h. The modified strain was also able to consume all available sugars, whereas the parental strain ceased fermentation with about 8 g/L residual xylose. These differences are not observed in pure sugar media fermentations (FIG. 1B).

Figure 1A:
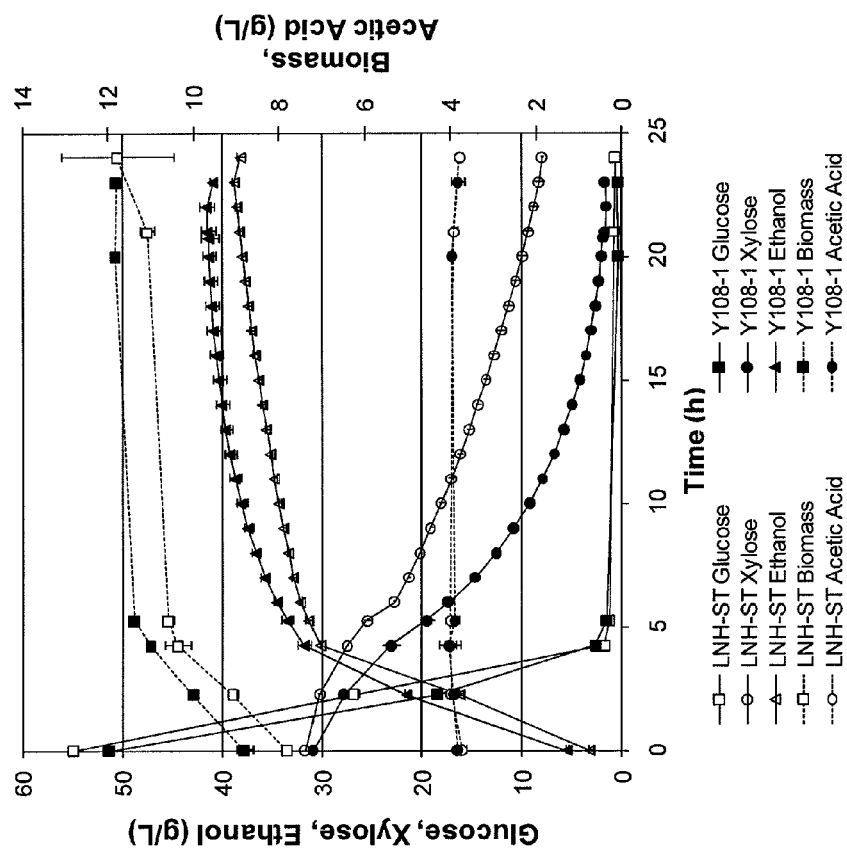
FIGS. 1A and 1B show comparisons of glucose and xylose consumption and ethanol production in lignocellulosic hydrolysate (FIG. 1A) and pure sugar media (FIG. 1B). Data presented are averages of experiments (n=3) for each condition and strain. The modified strain (Y108-1) only exhibited increased xylose uptake and conversion during the fermentation of lignocellulosic hydrolysate (FIG. 1A), and not in pure sugar media (FIG. 1B), when compared to the parental strain (LNH-ST).
Figure 1B:
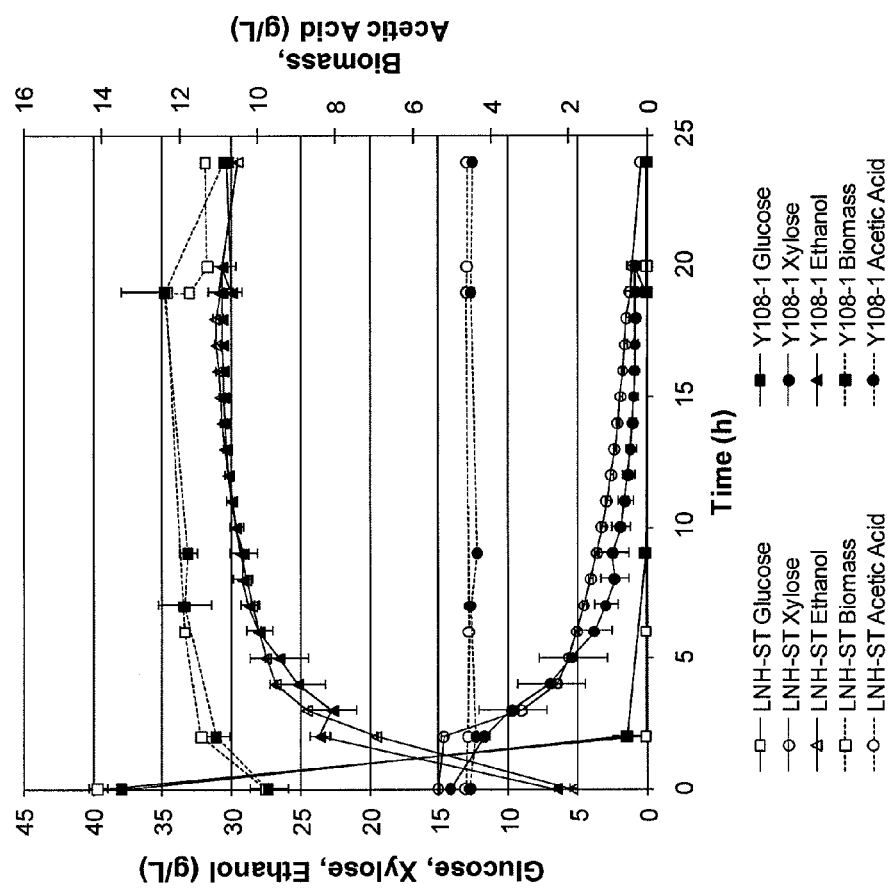
Figure 2:
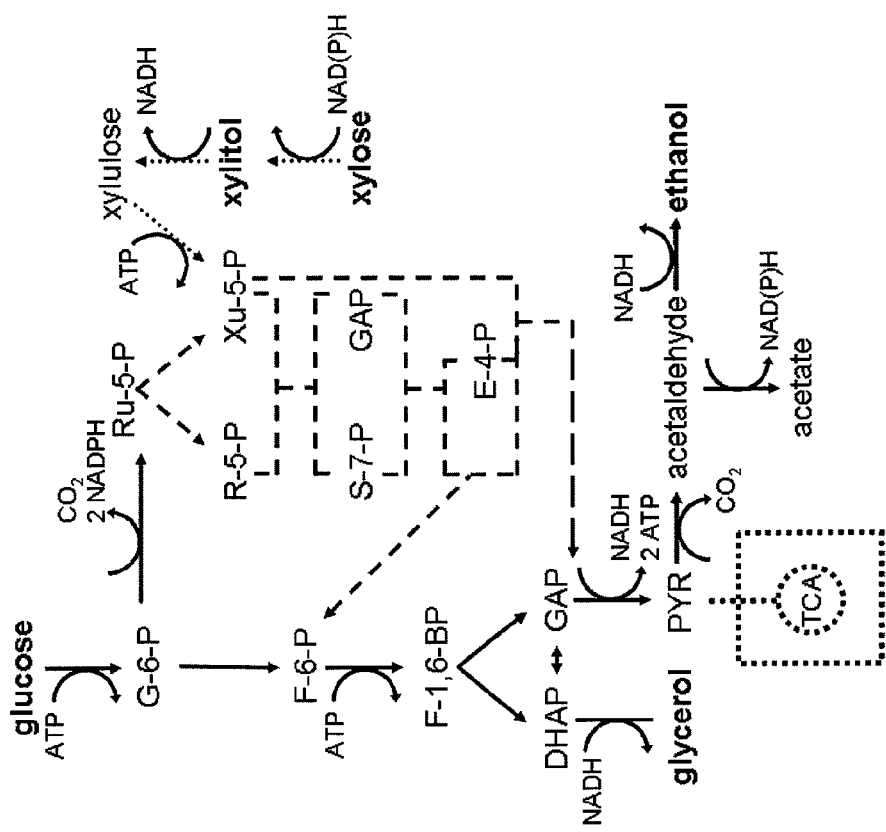
FIG. 2 is a metabolic diagram depicting glycolysis (solid arrows), the pentose phosphate pathway (dashed arrows), and the introduced pathway required for xylose utilization (dotted arrows). Abbreviations: G-6-P (glucose-6-phosphate), F-6-P (fructose-6-phosphate), F-1,6-BP (fructose-1,6-bisphosphate), DHAP (dihydroxyacetone phosphate), GAP (glyceraldehyde-3-phosphate), PYR (pyruvate), Ru-5-P (ribulose-5-phosphate), R-5-P (ribose-5-phosphate), Xu-5-P (xylulose-5-phosphate), S-7-P, (sedoheptulose-7-phosphate), and E-4-P (erythrose-4-phosphate).
Figure 3:
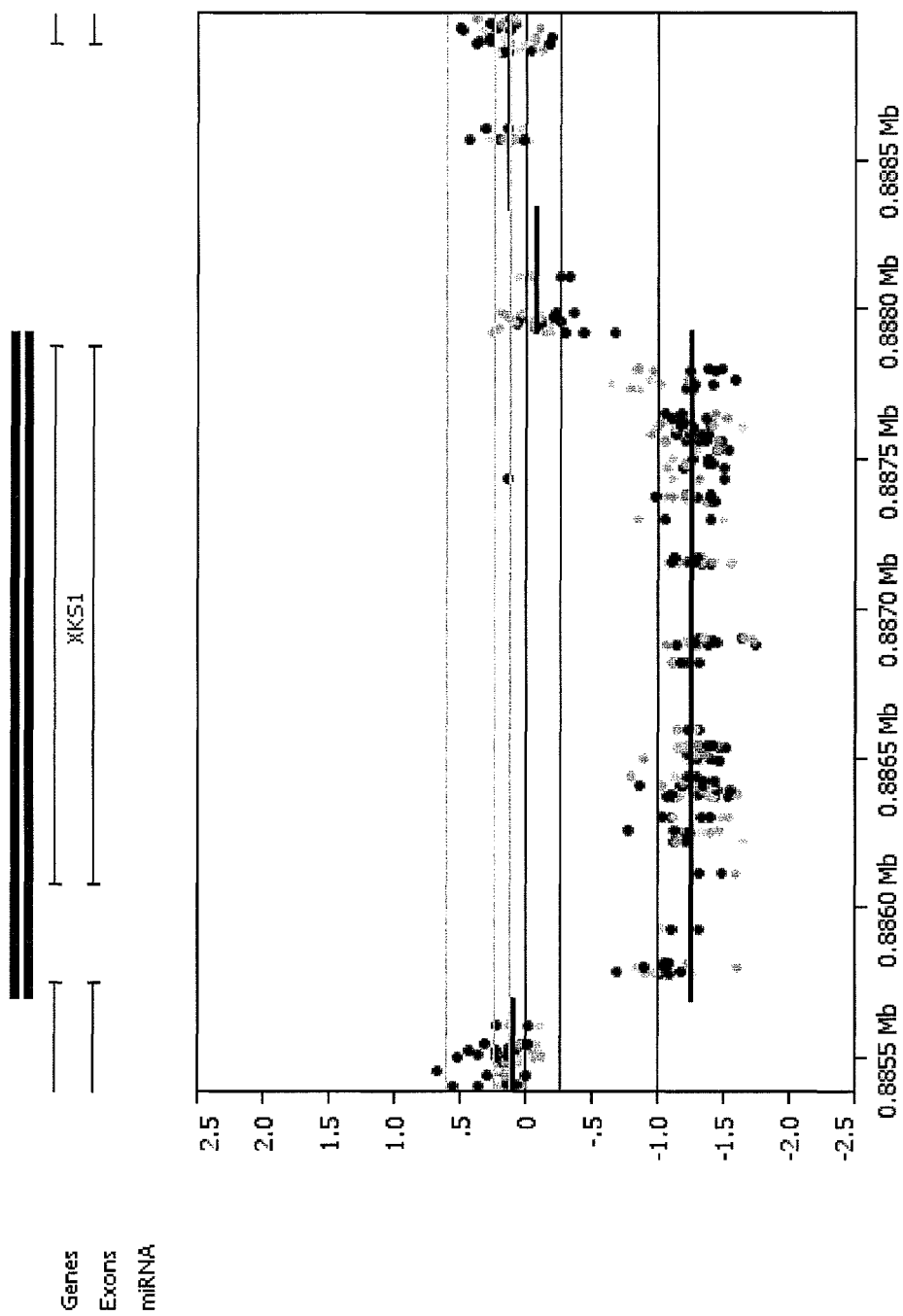
FIG. 3 presents a CGH summary plot showing high copy gain in XKS1.
Figure 4:
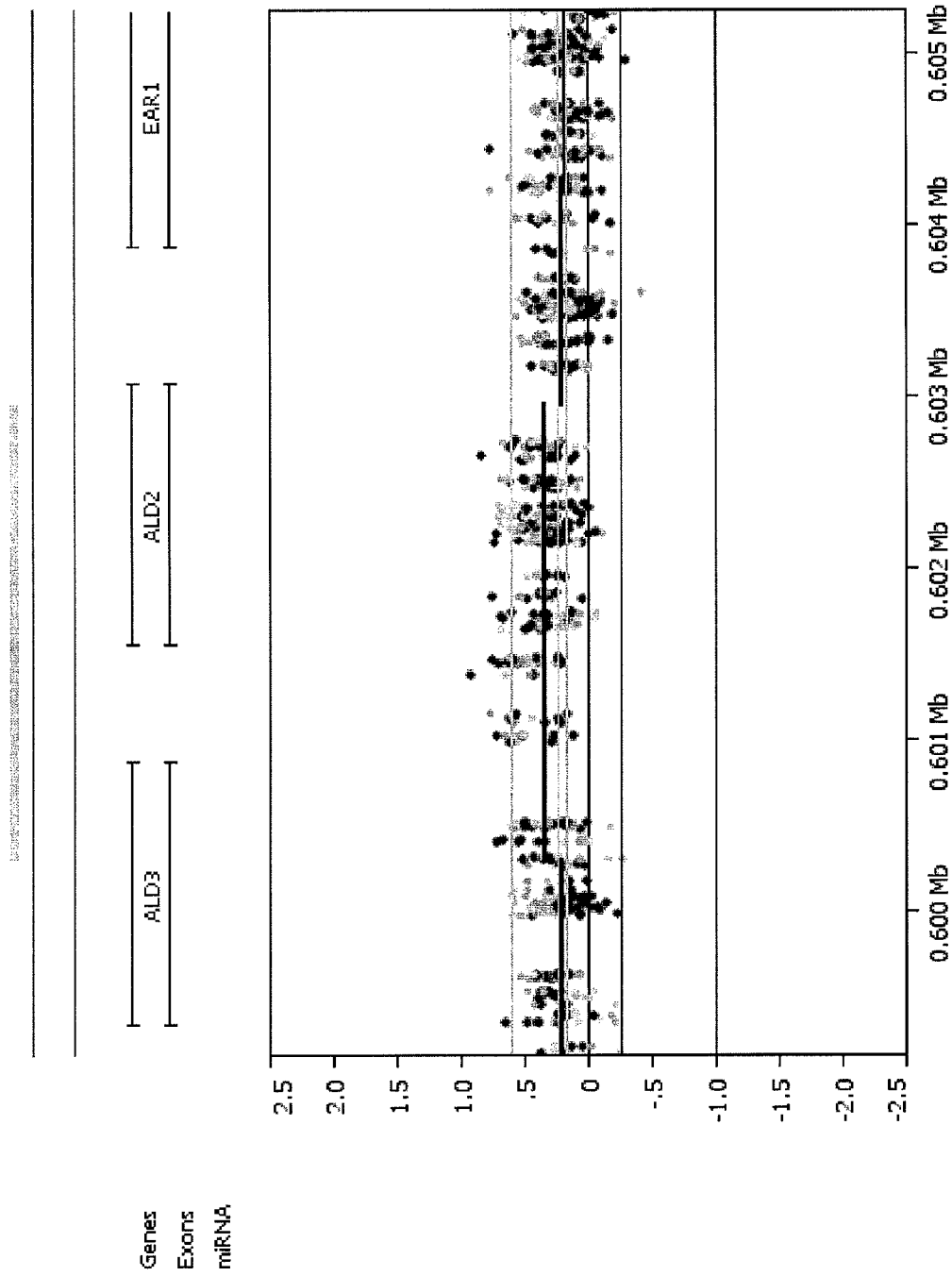
FIG. 4 presents a CGH summary plot showing copy losses in ALD2 and ALD3.
Figure 5:
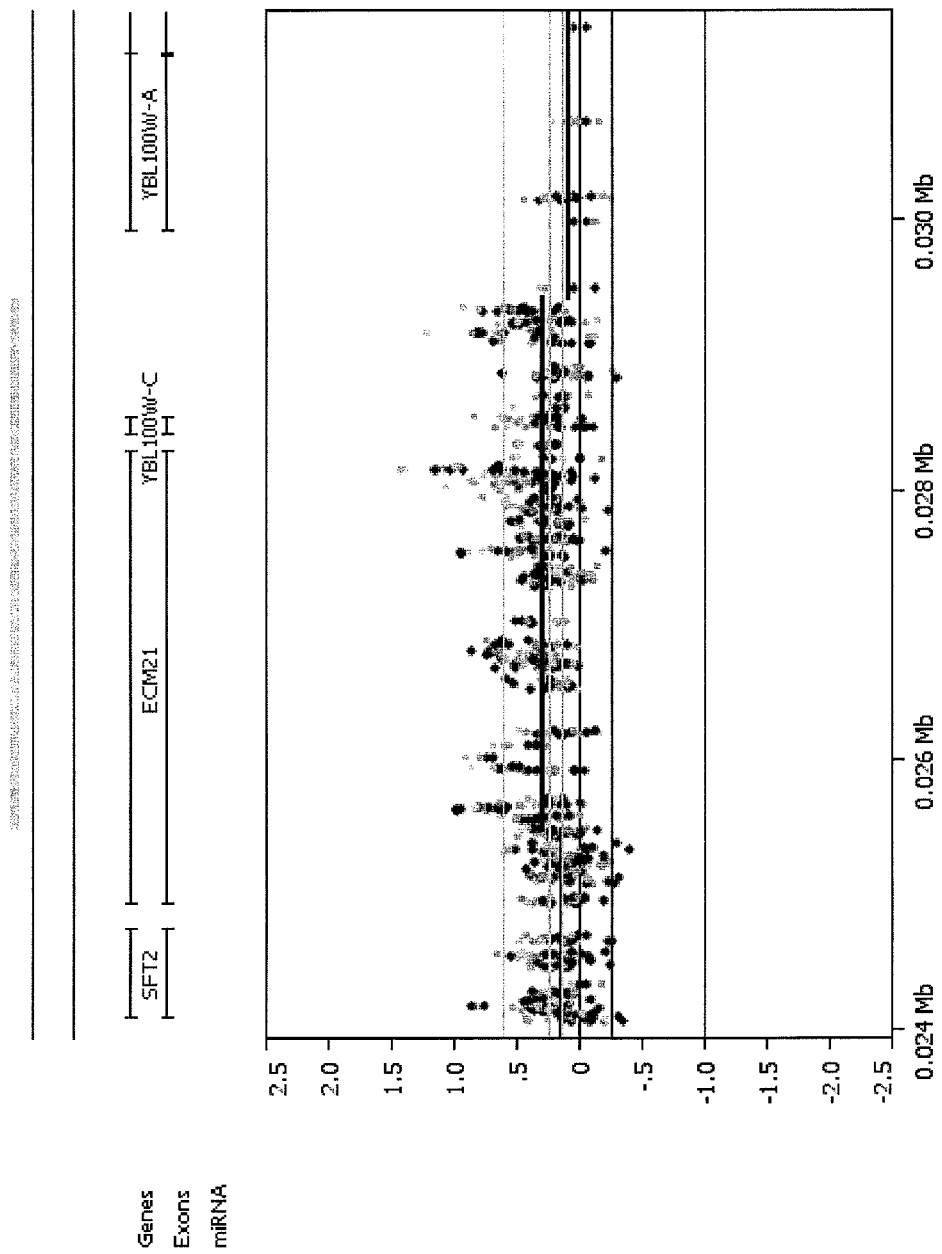
FIG. 5 presents a CGH summary plot showing copy losses in ECM21 and YBL100W-C.
Figure 6:
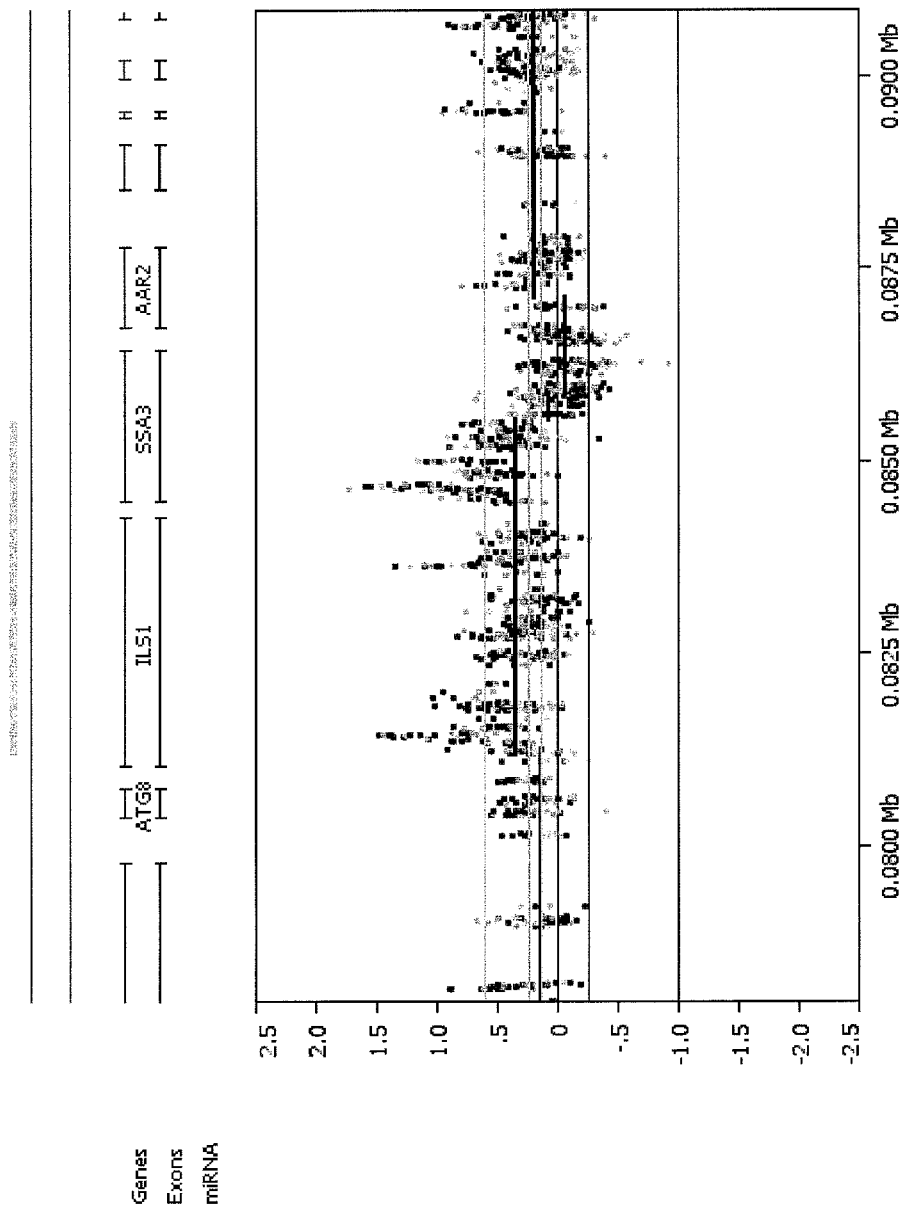
FIG. 6 presents a CGH summary plot showing copy loss in ILS1.
Figure 7:
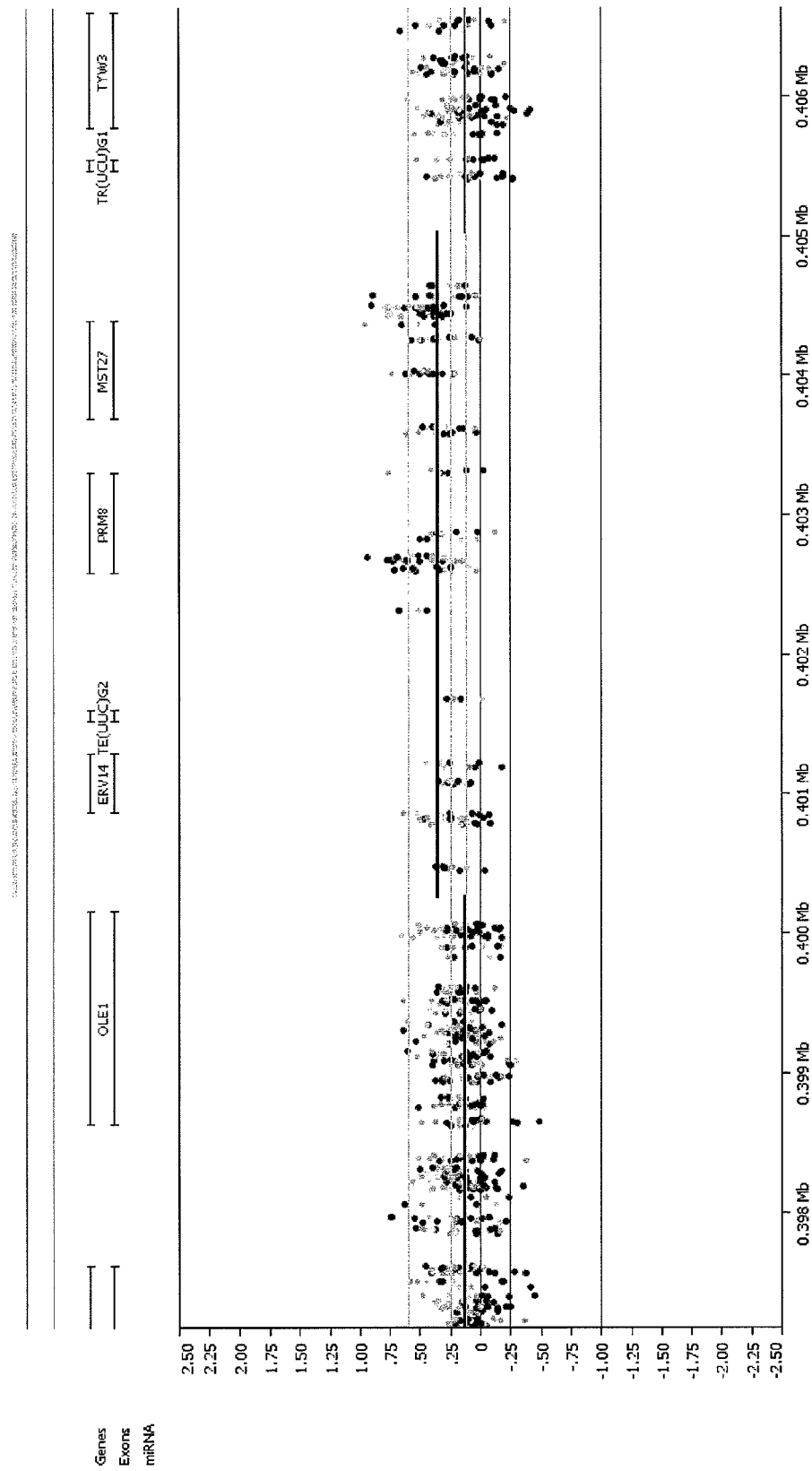
FIG. 7 presents a CGH summary plot showing copy losses in MST27, PRM8, ERV14, and tE(UUC)G2.

Biomass and acetic acid production in the lignocellulosic and pure sugar fermentations were not affected by evolutionary modification (FIGS. 1A and 1B). However, xylitol production was minimized by the fermentation of lignocellulosic hydrolysate with the modified strain (Y108-1), which may be indicative of an optimization of the redox imbalance (Table 3). *S. cerevisiae* harbors three cytosolic aldehyde dehydrogenases, two of which are $NAD^+$-dependent (encoded by ALD2 and ALD3) (Navarro-Avino et al. (1999) *Yeast* 15(10A):829-42) and one of which is $NADP^+$-dependent (encoded by ALD6) (Meaden et al. (1997) *Yeast* 13(14):1319-27). Modig et al. ((2002) *Biochem. J.* 363:769-76) demonstrated that purified aldehyde dehydrogenase from baker's yeast can utilize furfural as a substrate in a conversion of furfural to a less inhibiting analogue. The presence of furfural in lignocellulosic hydrolysates may result in increased generation of NADPH required for continued xylose reductase activity, perhaps by increasing flux through the remaining $NADP^+$-dependent isoform, ALD6p, the overexpression of which has been reported to confer resistance to furfural and HMF (Petersson et al. (2006) *Yeast* 23: 455-64).

TABLE 3

Comparison of the Physiological Parameters of Fermentation in Pure Sugar Media and Lignocellulosic Hydrolysate with the Modified Strain (Y108-1) and the Parental Strain (LNH-ST)

| | Pure Sugar Media | | Lignocellulosic Hydrolysate | |
|---|---|---|---|---|
| | Y108-1 | LNH-ST | Y108-1 | LNH-ST |
| Yield to ethanol from glucose and xylose (g/g) | 0.49 +/− 0.00 | 0.48 +/− 0.01 | 0.44 +/− 0.01 | 0.45 +/− 0.01 |
| Yield to ethanol from glucose (g/g) | ND** | ND** | 0.44 +/− 0.01 | 0.45 +/− 0.01 |

TABLE 3-continued

Comparison of the Physiological Parameters of Fermentation in Pure
Sugar Media and Lignocellulosic Hydrolysate with the Modified Strain (Y108-1)
and the Parental Strain (LNH-ST)

|  | Pure Sugar Media | | Lignocellulosic Hydrolysate | |
| --- | --- | --- | --- | --- |
|  | Y108-1 | LNH-ST | Y108-1 | LNH-ST |
| Glucose uptake: $q_G$ (g sugar/g cells/h) | 1.87 +/− 0.03[%] | 1.67 +/− 0.08[%] | 1.55 +/− 0.01[%] | 1.48 +/− 0.01[%] |
| Yield to ethanol from xylose (g/g) | ND** | ND** | 0.44 +/− 0.01 | 0.44 +/− 0.01 |
| Specific xylose uptake: $q_x$ (g sugar/g cells/h) | 0.10 +/− 0.01[#] | 0.11 +/− 0.02[#] | 0.15 +/− 0.00[##] | 0.07 +/− 0.01[##] |
| Yield to xylitol from xylose (g/g) | 0.018 +/− 0.002 | 0.030 +/− 0.018 | 0.021 +/− 0.001* | 0.044 +/− 0.004* |

*Denotes statistical differences in the mean value of triplicate determinations (Student's t-test, $p < 0.05$). It is expected that values between media may differ, whereas differences between strains are limited to xylose fermentation performance in lignocellulosic hydrolysates. Yields are based on sugar consumed and ethanol or xylitol produced.
[#]Based on an average specific xylose consumption rate between 4 and 9 g/L residual xylose.
[##]Based on an average specific xylose consumption rate between 8 and 17 g/L residual xylose.
**ND Not determined-the rapid rate of the co-consumption of glucose and xylose in the Pure Sugar Media prevents calculation of separate xylose and glucose consumption rates.
[%]Based on initial rate.

Table 3 indicates the physiological parameters for glucose and xylose fermentation for the modified and parental yeast strains. Evolutionary modification of the parental strain (LNH-ST) to produce the modified strain (Y108-1) did not affect yield or uptake of glucose. However, xylose utilization and uptake rate were improved in the modified strain Y108-1. The Y108-1 strain also demonstrated decreased loss of xylose to xylitol production.

Example 3

Comparative Genomic Hybridization Analysis of the Modified and Parental Yeast Strains Example 3.1

DNA Isolation

DNA isolation for comparative genomic hybridization (CGH) arrays was performed with the Promega A1120 Wizard genomics DNA purification kit (Fisher Scientific, Nepean, Ontario, Canada) according to the manufacturer's instructions. Briefly, Y108-1 and LNH-ST were grown for 48 h in 3 mL of YPD (Yeast extract Peptone Dextrose) broth (10 g/L yeast extract, 20 g/L peptone, and 20 g/L dextrose) at 30° C. on an orbital wheel at maximum rotation. Cells from 1 mL of culture were pelleted by centrifugation at 14,500 rpm for 2 min and then resuspended in 293 μL of 50 mM EDTA. Cells were lysed by addition of 7.5 μL of 20 mg/mL lyticase and 60 min of incubation at 37° C. After cooling to room temperature, the sample was centrifuged at 14,500 rpm for 2 min and the supernatant was removed. Nuclei lysis and protein precipitation solutions (300 μL and 100 μL, respectively) were added to the pellet, mixed, and vortexed for 20 sec. The sample was incubated on ice for 5 min and then centrifuged at 14,500 rpm for 3 min. The supernatant was transferred to a sterile microcentrifuge tube containing 300 μL of room temperature isopropanol and mixed by inversion. After centrifugation at 14,500 rpm for 2 min, the supernatant was decanted and the tube drained on a clean paper towel. The DNA pellet was then washed with 300 μL of room temperature 70% ethanol. The sample was centrifuged at 14,500 rpm for 2 min and the ethanol supernatant was aspirated. The tube was drained (clean paper towel) and allowed to air-dry for 10 min.

To rehydrate the DNA, 40 μL of DNA rehydration solution was added along with 1.5 μL of RNase solution. After mixing, the tube was incubated at 37° C. for 15 min. To allow for complete rehydration, the DNA pellet was incubated overnight at 4° C. and then stored at −20° C.

Example 3.2

Comparative Genomic Hybridization

Comparative genomic hybridization (CGH) measures DNA copy number differences between test and reference genomes. Roche NimbleGen Inc. offers whole-genome CGH array products that measure DNA copy number gains and losses across entire genomes. Whole genome tiling arrays of 385K format were used (catalog number B2436001-00-01, design 2007-05-08 SCER WG CGH). Duplicate genomic DNA samples of both Y108-1 and LNH-ST (biological duplicates) were shipped on dry ice to the Roche NimbleGen Inc. facility (Reykjavik, Iceland) for use in the CGH experiment and were labeled twice with opposite fluorophores (technical replicate) to control for dye-incorporation bias. The genomic samples were labeled and hybridized, and arrays were scanned according to NimbleGen's internal protocols (see cgh_userguide_version 4_0.pdf). Probe intensities were quantified and processed with Roche NimbleGen NimbleScan and SignalMap software, respectively, by NimbleGen.

Data from the CGH experiments were analyzed further with BioDiscovery Nexus software (El Segunda, Calif.). Significant copy number changes were determined. Briefly, log-ratio data were loaded into the BioDiscovery Nexus Copy Number program for each hybridization. Regions of copy number change were identified by optimized segmentation and calling using BioDiscovery's proprietary Rank Segmentation algorithm. A report was generated that included: a summary plot indicating the number of oligonucleotides within each gene or open reading frame (ORF) showing differential hybridization to the sample and reference genomes, the frequency of differential hybridization for each oligonucleotide across the replicate hybridizations, the Quality score per each labeled DNA sample, and a list of all genes and their annotations for which contiguous regions of oligonucleotides showed differential hybridization between the reference and sample genomes.

From these data, the genes in which a region of greater than about 60% displayed differential hybridization were selected as those whose deletion or amplification are involved in improving tolerance to, and fermentation performance of, lignocellulosic hydrolysate (Table 4; see also, e.g., FIGS. 3-7). Other changes observed in the genome of the modified strain (Y108-1) as compared to the genome of the parental strain (LNH-ST) include decreases in copy numbers of chromosomes 1 and 6 and increases in copy numbers of chromosomes 9, 10, 11, 14, and 15.

TABLE 4

Genome Changes Identified in Modified Yeast Relative to Parental Yeast

| Gene or ORF | Copy number change | Gene or ORF | Copy number change |
|---|---|---|---|
| CDC19 | high gain | ECM21 | loss |
| XKS1 | high gain | ILS1 | loss |
| ADH1 | high gain | YBL100W-C | loss |
| tE(UUC)B | gain | PRP6 | loss |
| BIK1 | gain | ERV14 | loss |
| RNQ1 | gain | tE(UUC)G2 | loss |
| FUS1 | gain | PRM8 | loss |
| PDI1 | gain | MST27 | loss |
| YCL042W | gain | SSA2 | loss |
| GLK1 | gain | ALD2 | loss |
| YCR045C | gain | ALD3 | loss |
| IMG1 | gain | YBR201C-A | loss |
| BUD23 | gain | | |
| ARE1 | gain | | |
| YCL073C | gain | | |
| VBA3 | gain | | |
| DDI2 | gain | | |
| SNO3 | gain | | |
| SNZ3 | gain | | |

Example 4

Monitoring of Gene Expression in Y108-1 vs. LNH-ST Strains

Example 4.1

Isolation of RNA from Yeast Biomass

Triplicate samples with approximately 10 g/L of biomass were collected at time points of 13.5 h and 23 h from the fermentation cultures of the modified (Y108-1) and parental yeast strains described in Example 1. Biomass was collected by centrifugation at 14,000 rpm for 3 min at 4° C., washed in cold sterile water three times, and frozen in liquid nitrogen. Yeast cells were resuspended in 600 µL RLT extraction buffer (Qiagen, Mississauga, Ontario, Canada) supplemented with 10 µL of β-mercaptoethanol and lysed with glass beads using a FastPrep (MP Biomedicals, Solon, Ohio) tissue disruptor (40 sec at a speed of 5 m/s). Total RNA was extracted using the yeast procedure outlined in Qiagen RNeasy mini kit (cat #74104). RNA was quantified on Nanodrop spectrophotometer (Thermo Scientific) using a conversion OD260 nm=1.0 representing a concentration of 40 µg/mL. RNA integrity was verified by running the samples on a 2100 BioAnalyzer (Agilent Technologies, Mississauga, Ontario, Canada).

Example 4.2

Global Expression Profiling

For comparison of the global gene expression profiles of the modified (Y108-1) and parental (LNH-ST) yeast strains fermenting lignocellulose hydrolysate, custom S. cerevisiae 8×15K 60 mer microarrays (Agilent Technologies) were designed using the online software e-array (Agilent Technologies) using 6649 predicted ORFs (orf_coding_all.20080606.fasta downloaded from the URL: downloads.yeastgenome.org) and designing up to two oligomers per ORF. Two labeling reactions, one with Cy3 and one with Cy5, of each of the triplicate RNA samples prepared as in Example 4.1 were performed as follows: Agilent's "Two-Color Quick Amp Labeling" procedure (version 5.7) was followed for labeling 500 ng of total RNA.

A total of six hybridizations (three RNA samples×two labeling reactions) were performed for each of the time points using the RNA from the parental yeast strain (LNH-ST) as a reference, and the RNA from the modified yeast strain (Y108-1) as the test sample. Hybridizations were performed overnight at 65° C. in a Robbins Scientific Model 400 oven with an Agilent Hybridization Oven Rotator. Following hybridization, microarrays were washed using the standard wash procedure as described in the Agilent protocol. Slides were read using a Genepix 4200a microarray scanner (Molecular Devices) at 5 µM resolution. Feature-finding was performed with Genepix Pro 6.0 (Molecular Devices). The results file (.gpr) was imported into Acuity 4.0 (Molecular Devices, Sunnyvale, Calif.) and Lowess normalization was applied. Analysis was continued using Lowess M log ratio as the datatype. Technical replications were combined and one-way ANOVA performed.

Figure 12:
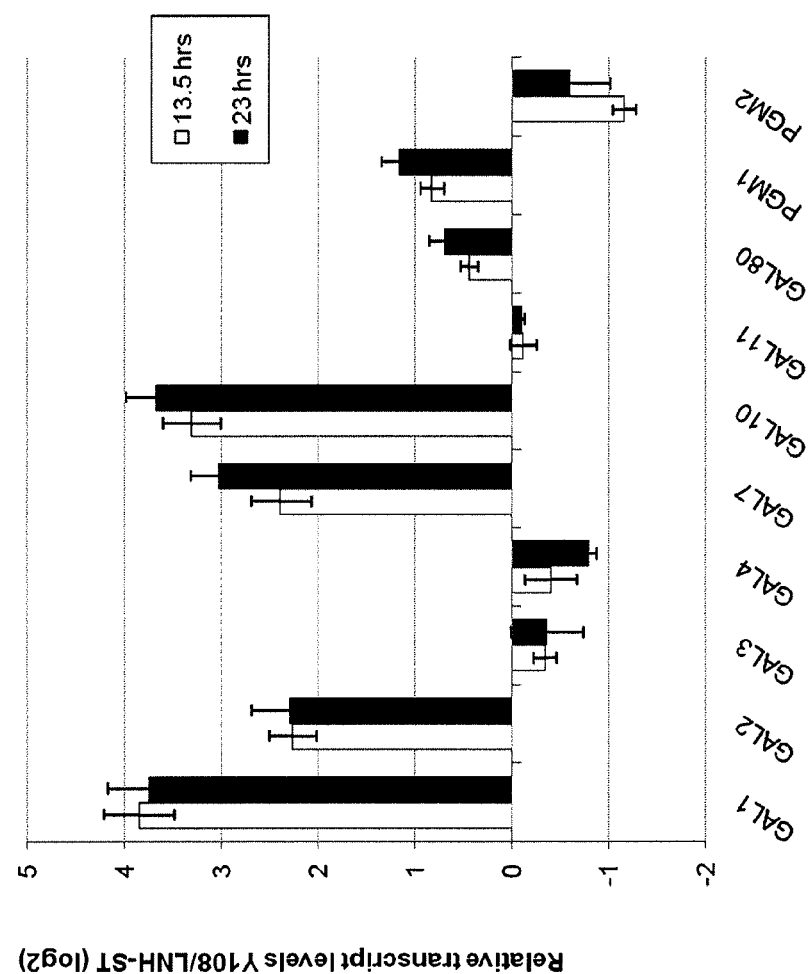
FIG. 12 presents the relative transcript ratios ($Log_2$) of the genes involved in galactose metabolism in the modified yeast strain (Y108-1) vs. the parental strain (LNH-ST) as assessed by microarray hybridization performed as described in Example 4.2. Error bars represent the standard error of the mean (SEM) for duplicate measurements from each of three biological replicates.
Figure 13:
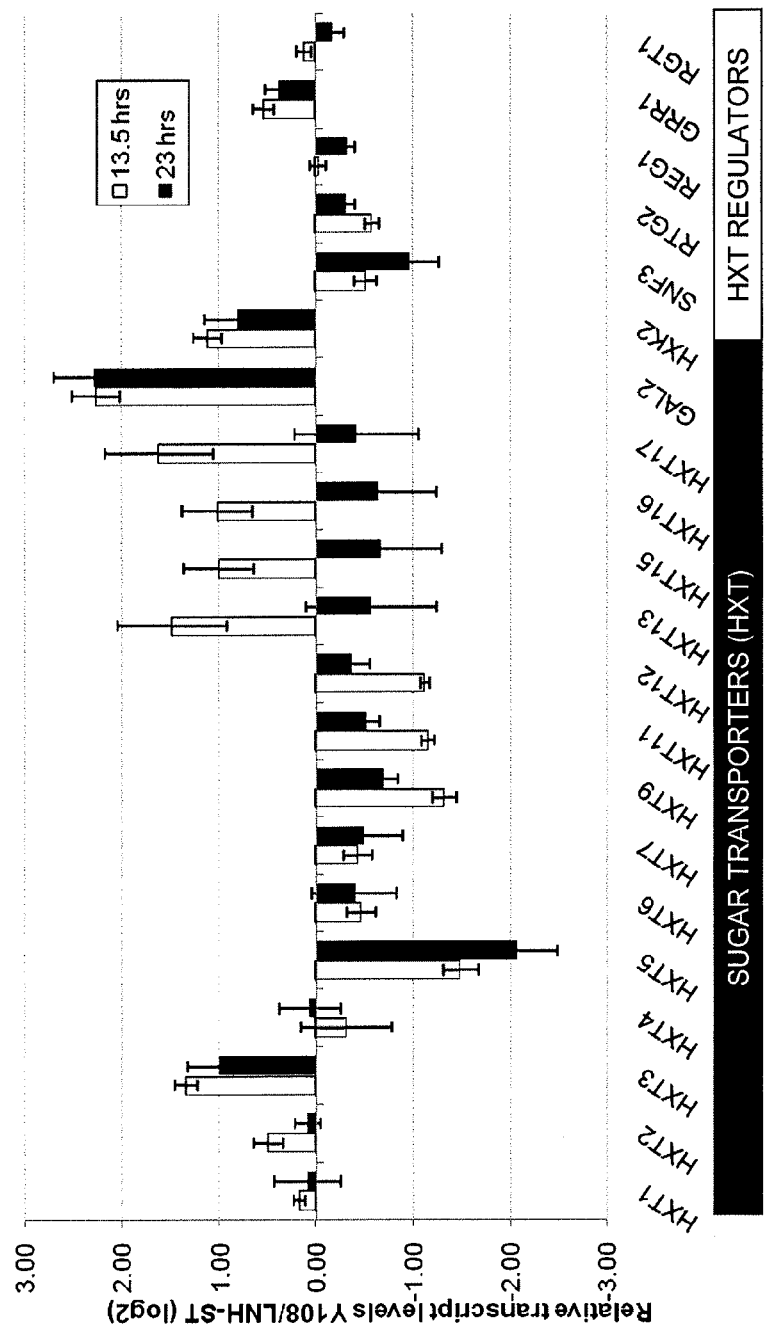
FIG. 13 presents the relative transcript ratios ($Log_2$) of the genes involved in hexose transport in the modified yeast strain (Y108-1) vs. the parental strain (LNH-ST) as assessed by microarray hybridization performed as described in Example 4.2. Error bars represent the standard error of the mean (SEM) for duplicate measurements from each of three biological replicates.
Figure 14:
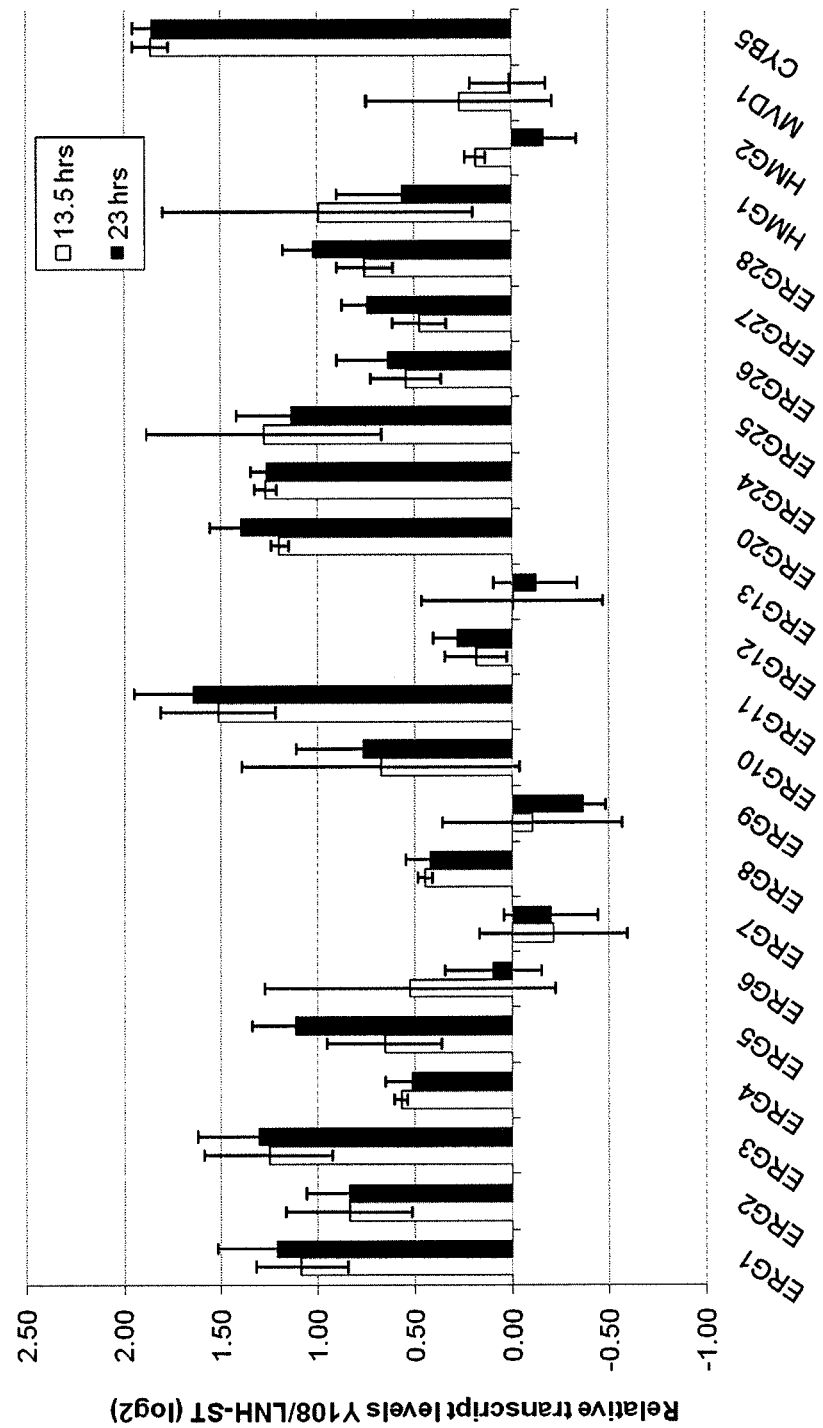
FIG. 14 presents the relative transcript ratios ($Log_2$) of genes involved in ergosterol biosynthesis metabolism in the modified yeast strain (Y108-1) vs. the parental strain (LNH-ST) as assessed by microarray hybridization performed as described in Example 4.2. Error bars represent the standard error of the mean (SEM) for duplicate measurements from each of three biological replicates.

The results are presented in FIGS. 12, 13, and 14. A total of twenty-seven genes showed increased expression in the modified yeast (Y108-1) relative to the parental yeast (LNH-ST) when grown under identical conditions in media containing lignocellulose hydrolysates: GAL1, GAL7, GAL10, GAL80, PGM1, HXT1, HXT2, HXT3, GAL2, HXK2, GRR1, ERG1, ERG8, ERG10, ERG11, ERG20, ERG25, ERG26, ERG27, HMG1, CYB5, ERG2, ERG3, ERG4, ERG5, ERG24, and ERG28. An additional fourteen genes showed decreased expression in the modified yeast (Y108-1) relative to the parental yeast (LNH-ST) when grown under identical conditions in media containing lignocellulose hydrolysates: GAL3, GAL4, GAL11, PGM2, HXT4, HXT5, HXT6, HXT7, HXT9, HXT11, HXT12, SNF3, RTG2, and REG1. The majority of these genes encode proteins that participate in hexose transport (FIG. 13 and Table 1), galactose transport and metabolism (FIG. 12 and Table 1), or ergosterol biosynthesis (FIG. 14 and Table 1).

Example 4.3 qRT-PCR Analysis

For quantitative real-time PCR analysis of selected gene transcripts, single-strand cDNA was prepared using 10 µg of total RNA from each sample. RNA mixed with 1.5 µL of 100 µM of poly(T)$_{20}$ primer (Invitrogen, Carlsbad, Calif.), 2 µL of 25 mM dNTP (each dNTP at 6.25 nM) and volume brought to 25 µL with nuclease-free water (Invitrogen). The RNA mixture was heated on a thermal cycler at 65° C. for 5 min and then cooled to 4° C. To this mixture, 8 µL of 5× first-strand buffer (Invitrogen), 4 µl, of 0.1 M DTT (Invitrogen) and 1 µL of RNaseIN (Promega) were added. Reactions were mixed by vortexing and incubated at 42° C. for 2 min. Following this step, 2 µL of SuperScriptII (Invitrogen) were added. The synthesis reaction was continued for 60 min for all samples and the enzyme was inactivated by heat treatment at 70° C. for 15 min.

The expression levels of the *Pichia stipitis* XR and XDH genes (XYL1 and XYL2, respectively), as well as the *S. cerevisiae* XKS, FUS1, YCL042W, YCL073C, and VBA3 genes were determined by qRT-PCR using a Stratagene MX3000P thermal cycler (Agilent). Transcript levels were determined using the standard curve method. Standard curves were constructed for constitutively expressed reference genes RDN18 and ACT1 and for each of the gene-specific amplicons using primers indicated in Table 5 (SEQ ID NOs:1-18); RDN18 was used as the reference standard for highly expressed XYL1, XYL2, and XKS1 genes, and ACT1 was used as the reference standard for the low- to moderately expressed FUS1, YCL042W, YCL073C, and VBA3 genes. For generation of the RDN18 and ACT1 standard curves, equal aliquots of all collected cDNA samples were pooled, diluted 1:10, 1:20, 1:100, 1:200, and 1:1000 in water, and used for qRT-PCR. To determine the relative transcript level of each gene, individual cDNA samples were diluted 1:50, and 2 μL aliquoted in duplicate into a 96-well PCR microwell plate containing 18 μL of SYBR Green Master Mix composed of: 10 μL of Maxima SYBR Green/Rox qPCR 2× master mix (Fermentas, Burlington, Ontario, Canada), 1 μL of forward and reverse primer solution at 10 μM, and 7 μL of nuclease free water. The PCR reaction consisted of the following steps: I) 1 cycle of 30 sec. at 25° C., 10 min at 95° C.; II) 45 cycles of 30 sec at 95° C., 20 sec at 55° C., and 30 sec at 95° C. Analysis of the data was performed as described in the Stratagene MX3000P manual for converting the fractional cycle at which exponential product is reliably detected (threshold cycle or Ct) to transcript level. Standard curves were plotted for each gene to measure the transcript level. These values were normalized to the reference genes ACT1 or RDN18. The normalized transcript level for each gene for the modified yeast strain was divided by that found for the same transcript in the parental strain. The final value is the ratio of the normalized relative transcript level of the target gene in the modified strain (Y108-1) to that in the parental strain (LNH-ST).

TABLE 5

Primers for qRT-PCR

| SEQ ID | Primer name | Primer sequence |
| --- | --- | --- |
| 1 | ACT1F | TGGTTTCTCTCTACCTCACGCCAT |
| 2 | ACT1R | TCGAAGTCCAAGGCGACGTAACAT |
| 3 | RDN18F | AACTCACCAGGTCCAGACACAATAAGG |
| 4 | RDN18R | AAGGTCTCGTTCGTTATCGCAATTAAGC |
| 5 | XKS1F | TCCGCTGCGGGACTACCTAAATAA |
| 6 | XKS1R | CCAAGGGCACATGAGTTTGGTGTT |
| 7 | psXYL1F | TCGAATTCGCTCAATCCCGTGGTA |
| 8 | psXYL1R | TTGAGCTGGAGACTTACCGTGCTT |
| 9 | psXYL2F | TGTTGGTGTCCACGCCTCTAAGTT |
| 10 | psXYL2R | TGTGAGTAGCAGCACCAATGTCCT |
| 11 | FUS1F | AGGCTAGCGTCCAATTAGGGAAGA |
| 12 | FUS1R | ATCCATCGGTATGAGTGGCCAGAA |
| 13 | YCL042WF | AGTGCCCAACTCAGCTTCCGTAAA |
| 14 | YCL042WR | TCTCAGTGGCTTTGTGTAAGTCGTCG |

TABLE 5-continued

Primers for qRT-PCR

| SEQ ID | Primer name | Primer sequence |
| --- | --- | --- |
| 15 | YCL073CF | TGCCATATGGACACAAACCATGCC |
| 16 | YCL073CR | AACCACAGCATCTCTTTCGGGTGA |
| 17 | VBA3F | CGCTCATGAGTGCACAGCTTCAAA |
| 18 | VBA3R | AGCACACCACCAAGAGTTGTACCT |

Figure 8:
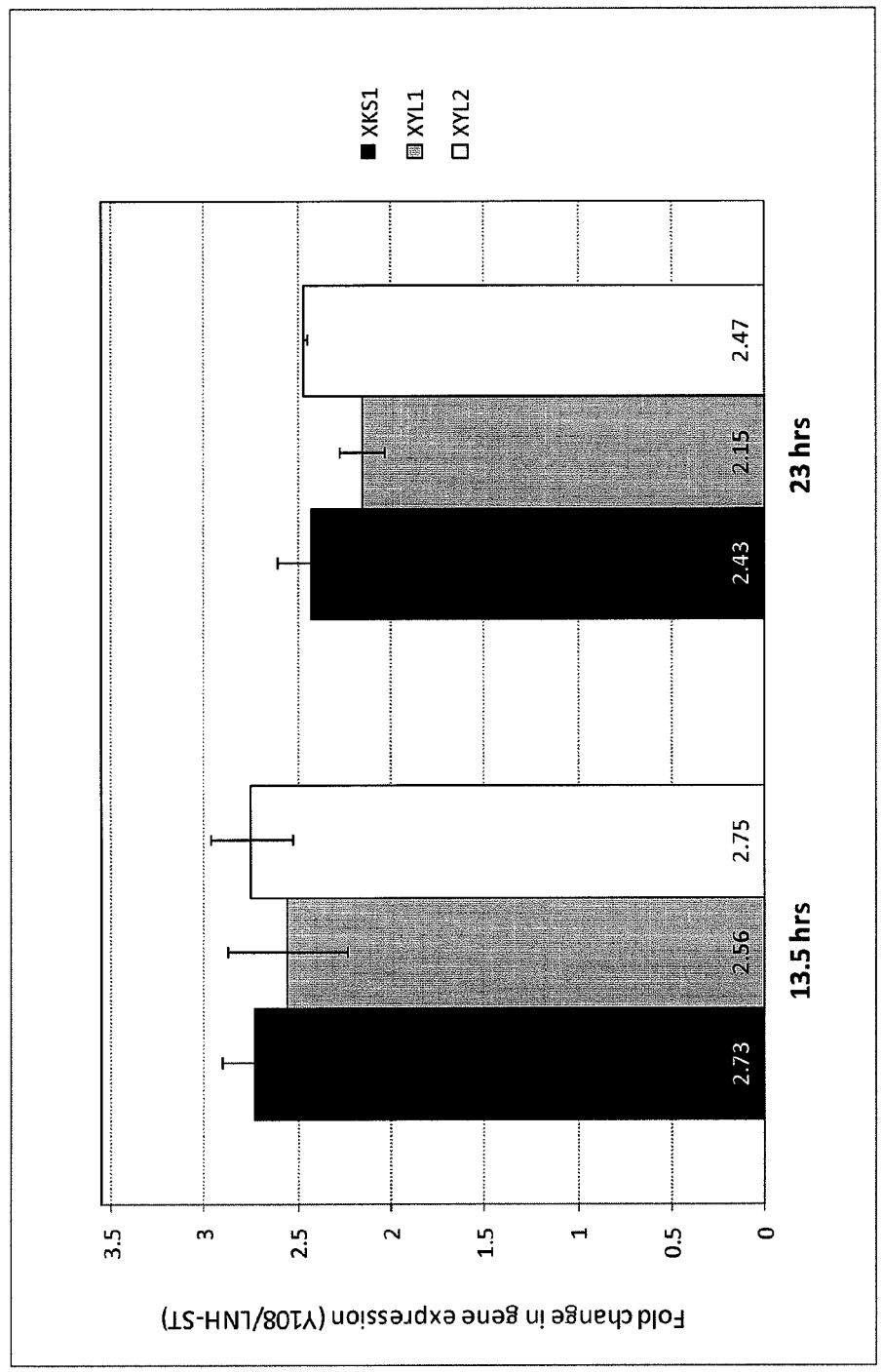
FIG. 8 presents the relative transcript levels of the *S. cerevisiae* XKS1 and *Pichia stipitis* XYL1 and XYL2 genes in modified (Y108-1) and parental (LNH-ST) yeast strains measured using real-time qRT-PCR as described in Example 4.3, and normalized to the transcription levels of the RDN18 gene. Error bars represent the standard error of the mean (SEM) for duplicate measurements from each of two biological replicates.
Figure 9:
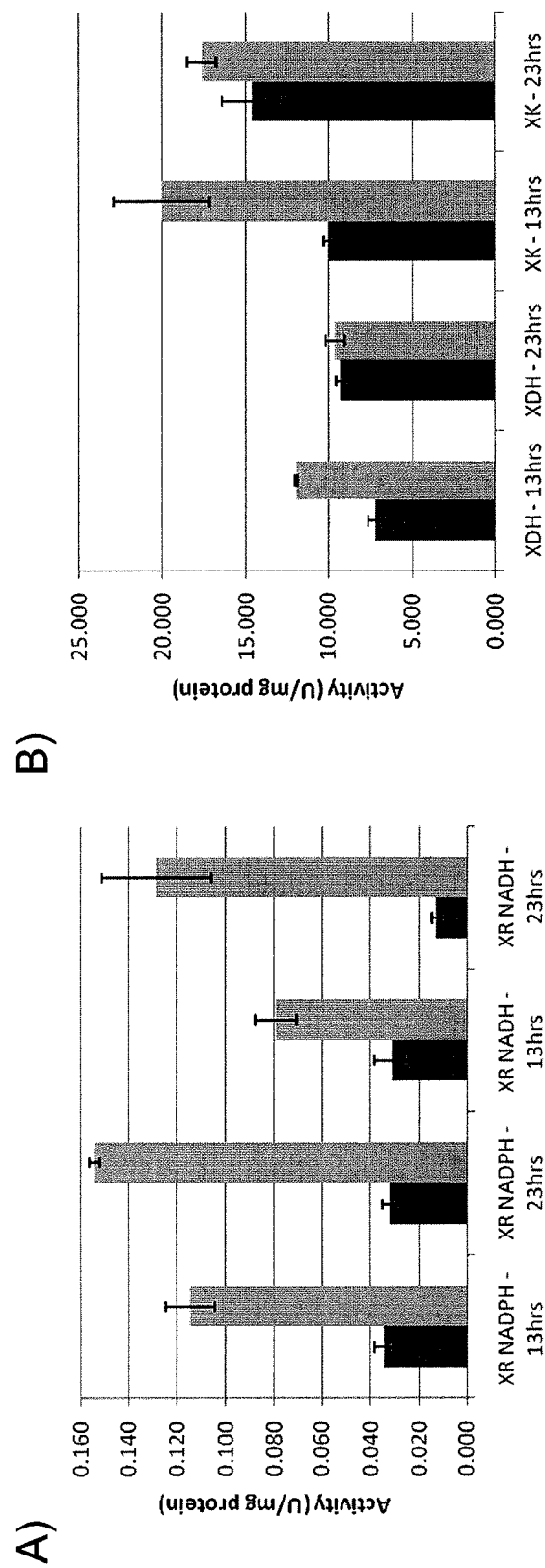
FIG. 9 presents the enzymatic activity of (FIG. 9A) xylose reductase (with NADPH or NADH) and (FIG. 9B) xylitol dehydrogenase and xylulose kinase in parental (LNH-ST, dark grey) and modified (Y108-1, light grey) yeast strains as described in Example 5. Biomass from triplicate fermentations was pooled to produce a single cell-free extract for each strain and time point. Enzymatic activities were determined in duplicate. Average activities and standard deviations are shown.
Figure 10:
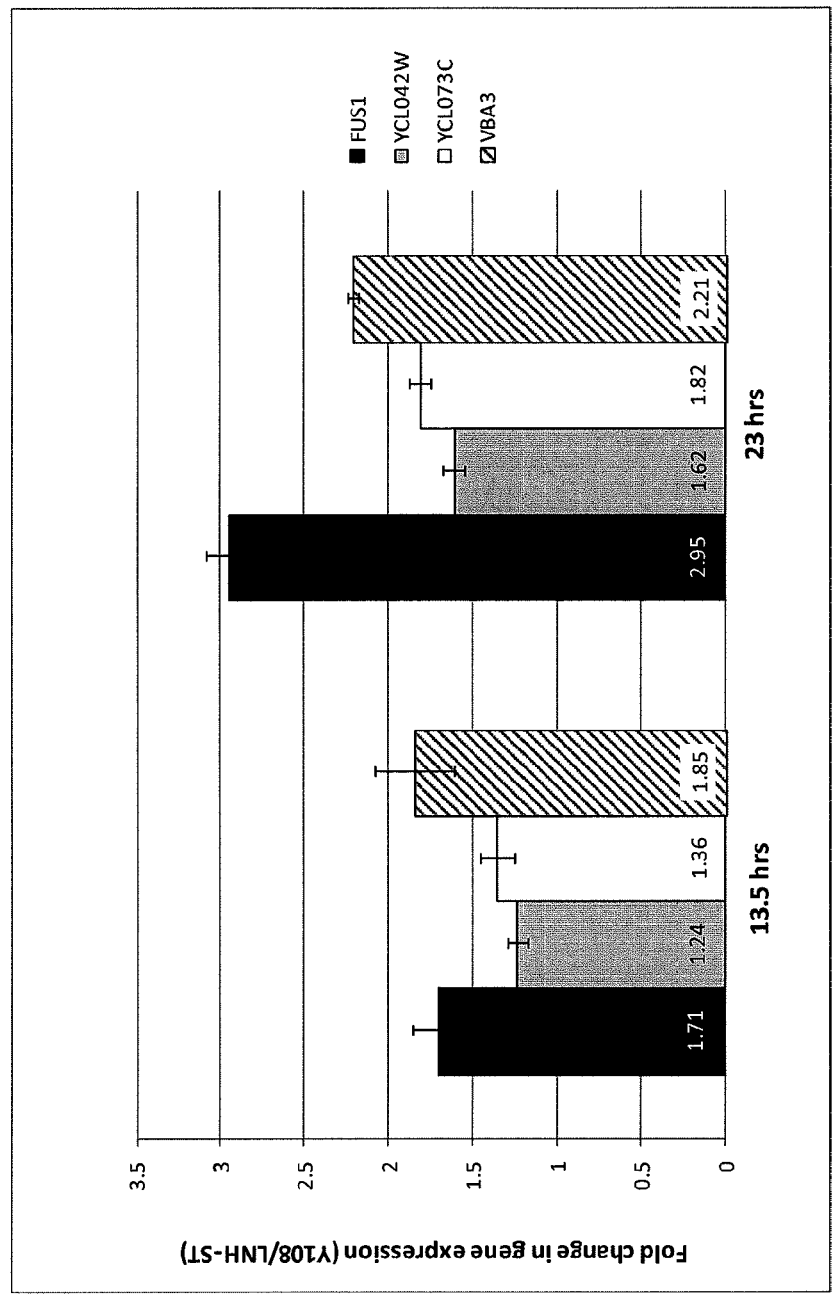
FIG. 10 presents the relative transcript levels of the *S. cerevisiae* FUS1, YCL042W, YCL073C, and VBA3 genes in modified (Y108-1) and parental (LNH-ST) yeast strains measured by real-time qRT-PCR and normalized to the transcription levels of the ACT1 gene. Error bars represent the standard error of the mean (SEM) from each of two biological replicates
Figure 11:
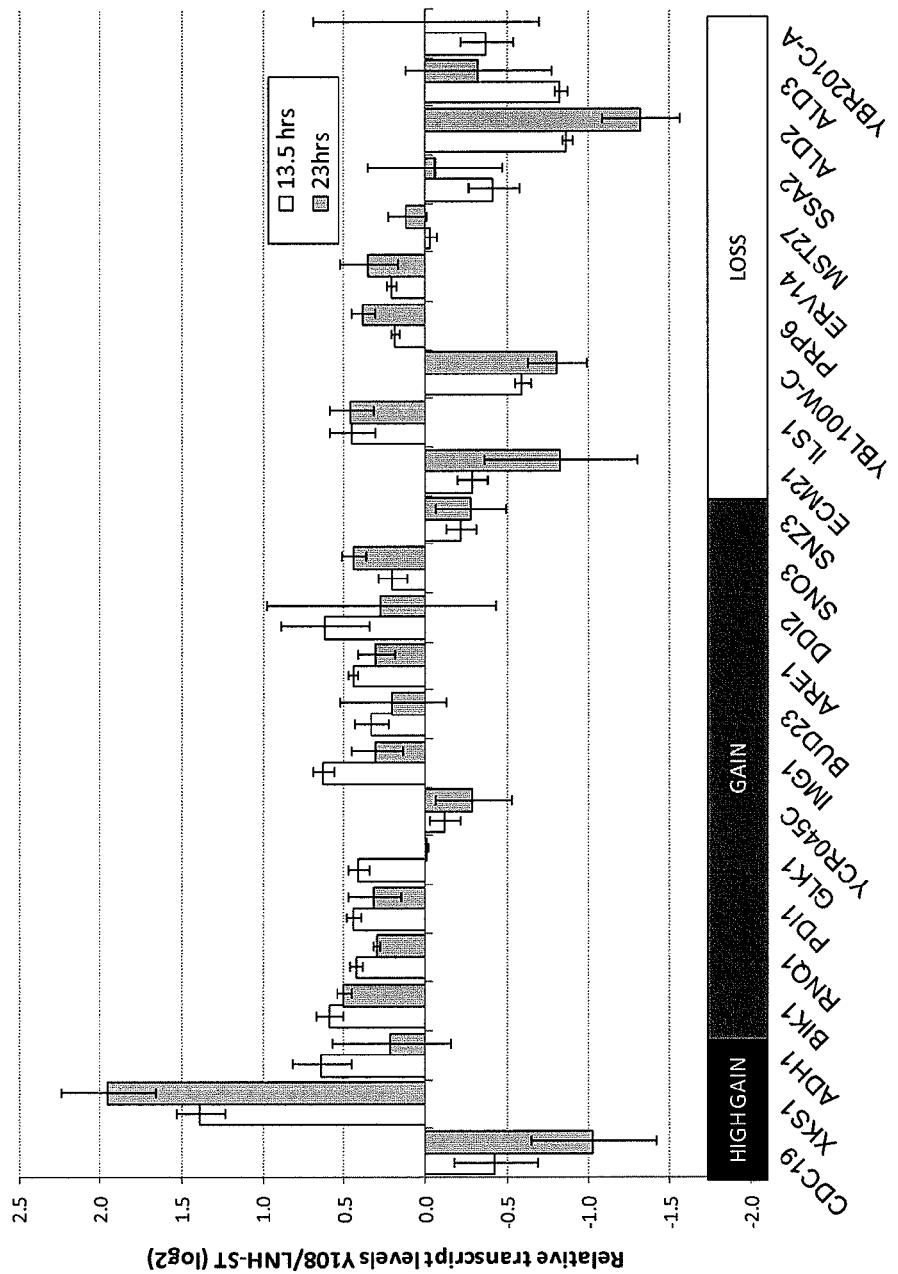
FIG. 11 presents the relative transcript ratios ($Log_2$) of the genes showing copy number gains or losses in the modified yeast strain (Y108-1) vs. the parental strain (LNH-ST) as assessed by microarray hybridization performed as described in Example 4.2. Error bars represent the standard error of the mean (SEM) for duplicate measurements from each of three biological replicates.

The results are presented in FIGS. 8, 10, and 11. All three of the genes encoding the recombinantly introduced xylose metabolic pathway (the *P. stipitis* XYL1 and XYL2 genes encoding the XR and XDH enzymes, respectively, and the *S. cerevisiae* XKS1 gene encoding the XK enzyme) show increased expression in the modified yeast strain relative to the parental yeast strain when cultured under identical conditions in media containing lignocellulose hydrolysates (FIG. 8), which is consistent with the increased copy number observed for the ADH1 and CDC19 promoters linked to the XYL1 and XYL2 genes, respectively. Similarly, other genes that showed either an increase (FUS1, YCL042W, YCL073C, VBA3, BIK1, RNQ1, PDI1, GLK1, IMG1, BUD23, ARE1, DDI2, SNO3) or decrease (ECM21, YBL100W-C, SSA2, ALD2, ALD3, YBR201C-A) in copy number also showed increased or decreased expression, respectively (FIGS. 10 and 11).

Example 5

Determination of Xylose Reductase, Xylitol Dehydrogenase, and Xylulose Kinase Enzyme Activities in Parental and Modified Yeast Strains Example 5.1

Preparation of Yeast Cell Lysates

Yeast samples with approximately 10 g/L of biomass were taken from each of triplicate AFM flasks at time points of 13.5 h and 23 h into fermentation. Biomass was collected by centrifugation at 14,000 rpm for 3 min, washed in cold sterile water three times, and frozen in liquid nitrogen. From these triplicate archive samples, a pooled mass of 0.0625 g of cells was isolated and centrifuged for 10 min at 4150 RPM and 0° C. The pellet was then washed in ice-cold freeze buffer (10 mM potassium phosphate buffer (KPB)+2 mM EDTA, pH 7.5), centrifuged again (4150 RPM, 0° C.), resuspended in 4 mL of freeze buffer, and stored at −20° C. prior to preparation of cell-free lysates. Lysates were prepared from the frozen cells by thawing the samples, centrifuging for 3 min (4150 RPM, 0° C.), and washing the pellet in ice-cold sonication buffer (100 mM KPB+2 mM MgCl$_2$, pH 7.5); this was followed by another centrifugation and resuspension in 4 mL ice-cold sonication buffer with 40 μL 1,4-dithiothreitol. The cells were then lysed by placing 0.5 mL of the cell suspension into a 2 mL Eppendorf tube containing 0.5 g of acid-washed glass beads and agitated in an MP FastPrep-24 (MP Biomedicals) at 6 m/s for 50 seconds, followed by a cooling period (5 min) on ice. The agitation/cooling process was performed twice. Lastly, the samples were spun down for 5 min at 14,500 RPM to remove cell debris, and the lysate was removed and kept on ice until use. Protein concentrations of the lysates were measured using the Lowry method (Lowry et al. (1951)

J. Biol. Chem. 193:265-75) with bovine serum albumin as a standard in a Cary300 spectrophotometer at 660 nm.

Example 5.2

Xylose Reductase (XR) Assay

The formation of D-xylitol (XOH) from D-xylose (X) was recorded by monitoring the oxidation of NADPH and NADH (in separate reactions) at 340 nm and 30° C. using the Cary300 Kinetics program. The reaction mixtures were performed in a 1 mL cuvette and consisted of DI water (800 µL-X µL CFE), 50 mM Tris-HCl buffer (pH 7.0), 0.3 mM NADPH or NADH, and lysate. The cuvette was placed in the Cary300 and the background signal was recorded. The reaction was started by adding the substrate (150 mM D-xylose) and terminated by simply removing the cuvette. Enzyme activity was calculated from the change in absorbance difference between the slope of the background signal and the slope of the signal after substrate addition per unit time using Beer's Law and the molar extinction coefficient of NAD(P)H (6.3 mL/mM). This value was then normalized for the protein concentration in the lysate and final activity was expressed as U/mg protein.

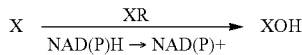

The results are shown in FIG. 9A. The modified yeast strain (Y108-1) exhibits higher levels of xylose reductase activity, using either NADPH or NADH as a cofactor, than the parental strain (LNH-ST), consistent with the increased copy number and expression of the P. stipitis XYL1 gene.

Example 5.3

Xylose Dehydrogenase (XDH) Assay

The formation of D-xylulose from D-xylitol was determined by monitoring the reduction of NAD+. The procedure for measuring XDH activity was the same as previously described for xylose reductase. The reaction mixture consisted of deionized water (795 µL-X µL lysate), 100 mM glycine (pH 9.0), 50 mM MgCl$_2$.6H$_2$O, 3.0 mM NAD+ and X µL lysate; the reaction was initiated by adding 300 mM xylitol.

The results are shown in FIG. 9B. The modified yeast strain (Y108-1) exhibits higher levels of xylitol dehydrogenase activity than the parental strain (LNH-ST), consistent with the increased copy number and expression of the P. stipitis XYL2 gene.

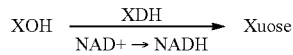

Example 5.4

Xylulose Kinase (XK) Assay

The XK activity is measured by monitoring lactate formation from pyruvate via lactate dehydrogenase (LDH)-facilitated oxidation of NADH. The pyruvate originates from the previous reaction involving the dephosphorylation of phoenolpyruvate (PEP) via pyruvate kinase (PK) using ADP, which in turn was produced from the phosphorylation of D-xylulose by XK.

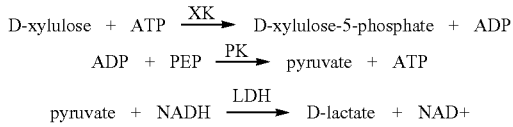

Data was obtained using the same procedure as for XR and XDH. The reaction mixture was composed of DI water (470 µL-X µL lysate), 0.1 M Tris-HCl (pH 7.0), 50 mM MgCl$_2$.6H$_2$O, 5 mM ATP, 0.6 mM PEP, 20 U PK, 20 U LDH, 0.3 mM NADH and X µL lysate. The reaction was started using 40 mM D-xylulose.

The results are shown in FIG. 9B. The modified yeast strain (Y108-1) exhibits higher levels of xylulose kinase activity than the parental strain (LNH-ST), consistent with the increased copy number and expression of the XKS1 gene in the modified yeast.

Example 6

Phenotypic Complementation

Yeast from the knockout and overexpression collections (Open Biosystems, Huntsville, Ala.) were identified through the corresponding gene copy number gains or copy number losses in CGH analysis (Example 3.2) and through corresponding up- and downregulation in the transcriptional microarray analysis (Example 4.2). Genes that were lost or gained or up- or down-regulated in Y108-1 compared to LNH-ST are thought to contribute to a beneficial phenotype with respect to fermentation and growth in lignocellulosic hydrolysate.

In order to enable xylose metabolism and compare the effects of deleting or overexpressing the CGH identified genes, the yeast strains in Table 6 were transformed with the pLNH-ST plasmid (FIG. 15) using the lithium acetate method of Gietz et al. ((2002) Methods in Enzymology 350:87-96). Briefly, yeast strains were inoculated into 20 mL of 2×YPD (10 g/L yeast extract, 20 g/L peptone, 60 g/L dextrose) and grown overnight. Afterwards, the cell titer was determined using a hemocytometer, and 2.5×10$^8$ cells were added to a 50 mL flask with 2×YPD. This mixture was grown until the cell titer was at least 2×10$^7$ cells/mL (approximately 4 hours of growth). The cells were harvested, washed in sterile water, and resuspended in 1 mL of sterile water. 100 µL samples were pipetted into 1.5 mL microfuge tubes (one tube per transformation), centrifuged and the supernatant removed. 360 µL of transformation mix (consisting of 240 µL polyethylene glycol (50% w/v), 36 µL 1.0 M lithium acetate, 50 µL boiled single strand carrier DNA, and 34 µL purified pLNH plasmid) was added to the cells and vortexed. The cells were incubated in a 42° C. water bath for 90 minutes. After incubation, the cells were centrifuged, and the transformation mix was removed and resuspended in 1 mL sterile water. Appropriate dilutions were performed and the cells were plated on Synthetic prop-out (SD)+xylose media consisting of 0.13% amino acid drop-out media minus uracil, 0.17% yeast nitrogen base, 0.5% ammonium sulfate and 2% xylose with 76 mg/L uracil added (parent and the knockouts) or without uracil (overexpressors) at pH 5.5. The plates for the control and overexpressors contained 100 µg/mL geneticin, whereas the knockout plates (already geneticin resistant) contained 800 µg/mL geneticin. The cells were grown for approximately 4 days at 30° C.

To observe any differences in growth, the transformants were plated on glucose-free dilute lignocellulosic hydrolysate plates and compared to growth on SD+xylose plates (FIGS. 16 and 17). Glucose was removed from the hydrolysate by fermentation with commercially available *S. cerevisiae*. The resulting fermentation broth was diluted to 20% of its original concentration (~14 g/L xylose) and sterile filtered. This was then mixed with an autoclaved 30 g/L agar solution and allowed to cool, resulting in 10% lignocellulosic hydrolysate plates. Transformed cultures were incubated for approximately 5 days at 30° C.

TABLE 6

Yeast Strains Used in Phenotypic Complementation Study. All strains are derivatives of the parental strain BY4741 (MATa his3Δ1 leu2Δ0 met15Δ0 ura3Δ0) (Open Biosystems Catalog No.)

| Open Biosystems Catalog No. | Target Gene | Overexpressed (OE) or Deleted (Knock out) |
|---|---|---|
| YSC4515-98805369 | BIK1 | GST-Tagged Strain (OE) |
| YSC4515-98805380 | GLK1 | GST-Tagged Strain (OE) |
| YSC4515-98805403 | VBA3 | GST-Tagged Strain (OE) |
| YSC4515-98806294 | SNO3 | GST-Tagged Strain (OE) |
| YSC4515-98806293 | SNZ3 | GST-Tagged Strain (OE) |
| YSC1021-551507 | ALD2 | Yeast Knock Out Strain |
| YSC1021-551506 | ALD3 | Yeast Knock Out Strain |
| YSC1021-552545 | HXT5 | Yeast Knock Out Strain |
| YSC1021-552203 | HXT3 | Yeast Knock Out Strain |
| YSC4515-98807506 | ERG3 | GST-Tagged Strain (OE) |
| YSC4515-98806621 | ERG1 | GST-Tagged Strain (OE) |
| YSC1021-555053 | GAL1 | Yeast Knock Out Strain |
| YSC4515-98807524 | GAL2 | GST-Tagged Strain (OE) |
| YSC4515-98805110 | GAL10 | GST-Tagged Strain (OE) |
|  | BY4741 | Yeast Parental Strain |

Example 7

Examination of Galactose Metabolism in a Lignocellulosic Background

LNH-ST and Y108-1 were grown in pure sugar media #5 (using 60 g/L galactose instead of glucose) at 30° C. for three days. To investigate galactose metabolism in a lignocellulosic background, sugar-depleted media was prepared. A fermentation was conducted with Y108-1 in order to consume all available fermentable sugars. The fermentation beer was then sterile filtered, and to this 60 g/L galactose and 1 mL/L each of vitamins and traces were added. LNH-ST and Y108-1 were inoculated into the galactose-containing lignocellulosic hydrolysate and monitored for three days. Sterile samples were withdrawn daily for HPLC analysis, as described in Example 1. Under pure sugar conditions, yields and extent of galactose conversion were not significantly different. In a lignocellulosic background, the parental strain LNH-ST fails to consume all of the available galactose; whereas the modified strain Y108-1 consumes all of the available galactose.

TABLE 7

LNH-ST and Y108-1 Were Grown in Either Pure Sugar Media or Process Broth (Beer) Supplemented with 60 g/L Galactose

|  | Pure Sugar | | Process Broth + Galactose | |
|---|---|---|---|---|
|  | LNH-ST | Y108-1 | LNH-ST | Y108-1 |
| $Y_{Ethanol/Gal}$ (g/g) | 0.34 | 0.36 | 0.33 | 0.35 |
| $Y_{Cells/Gal}$ (g/g) | 0.10 | 0.09 | 0.07 | 0.10 |
| % Galactose conversion | 100 | 100 | 92 | 100 |

What is claimed:

1. A modified yeast strain capable of utilizing xylose in a lignocellulosic hydrolysate for growth or fermentation, comprising
an increase in copy number or expression of one or more genes selected from the group consisting of ARE1, VBA3, RNQ1, FUS1, PDI1, BUD23, IMG1, DDI2, SNO3, SNZ3, YCL042W, YCL073C, YCR045C, and tE(UUC)B;
a decrease in copy number or expression of one or more genes selected from the group consisting of ALD2, SSA2, MST27, PRM8, ERV14, ECM21, ILS1, PRP6, YBL100W-C, YBR201C-A, and tE(UUC)G2; or
both (a) and (b),
relative to a parental yeast strain from which the modified yeast strain is derived.

2. The modified yeast strain of claim 1, further comprising
an increase in copy number or expression of one or more genes selected from the group consisting of GAL1, GAL7, GAL10, GAL80, PGM1, HXT1, HXT2, HXT3, GAL2, HXK2, GRR1, ERG1, ERG8, ERG10, ERG11, ERG20, ERG25, ERG26, ERG27, HMG1, and CYB5;
a decrease in copy number or expression of one or more genes selected from the group consisting of GAL3, GAL4, GAL11, PGM2, HXT4, HXT5, HXT6, HXT7, HXT9, HXT11, HXT12, SNF3, RTG2, and REG1; or
both (a) and (b),
relative to a parental yeast strain from which the modified yeast strain is derived.

3. The modified yeast strain of claim 1, further comprising
(a) an increase in copy number or expression of one or more genes selected from the group consisting of BIK1, GLK1, ERG2, ERG3, ERG4, ERG5, ERG24, and ERG28;
(b) a decrease in copy number or expression of ALD3; or
(c) both (a) and (b),
relative to a parental yeast strain from which the modified yeast strain is derived.

4. The modified yeast strain of claim 1, wherein the modified yeast strain is also capable of fermenting glucose in a lignocellulosic hydrolysate to ethanol.

5. The modified yeast strain of claim 1, wherein the modified yeast strain is also capable of fermenting arabinose in a lignocellulosic hydrolysate to ethanol.

6. The modified yeast strain of claim 1, wherein the strain is of the genus Saccharomyces.

7. The modified yeast strain of claim 6, wherein the parental yeast strain comprises introduced genes encoding xylose reductase, xylitol dehydrogenase, and xylulokinase.

8. The modified yeast strain of claim 7, wherein the modified yeast strain further comprises increases in copy number or expression of the introduced genes encoding xylose reductase, xylitol dehydrogenase, and xylulokinase relative to the parental yeast strain.

9. The modified yeast strain of claim 6, wherein the parental yeast strain comprises introduced genes encoding xylulokinase and one or more xylose isomerase.

10. The modified yeast strain of claim 1, wherein the increase or decrease in copy number or expression of the one or more genes is the result of an adaptive evolution technique.

11. The modified yeast strain of claim 1, wherein the increase or decrease in copy number or expression of the one or more genes is the result of genetic engineering.

12. The modified yeast strain of claim 6, wherein the parental yeast strain is LNH-ST.

13. The modified yeast strain of claim 12, wherein the modified yeast strain capable of utilizing xylose is Y108-1 (ATCC Deposit No. PTA-10567).

14. A modified Saccharomyces cerevisiae yeast strain capable of utilizing xylose in a lignocellulosic hydrolysate for growth or fermentation, comprising
(a) an increase in copy number or expression of one or more genes selected from the group consisting of ARE1, VBA3, RNQ1, FUS1, PDI1, BUD23, IMG1, DDI2, SNO3, SNZ3, YCL042W, YCL073C, YCR045C, and tE(UUC)B;
(b) a decrease in copy number or expression of one or more genes selected from the group consisting of ALD2, SSA2, MST27, PRM8, ERV14, ECM21, ILS1, PRP6, YBL100W-C, YBR201C-A, and tE(UUC)G2;
(c) an increase in copy number or expression of one or more genes selected from the group consisting of GAL1, GAL7, GAL10, GAL80, PGM1, HXT1, HXT2, HXT3, GAL2, HXK2, GRR1, ERG1, ERG8, ERG10, ERG11, ERG20, ERG25, ERG26, ERG27, HMG1, and CYB5; and (d) a decrease in copy number or expression of one or more genes selected from the group consisting of GAL3, GAL4, GAL11, PGM2, HXT4, HXT5, HXT6, HXT7, HXT9, HXT11, HXT12, SNF3, RTG2, and REG1, relative to a parental yeast strain from which the modified yeast strain is derived, said modified yeast strain further comprising introduced genes encoding xylose reductase, xylitol dehydrogenase and xylulokinase.

15. A method of converting xylose in a lignocellulosic hydrolysate to a fermentation product, comprising the steps of:

contacting the lignocellulosic hydrolysate with the modified yeast strain according to any one of claims 1, 3, 4 or 14; and (b) recovering the fermentation product.

16. The process of claim 15, wherein the fermentation product is an alcohol or a sugar alcohol.

17. The process of claim 16, wherein the alcohol is ethanol and the sugar alcohol is xylitol.

* * * * *

SEQUENCE LISTING

<160> NUMBER OF SEQ ID NOS: 18

<210> SEQ ID NO 1
<211> LENGTH: 24
<212> TYPE: DNA
<213> ORGANISM: Artificial
<220> FEATURE:
<223> OTHER INFORMATION: Primer Sequence for ACT1F(forward)

<400> SEQUENCE: 1
tggtttctct ctacctcacg ccat                                    24

<210> SEQ ID NO 2
<211> LENGTH: 24
<212> TYPE: DNA
<213> ORGANISM: Artificial
<220> FEATURE:
<223> OTHER INFORMATION: Primer Sequence for ACT1R(reverse)

<400> SEQUENCE: 2
tcgaagtcca aggcgacgta acat                                    24

<210> SEQ ID NO 3
<211> LENGTH: 27
<212> TYPE: DNA
<213> ORGANISM: Artificial
<220> FEATURE:

```
<223> OTHER INFORMATION: Primer Sequence for RDN18F(forward)

<400> SEQUENCE: 3
aactcaccag gtccagacac aataagg                                           27

<210> SEQ ID NO 4
<211> LENGTH: 28
<212> TYPE: DNA
<213> ORGANISM: Artificial
<220> FEATURE:
<223> OTHER INFORMATION: Primer Sequence for RDN18R(reverse)

<400> SEQUENCE: 4
aaggtctcgt tcgttatcgc aattaagc                                          28

<210> SEQ ID NO 5
<211> LENGTH: 24
<212> TYPE: DNA
<213> ORGANISM: Artificial
<220> FEATURE:
<223> OTHER INFORMATION: Primer Sequence for XKS1F(forward)

<400> SEQUENCE: 5
tccgctgcgg gactacctaa ataa                                              24

<210> SEQ ID NO 6
<211> LENGTH: 24
<212> TYPE: DNA
<213> ORGANISM: Artificial
<220> FEATURE:
<223> OTHER INFORMATION: Primer Sequence for XKS1R(reverse)

<400> SEQUENCE: 6
ccaagggcac atgagtttgg tgtt                                              24

<210> SEQ ID NO 7
<211> LENGTH: 24
<212> TYPE: DNA
<213> ORGANISM: Artificial
<220> FEATURE:
<223> OTHER INFORMATION: Primer Sequence for psXYL1F(forward)

<400> SEQUENCE: 7
tcgaattcgc tcaatcccgt ggta                                              24

<210> SEQ ID NO 8
<211> LENGTH: 24
<212> TYPE: DNA
<213> ORGANISM: Artificial
<220> FEATURE:
<223> OTHER INFORMATION: Primer Sequence for psXYL1R(reverse)

<400> SEQUENCE: 8
ttgagctgga gacttaccgt gctt                                              24

<210> SEQ ID NO 9
<211> LENGTH: 24
<212> TYPE: DNA
<213> ORGANISM: Artificial
<220> FEATURE:
<223> OTHER INFORMATION: Primer Sequence for psXYL2F(forward)

<400> SEQUENCE: 9
tgttggtgtc cacgcctcta agtt                                              24

<210> SEQ ID NO 10
```

```
<211> LENGTH: 24
<212> TYPE: DNA
<213> ORGANISM: Artificial
<220> FEATURE:
<223> OTHER INFORMATION: Primer Sequence for psXYL2R(reverse)

<400> SEQUENCE: 10
tgtgagtagc agcaccaatg tcct                                          24

<210> SEQ ID NO 11
<211> LENGTH: 24
<212> TYPE: DNA
<213> ORGANISM: Artificial
<220> FEATURE:
<223> OTHER INFORMATION: Primer Sequence for FUS1F(forward)

<400> SEQUENCE: 11
aggctagcgt ccaattaggg aaga                                          24

<210> SEQ ID NO 12
<211> LENGTH: 24
<212> TYPE: DNA
<213> ORGANISM: Artificial
<220> FEATURE:
<223> OTHER INFORMATION: Primer Sequence for FUS1R(reverse)

<400> SEQUENCE: 12
atccatcggt atgagtggcc agaa                                          24

<210> SEQ ID NO 13
<211> LENGTH: 24
<212> TYPE: DNA
<213> ORGANISM: Artificial
<220> FEATURE:
<223> OTHER INFORMATION: Primer Sequence for YCL042WF(forward)

<400> SEQUENCE: 13
agtgcccaac tcagcttccg taaa                                          24

<210> SEQ ID NO 14
<211> LENGTH: 26
<212> TYPE: DNA
<213> ORGANISM: Artificial
<220> FEATURE:
<223> OTHER INFORMATION: Primer Sequence for YCL042WR(reverse)

<400> SEQUENCE: 14
tctcagtggc tttgtgtaag tcgtcg                                        26

<210> SEQ ID NO 15
<211> LENGTH: 24
<212> TYPE: DNA
<213> ORGANISM: Artificial
<220> FEATURE:
<223> OTHER INFORMATION: Primer Sequence for YCL073CF(forward)

<400> SEQUENCE: 15
tgccatatgg acacaaacca tgcc                                          24

<210> SEQ ID NO 16
<211> LENGTH: 24
<212> TYPE: DNA
<213> ORGANISM: Artificial
<220> FEATURE:
<223> OTHER INFORMATION: Primer Sequence for YCL073CR(reverse)

<400> SEQUENCE: 16
```

-continued

```
aaccacagca tctctttcgg gtga                                        24

<210> SEQ ID NO 17
<211> LENGTH: 24
<212> TYPE: DNA
<213> ORGANISM: Artificial
<220> FEATURE:
<223> OTHER INFORMATION: Primer Sequence for VBA3F(forward)

<400> SEQUENCE: 17
cgctcatgag tgcacagctt caaa                                        24

<210> SEQ ID NO 18
<211> LENGTH: 24
<212> TYPE: DNA
<213> ORGANISM: Artificial
<220> FEATURE:
<223> OTHER INFORMATION: Primer Sequence for VBA3R(reverse)

<400> SEQUENCE: 18
agcacaccac caagagttgt acct                                        24
```